United States Patent
Kaneko et al.

(10) Patent No.: US 11,281,102 B2
(45) Date of Patent: Mar. 22, 2022

(54) FLUORINE-CONTAINING MONOMER, FLUORINE-CONTAINING POLYMER, PATTERN FORMING COMPOSITION USING SAME, AND PATTERN FORMING METHOD OF SAME

(71) Applicant: Central Glass Company, Limited, Ube (JP)

(72) Inventors: Yuzuru Kaneko, Tokyo (JP); Tsubasa Itakura, Fujimino (JP); Ryo Nadano, Saitama (JP)

(73) Assignee: Central Glass Company, Limited, Ube (JP)

( * ) Notice: Subject to any disclaimer, the term of this patent is extended or adjusted under 35 U.S.C. 154(b) by 1 day.

(21) Appl. No.: 16/616,012

(22) PCT Filed: May 28, 2018

(86) PCT No.: PCT/JP2018/020270
§ 371 (c)(1),
(2) Date: Nov. 22, 2019

(87) PCT Pub. No.: WO2018/225549
PCT Pub. Date: Dec. 13, 2018

(65) Prior Publication Data
US 2020/0089116 A1 Mar. 19, 2020

(30) Foreign Application Priority Data

Jun. 5, 2017 (JP) .............................. JP2017-111208
May 24, 2018 (JP) .............................. JP2018-099306

(51) Int. Cl.
| | | |
|---|---|---|
| G03F 7/039 | (2006.01) | |
| G03F 7/20 | (2006.01) | |
| G03F 7/004 | (2006.01) | |
| C07D 307/04 | (2006.01) | |
| C08F 20/02 | (2006.01) | |

(52) U.S. Cl.
CPC ......... *G03F 7/0397* (2013.01); *C07D 307/04* (2013.01); *C08F 20/02* (2013.01); *G03F 7/0045* (2013.01); *G03F 7/0046* (2013.01); *G03F 7/20* (2013.01)

(58) Field of Classification Search
CPC ... G03F 7/0397; G03F 7/0046; C07D 307/04; C08F 20/02
See application file for complete search history.

(56) References Cited

U.S. PATENT DOCUMENTS

| | | |
|---|---|---|
| 3,949,112 A | 4/1976 | Pattison |
| 2005/0165249 A1 | 7/2005 | Komata et al. |
| 2006/0093960 A1 | 5/2006 | Kinsho et al. |
| 2016/0062242 A1 | 3/2016 | Hamaguchi et al. |

FOREIGN PATENT DOCUMENTS

| | | | |
|---|---|---|---|
| JP | 50-1004 B1 | 1/1975 | |
| JP | 4-26850 A | 1/1992 | |
| JP | 2005-206587 A | 8/2005 | |
| JP | 2006-152255 A | 6/2006 | |
| JP | 2010-106138 A | 5/2010 | |
| JP | 2010106138 A | * 5/2010 | |
| JP | 2012-42837 A | 3/2012 | |
| JP | 2013-33262 A | 2/2013 | |
| JP | 2016-87602 A | 5/2016 | |
| WO | WO 2014/178279 A1 | 11/2014 | |

OTHER PUBLICATIONS

English translation of JP2010106138. (Year: 2010).*
International Search Report (PCT/ISA/210) issued in PCT Application No. PCT/JP2018/020270 dated Aug. 28, 2018 with English translation (three (3) pages).
Japanese-language Written Opinion (PCT/ISA/237) issued in PCT Application No. PCT/JP2018/020270 dated Aug. 28, 2018 (three (3) pages).

* cited by examiner

*Primary Examiner* — Chanceity N Robinson
*Assistant Examiner* — Anna Malloy
(74) *Attorney, Agent, or Firm* — Crowell & Moring LLP

(57) ABSTRACT

Provided is a fluorine-containing polymer which has no perfluoroalkyl group of 4 or more carbon atoms and which, when formed together with a photoacid generator into a film, shows water repellency after film formation, but becomes hydrophilic by the action of an acid generated under light irradiation, and thus serves as a pattern forming material capable of forming a film with high sensitivity and resolution. A fluorine-containing polymer according to the present invention has a repeating unit of the formula (1)

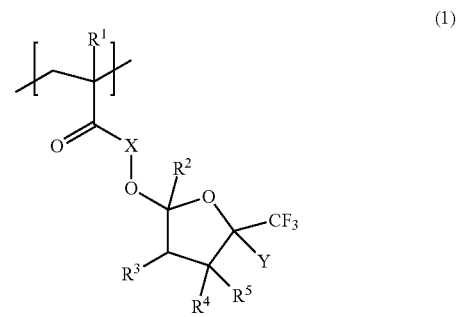

(1)

where $R^1$ is a hydrogen atom, a fluorine atom or a $C_1$-$C_{10}$ alkyl group; $R^2$ to $R^5$ are each independently a hydrogen atom or a $C_1$-$C_{10}$ alkyl group; X is a single bond or a divalent group; Y is a $C_1$-$C_3$ fluoroalkyl or carboxylate (—COOR) group; R is a $C_1$-$C_3$ fluoroalkyl group; and seven or less of hydrogen atoms contained in the substituent group may be substituted with fluorine.

16 Claims, No Drawings

… (1 / 20)

FLUORINE-CONTAINING MONOMER, FLUORINE-CONTAINING POLYMER, PATTERN FORMING COMPOSITION USING SAME, AND PATTERN FORMING METHOD OF SAME

FIELD OF THE INVENTION

The present invention relates to a fluorine-containing monomer, a fluorine-containing polymer, a pattern forming composition using the fluorine-containing polymer, and a pattern forming method using the pattern forming composition. More particularly, the present invention relates to a fluorine-containing polymer usable as a resist material for lithography in semiconductor manufacturing process and usable for printed electronics in which an electronic circuit of ink such as a pattern circuit of conductive ink is formed on a substrate of glass or resin by printing the ink in electronic equipment manufacturing process, a fluorine-containing monomer as a precursor of the fluorine-containing polymer, a pattern forming composition using the fluorine-containing polymer, and a pattern forming method using the pattern forming composition.

BACKGROUND ART

Fluorine-containing polymers are known for excellent properties due to the presence of fluorine in their chemical structures. Fluorine-containing polymers with water repellency, heat resistance, transparency, low refractive index, photosensitivity etc. are used as resist materials in semiconductor manufacturing and as pattern forming materials in printed electronics.

A fluorine-containing polymer having an acid-decomposable group is used as a resist material in semiconductor manufacturing such that, when the fluorine-containing polymer is formed into a resist film by being mixed with a photoacid generator, the developer soluble or insoluble properties of the fluorine-containing polymer are changed to allow patterning of the resist film due to dissociation of the acid-decomposable group from the fluorine-containing polymer by the action of an acid generated from the photoacid generator under light irradiation. Further, a fluorine-containing polymer is used as a material for forming a pattern forming film with an ink-repellent/philic pattern in printed electronics.

In the case where a fluorine-containing polymer having a fluorine-containing acid-decomposable group is used as a pattern forming material common to photolithography and printed electronics, a film of the fluorine-containing polymer shows high water repellency before exposure to light but, after exposure to light, changes the properties of the light exposed portion from water repellency to hydrophilicity due to dissociation of the fluorine-containing acid-decomposable group.

In printed electronics, a film of pattern forming material is exposed to light through a patterned mask so that a water-repellent/hydrophilic pattern is formed with an unexposed water-repellent portion and an exposed hydrophilic portion by transfer of the mask pattern to the film. When an ink is applied to the water-repellent/hydrophilic pattern, the ink is rejected by the water-repellent portion whereby there is obtained a pattern of the ink.

For example, Patent Documents 1 and 2 each disclose a resin having a long-chain perfluoroalkyl group of 6 or more carbon atoms as a pattern forming material for printed electronics, which is capable of forming a high-definition, ink-spread-resistant pattern with ink-repellent and ink-philic portions by dissociation of the perfluoroalkyl group from the resin under light irradiation.

However, there is a fear that a resin having a long-chain perfluoroalkyl group is accumulated in the environment because this resin is difficult to burn or decompose. For example, the United States Environmental Protection Agency indicates the accumulation of perfluorooctanoic acid in the environment and thus demands the reduction of use of perfluorooctanoic acid. Accordingly, it is desired to avoid the use of fluorinated compounds having perfluoroalkyl groups of 6 or more carbon atoms from the viewpoint of accumulation of the fluorinated compounds in the environment.

Furthermore, there is known a polymer having a cyclic acetal skeleton in its acid-decomposable moiety as a polymer having an acid-decomposable group for use as a resist material in semiconductor manufacturing. Since the polymer having a cyclic acetal skeleton in the acid-decomposable moiety shows good acid dissociation properties, the development of such a polymer as an electronic material, in particular, as a radiosensitive patterning composition is being pursued.

For example, Patent Document 3 discloses a pattern forming method using a radiosensitive resin composition including a polymer containing a fluorine-free cyclic acetal monomer such as 2-tetrahydrofurfuryl methacrylate as an acid-decomposable monomer and a photoacid generator. Patent Document 4 discloses, as a pattern forming material having high sensitivity and high resolution and showing a high residual film rate during development, a positive photosensitive composition including a polymer, which is obtained by copolymerization of a monomer having a fluorine-free cyclic acetal group, a monomer having an acid-decomposable group or a monomer having a cross-linking group, and a radiosensitive acid generator.

Patent Document 5 discloses a fluorine-containing polymer having a cyclic hemiacetal structure and a fluorine-containing monomer as a precursor of the fluorine-containing polymer. Patent Document 6 discloses a fluorine-containing monomer having a cyclic hemiacetal structure modified with a substituent group such that, when the fluorine-containing monomer is polymerized, the water repellency, fat-solubility and acid decomposability of the fluorine-containing polymer can be controlled by selection of the substituent group.

PRIOR ART DOCUMENTS

Patent Documents

Patent Document 1: International Publication No. WO 2014/178279
Patent Document 2: Japanese Laid-Open Patent Publication No. 2016-87602
Patent Document 3: Japanese Laid-Open Patent Publication No. H4-26850
Patent Document 4: Japanese Laid-Open Patent Publication No. 2012-42837
Patent Document 5: Japanese Laid-Open Patent Publication No. 2006-152255
Patent Document 6: Japanese Laid-Open Patent Publication No. 2010-106138

SUMMARY OF THE INVENTION

Problems to be Solved by the Invention

One object of the present invention is to provide a fluorine-containing polymer having no perfluoroalkyl group of 4 or more carbon atoms, which, when formed together with a photoacid generator into a film in photoresist process or printed electronics, shows water repellency after film formation and before light exposure, but becomes hydrophilic after the light exposure by the action of an acid generated from the photoacid generator, so as to allow the film to exhibit a high contact angle with water before the light exposure and a low contact angle with water after the light exposure, and thus can be used in a pattern forming composition capable of forming a pattern with high sensitivity and high resolution.

Another object of the present invention is to provide a pattern forming composition containing the fluorine-containing polymer as a pattern forming material and a pattern forming method using the pattern forming composition. Still another object of the present invention is to provide a fluorine-containing monomer and a fluorine-containing compounds as precursors of the fluorine-containing polymer, and production methods thereof.

Means for Solving the Problems

As shown in Examples of the present specification, the present inventors newly synthesized a fluorine-containing polymer including the following repeating unit (1) (hereinafter also referred to as "fluorine-containing polymer (1)"), which contains an acid-decomposable group having a fluorine-containing cyclic acetal skeleton with a trifluoromethyl group bonded to a specific position thereof. The present inventors applied a pattern forming composition containing the fluorine-containing polymer (1) according to the present invention onto a substrate to form a film of the pattern forming composition.

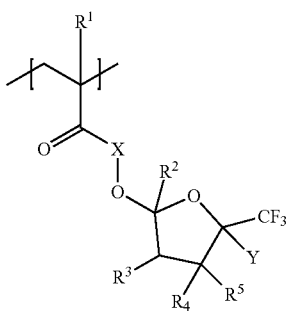

(1)

In the above formula, $R^1$ is a hydrogen atom, a fluorine atom or a $C_1$-$C_{10}$ linear alkyl group; $R^2$ to $R^5$ are each independently a hydrogen atom or a $C_1$-$C_{10}$ linear alkyl group; X is a single bond or a divalent group; Y is a $C_1$-$C_3$ fluoroalkyl or carboxylate (—COOR) group; and R is a $C_1$-$C_3$ fluoroalkyl group.

Further, the present inventors prepared pattern forming compositions respectively containing the fluorine-containing polymer (1) according to the present invention, a fluorine-containing polymer including the following repeating unit (A) as disclosed in Patent Document 6, a fluorine-containing polymer including the following repeating unit (B) as disclosed in Patent Document 3 and a fluorine-containing polymer having the following repeating unit (C) known as a general-purpose resist material, each together with a photoacid generator and a solvent, applied the pattern forming compositions onto substrate to form films of the pattern forming compositions, and cured the films by heating. Then, the present inventors found that the contact angle of the film containing the fluorine-containing polymer (1) with water was higher by about 10° than those of the film containing the fluorine-containing polymer with the repeating unit (A) and the film containing the fluorine-containing polymer with the repeating unit (B) (see Examples 1 to 7 and Comparative Examples 1 and 2 in TABLE 3). The present inventors also measured the sensitivity of the resist film containing the fluorine-containing polymer (1), the resist film containing the fluorine-containing polymer with the repeating unit (A) and the resist film containing the fluorine-containing polymer with the repeating unit (B) and found that the sensitivity of the resist film containing the fluorine-containing polymer (1) was higher than those of the resist film containing the copolymer with the repeating unit (A) and the resist film containing the copolymer with the repeating unit (B) (see Resists 1 to 3 and Comparative Resists 1 to 3 in TABLE 4). In view of the fact that the resist film containing the fluorine-containing polymer (1) was higher in sensitivity than the resist film containing the fluorine-containing polymer with the repeating unit (A), it is assumed that the fluorine-containing cyclic acetal structure of the fluorine-containing polymer (1) has higher acid decomposability than that of the fluorine-containing polymer with the repeating unit (A).

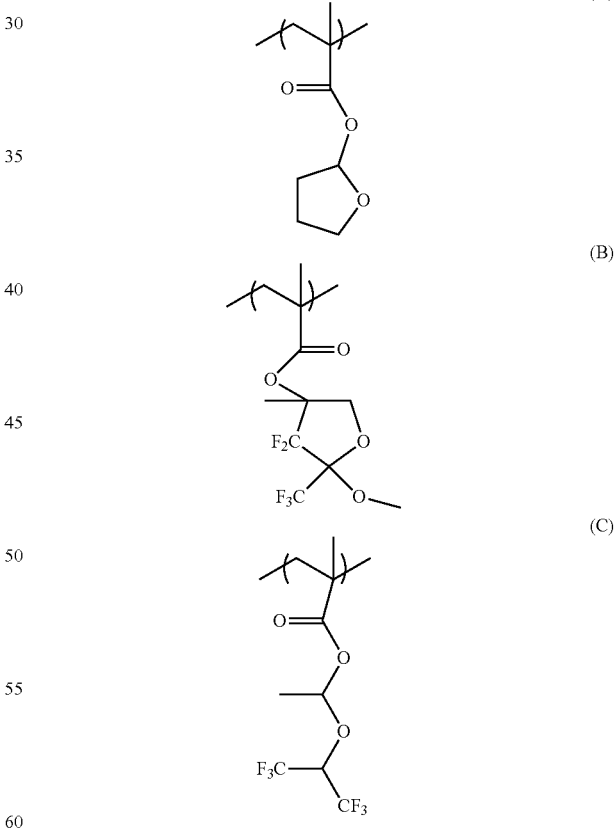

Subsequently, the present inventors subjected each of the above films to exposure to ultraviolet light through a photomask having a 30-nm line-and-space pattern and found that the pattern forming composition containing the fluorine-containing polymer (1) according to the present invention was higher in sensitivity and resolution that the other pattern forming compositions not according to the present invention (see Resists 1 to 3 and Comparative Resists 1 to 3 in TABLE 4).

As mentioned above, the present inventors confirmed that the newly synthesized fluorine-containing polymer having no perfluoroalkyl group of 4 or more carbon atoms, when formed together with a photoacid generator into a film in lithography or printed electronics, shows water repellency after the film formation and before the light exposure, but becomes hydrophilic after the light exposure by the action of an acid generated from the photoacid generator, so as to allow the film to exhibit a high contact angle with water before the light exposure and a low contact angle with water after the light exposure, and thus can be used in a pattern forming composition capable of forming a pattern with high sensitivity and high resolution.

In other words, the present invention includes the following aspects 1 to 16.

[Aspect 1]

A fluorine-containing polymer comprising a repeating unit of the following formula (1)

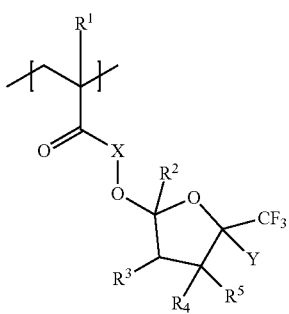

where $R^1$ is a hydrogen atom, a fluorine atom, or a $C_1$-$C_{10}$ linear or $C_3$-$C_{10}$ branched alkyl group in which seven or less of hydrogen atoms bonded to carbon atoms may be substituted with fluorine; $R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; X is a single bond, or a divalent group in which seven or less of hydrogen atoms may be substituted with fluorine; Y is a $C_1$-$C_3$ fluoroalkyl or carboxylate (—COOR) group in which seven or less of hydrogen atoms may be substituted with fluorine; and R is a $C_1$-$C_3$ fluoroalkyl group.

[Aspect 2]

The fluorine-containing polymer according to aspect 1, wherein $R^2$, $R^4$ and $R^5$ in the formula (1) are respectively hydrogen atoms.

[Aspect 3]

The fluorine-containing polymer according to aspect 2, wherein Y in the formula (1) is a trifluoromethyl group.

[Aspect 4]

A resist pattern forming composition comprising:
the fluorine-containing polymer according to any one of aspects 1 to 3;
an acid generator;
a basic compound; and
a solvent.

[Aspect 5]

A resist pattern forming method comprising:
a film forming step of forming a film of the resist pattern forming composition according to aspect 4 on a substrate;
an exposure step of subjecting the film to exposure to electromagnetic wave or high energy ray radiation of wavelength 300 nm or shorter through a photomask to thereby transfer a pattern of the photomask to the film; and
a development step of developing the film with a developer to obtain the pattern.

[Aspect 6]

An ink pattern forming composition comprising:
the fluorine-containing polymer according to any one of aspects 1 to 3;
an acid generator; and
a solvent.

[Aspect 7]

An ink pattern forming method comprising:
a film forming step of forming a film of the ink pattern forming composition according to aspect 6 on a substrate;
an exposure step of subjecting the film to exposure to light radiation of wavelength 150 to 500 nm through a photomask to transfer a pattern of the photomask to the film, thereby obtaining a pattern forming film with a liquid-repellent portion and a liquid-philic portion; and
a pattern forming step of applying an ink to the pattern forming film.

[Aspect 8]

An ink pattern forming method comprising:
a film forming step of forming a film of the ink pattern forming composition according to aspect 6 on a substrate and heating (prebaking) the film;
a drawing step of drawing a pattern on the film by subjecting the film to scanning 256 exposure to light radiation of wavelength 150 to 500 nm by means of drawing equipment, thereby obtaining a pattern forming film with a liquid-repellent portion and a liquid-philic portion; and
a pattern forming step of applying an ink to the pattern forming film.

[Aspect 9]

A fluorine-containing monomer of the following formula (4)

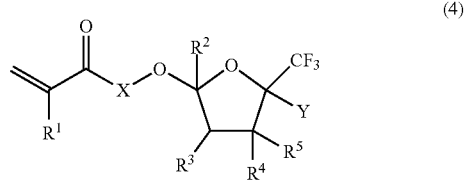

where $R^1$ is a hydrogen atom, a fluorine atom, or a $C_1$-$C_{10}$ linear or $C_3$-$C_{10}$ branched alkyl group in which seven or less of hydrogen atoms bonded to carbon atoms may be substituted with fluorine; $R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; X is a single bond, or a divalent group in which seven or less of hydrogen atoms may be substituted with fluorine; Y is a $C_1$-$C_3$ fluoroalkyl or carboxylate (—COOR) group in which seven or less of hydrogen atoms may be substituted with fluorine; and R is a $C_1$-$C_3$ fluoroalkyl group.

[Aspect 10]

The fluorine-containing monomer according to aspect 9, wherein $R^2$, $R^4$ and $R^5$ in the formula (4) are respectively hydrogen atoms.

[Aspect 11]

The fluorine-containing monomer according to aspect 10, wherein Y in the formula (4) is a trifluoromethyl group.

[Aspect 12]

A method for producing the fluorine-containing monomer of the formula (4) according to aspect 9, comprising:

forming a cyclic hemiacetal compound of the following formula (7) by cyclization of a hydroxycarbonyl compound of the following formula (10) or a hydroxyvinyl ether or hydroxyvinyl ester of the following formula (11)

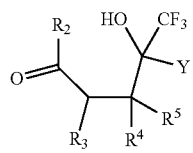

(10)

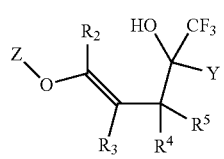

(11)

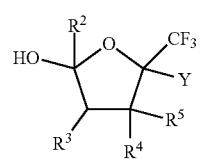

(7)

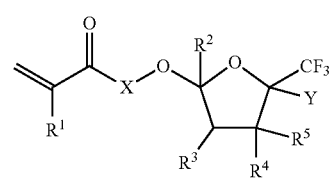

(4)

where $R^1$ is a hydrogen atom, a fluorine atom, or a $C_1$-$C_{10}$ linear or $C_3$-$C_{10}$ branched alkyl group in which seven or less of hydrogen atoms bonded to carbon atoms may be substituted with fluorine; $R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; X is a single bond, or a divalent group in which seven or less of hydrogen atoms may be substituted with fluorine; Y is a $C_1$-$C_3$ fluoroalkyl or carboxylate (—COOR) group in which seven or less of hydrogen atoms may be substituted with fluorine; R is a $C_1$-$C_3$ fluoroalkyl group; and Z is a hydrogen atom, or a $C_1$-$C_{20}$ liner or $C_3$-$C_{20}$ branched or cyclic alkyl group in which a part or all of hydrogen atoms may be substituted with fluorine and which may contain an ether bond, a siloxane bond, a thioether bond or a carbonyl bond.

[Aspect 13]

A fluorine-containing cyclic hemiacetal compound of the following formula (7)

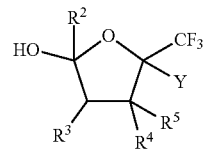

(7)

where $R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; Y is a $C_1$-$C_3$ fluoroalkyl or carboxylate (—COOR) group in which seven or less of hydrogen atoms may be substituted with fluorine; and R is a $C_1$-$C_3$ fluoroalkyl group.

[Aspect 14]

The fluorine-containing cyclic hemiacetal compound according to aspect 13, wherein $R^2$, $R^4$ and $R^5$ in the formula (7) are respectively hydrogen atoms.

[Aspect 15]

The fluorine-containing cyclic hemiacetal compound according to aspect 14, wherein Y in the formula (7) is a trifluoromethyl group.

[Aspect 16]

A method for producing the fluorine-containing cyclic hemiacetal compound of the formula (7) according to any one of aspects 13 to 15, comprising:

performing cyclization of a hydroxycarbonyl compound of the following formula (10) or a hydroxyvinyl ether or hydroxyvinyl ester of the following formula (11)

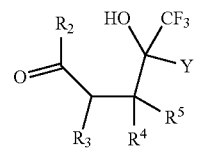

(10)

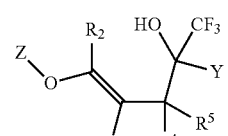

(11)

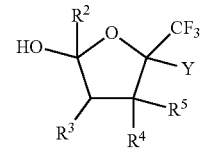

(7)

where $R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; Y is a $C_1$-$C_3$ fluoroalkyl or carboxylate (—COOR) group in which seven or less of hydrogen atoms may be substituted with fluorine; R is a $C_1$-$C_3$ fluoroalkyl group; and Z is a hydrogen atom, or a $C_1$-$C_{20}$ liner or $C_3$-$C_{20}$ branched or cyclic alkyl group in which a part or all of hydrogen atoms may be substituted with fluorine and which may contain an ether bond, a siloxane bond, a thioether bond or a carbonyl bond.

Effects of the Invention

According to the present invention, the fluorine-containing polymer is provided which does not have a perfluoroalkyl group of 4 or more carbon atoms and, when formed together with a photoacid generator into a film in photoresist process or printed electronics, shows water repellency after the film formation and before light exposure, but becomes hydrophilic after the light exposure by the action of an acid generated from the photoacid generator, so as to allow the film to exhibit a high contact angle with water before the light exposure and a low contact angle with water after the light exposure, and thus can be used in a pattern forming composition capable of forming a pattern with high sensitivity and high resolution. Further provided are the pattern forming composition containing the fluorine-containing polymer as a pattern forming material, the pattern forming method using the pattern forming composition, the fluorine-containing monomer and fluorine-containing compound usable as a precursor of the fluorine-containing polymer, and the production methods thereof.

The polymer according to the present invention has a fluorine-containing cyclic acetal skeleton with a perfluoroalkyl group of 1 to 3 carbon atoms, rather than a perfluoroalkyl group of 4 or more carbon atoms, and thus has no fear of being accumulated in the environment.

DETAILED DESCRIPTION OF THE EMBODIMENTS

Hereinafter, preferable embodiments of the present invention will be described below. It should be understood that: the present invention is not limited to the following embodiments; various changes and modification can be made to the following embodiments, based on the common knowledge of those skilled in the art, within the range that does not impair the effects of the present invention; and such changes and modifications are included in the scope of the present invention.

1. Fluorine-Containing Polymer

A fluorine-containing polymer according to the present invention has a fluorine-containing cyclic acetal structure with a repeating unit of the following formula (1). This polymer is hereinafter also referred to as "fluorine-containing polymer (1)".

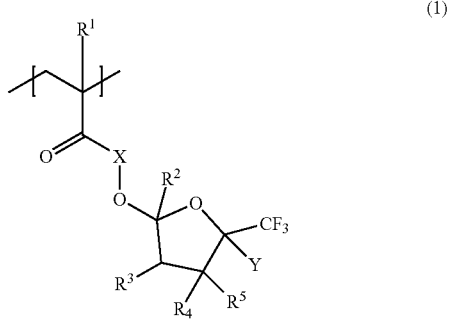

(1)

In the above formula (1), $R^1$ is a hydrogen atom, a fluorine atom, or a $C_1$-$C_{10}$ alkyl group; $R^2$ to $R^5$ are each independently a hydrogen atom, or a $C_1$-$C_{10}$ alkyl group; X is a single bond, or a divalent group; and Y is a $C_1$-$C_3$ fluoroalkyl or carboxylate (—COOR) group (where R is a $C_1$-$C_3$ fluoroalkyl group).

Explanations will be given of $R^1$, $R^2$, $R^3$, $R^4$, $R^5$, X and Y in the formula (1).

[$R^1$]

In the formula (1), $R^1$ is a hydrogen atom, a fluorine atom, or a $C_1$-$C_{10}$ linear or $C_3$-$C_{10}$ branched alkyl group in which seven or less of hydrogen atoms bonded to carbon atoms may be substituted with fluorine.

Specific examples of $R^1$ include hydrogen, methyl, ethyl, propyl, isopropyl, fluorine, trifluoromethyl, trifluoroethyl, trifluoropropyl, 1,1,1,3,3,3-hexafluoroisopropyl (—C(CF$_3$)$_2$H) and heptafluoroisopropyl. For ease of polymerization, $R^1$ is preferably hydrogen, fluorine or methyl.

[$R^2$ to $R^5$]

$R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine.

For ease of synthesis, an electron-donating alkyl group is more preferred than an electron-attracting group as $R^2$ to $R^5$. $R^2$ to $R^5$ are preferably hydrogen or methyl, each of which has no steric hindrance.

[X]

X is a single bond, or a divalent group in which seven or less of hydrogen atoms may be substituted with fluorine.

The divalent bond as X is preferably of 2 to 10 carbon atoms. Examples of the divalent group include a methylene group, a $C_2$-$C_{10}$ alkylene group, a $C_2$-$C_{10}$ alkenylene group, a $C_6$-$C_{10}$ aryl group and a $C_4$-$C_{10}$ divalent alicyclic hydrocarbon group. The alkylene group and the alkenylene group may each have an ether (—O—) bond, a carbonyl group (—C=O—) or a carboxyl group (—(C=O)O— or —O(C=O)—). When the divalent group has a long chain, the liquid repellency of the polymer may be lowered. For this reason, X is preferably a single bond, an oxyethylene (—O—CH$_2$—CH$_2$—) group or an oxyacetil (—O—CH$_2$—CO—) group.

[Y]

Y is a $C_1$-$C_3$ fluoroalkyl or carboxylate (—COOR) group (where R is a $C_1$-$C_3$ fluoroalkyl group) in which seven or less of hydrogen atoms may be substituted with fluorine.

Specific examples of Y include trifluoromethyl, trifluoroethyl, pentafluoroethyl, trifluoropropyl, 1,1,1,3,3,3-hexafluoroisopropyl and heptafluoroisopropyl. For ease of synthesis, Y is preferably trifluoromethyl, trifluoroethyl or 1,1,1,3,3,3-hexafluoroisopropyl.

The fluorine-containing polymer (1) according to the present invention may have an asymmetric carbon atom in the molecule depending on the kinds and combination of the above substituent groups. The fluorine-containing polymer (1) can thus exist as enantiomers (i.e. stereoisomers that are mirror images of each other) or diastereoisomers (i.e. stereoisomers that have two or more asymmetric carbon atoms in the respective molecules and are not mirror images of each other). Herein, the formula (1) is representative of all of these stereoisomers. The stereoisomers can be used solely or in the form of a mixture thereof.

[Fluorine-Containing Polymer (2)]

In the present invention, the fluorine-containing polymer (1) is preferably a fluorine-containing polymer with a repeating unit of the following formula (2) corresponding to the case where $R^2$, $R^4$ and $R^5$ in the formula (1) are respectively hydrogen atoms. In order for the fluorine-containing polymer (1) to be soluble in a solvent such that the resulting pattern forming composition can be formed into a film on a substrate, it is preferable that $R^2$, $R^4$ and $R^5$ in the formula (1) are respectively hydrogen atoms. In other words, a polymer having a fluorine-containing cyclic acetal structure with a repeating unit of the following formula (2) is preferred in the present invention. This polymer is hereinafter also referred to as "fluorine-containing polymer (2)".

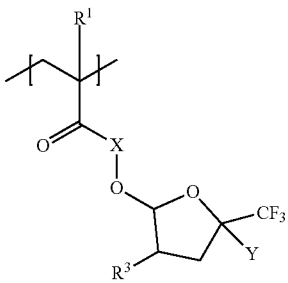

(2)

In the above formula (2), $R^1$, $R^3$, X and Y have the same definitions as those in the formula (1).

[Fluorine-Containing Polymer (3)]

The fluorine-containing polymer (1) is further preferably a fluorine-containing polymer with a repeating unit of the following formula (3) corresponding to the case where Y in the formula (1) is a trifluoromethyl group. It is preferable that Y in the formula (1) is a trifluoromethyl group in order to ensure the solvent solubility of the polymer. In other words, a polymer having a fluorine-containing cyclic acetal structure with a repeating unit of the following formula (3) is preferred. This polymer is hereinafter also referred to as "fluorine-containing polymer (3)".

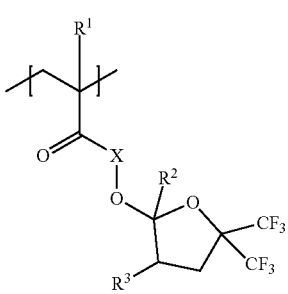

(3)

In the above formula (3), $R^1$, $R^3$ and X have the same definitions as those in the formula (1).

1-1. Decomposition of Fluorine-Containing Polymer (1) by Acid

It is known that, as in the case of an ordinary acetal, a cyclic acetal structure is decomposed by an acid. Similarly, the fluorine-containing cyclic acetal structure of the fluorine-containing polymer (1) according to the present invention is supposed to undergo the following decomposition reaction.

Two reaction paths are conceivable for the decomposition reaction of the fluorine-containing polymer (1) by an acid as shown below. In one reaction path, an acid-decomposable group (1B) is dissociated from the fluorine-containing polymer (1) whereby a repeating unit of the formula (1A) remains in the polymer. In the other reaction path, a repeating unit of the formula (1C) is generated by ring-opening of the fluorine-containing cyclic acetal structure. It is thus assumed that, as the hydrophilic fluorine-containing polymer with the repeating unit of the formula (1A) or (1C) is formed from the water-repellent fluorine-containing polymer (1), the contact angle of an ink with the film is decreased so that the pattern forming function of the ink is expressed.

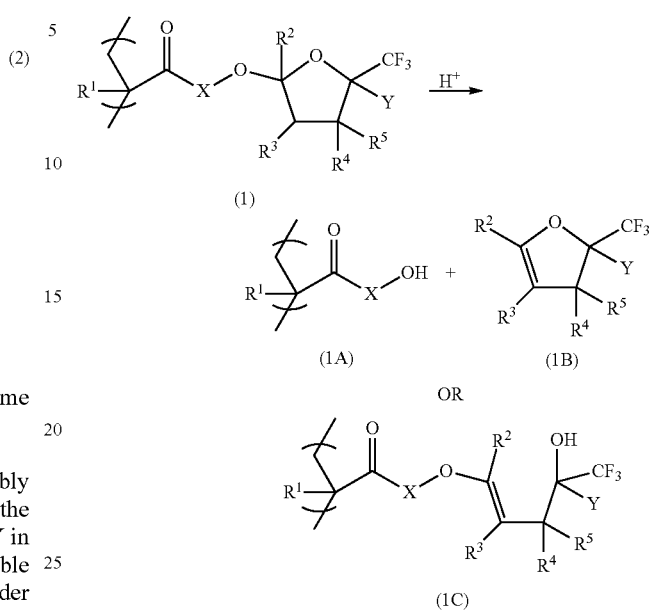

1-2. Monomer as Other Repeating Unit

The fluorine-containing polymer (1) according to the present invention may include any repeating unit other than the repeating unit (1). The repeating unit other than the repeating unit (1) is included in the fluorine-containing polymer (1) for the purpose of, at the time when the pattern forming composition containing the fluorine-containing polymer (1) is formed into a film, adjusting the solvent solubility of the fluorine-containing polymer (1) or adjusting the hardness of the film.

The fluorine-containing polymer (1) with the repeating unit (1) and the other repeating unit is obtained by copolymerization of a fluorine-containing monomer (4) corresponding to the repeating unit (1) and a monomer corresponding to the other repeating unit.

The monomer corresponding to the other repeating unit can be of any kind having a polymerizable unsaturated bond and being copolymerizable with the fluorine-containing monomer (4) corresponding to the repeating unit (1). Examples of the monomer corresponding to the other repeating unit include an adhesive group-containing monomer, an acrylic ester, a fluorine-containing acrylic ester, a methacrylic ester, a fluorine-containing methacrylic ester, a hexafluoroisopropanol (—C(CF$_3$)$_2$OH; also referred to as "HFIP)-containing monomer, a styrene, a fluorine-containing styrene, a vinyl ether, an allyl ether, a fluorine-containing vinyl ether, a fluorine-containing allyl ether, an olefin, a fluorine-containing olefin, a norbornene, a fluorine-containing norbornene, and any other monomer with a polymerizable unsaturated bond.

[Adhesive Group-Containing Monomer]

In the case of using the fluorine-containing polymer (1) as a resist component, the fluorine-containing polymer (1) attains good adhesion to substrate in lithography by introduction of an adhesive group into the chemical structure of the fluorine-containing polymer. As the adhesive group, there can be used a lactone structure-containing group.

For introduction of the adhesive group into the fluorine-containing polymer (1), it is feasible to use a monomer copolymerizable with the fluorine-containing monomer (4) and having a monocyclic or polycyclic lactone structure.

The monocyclic lactone structure can be a group having a bond resulting from elimination of one hydrogen atom from γ-butyrolactone or mevaloniclactone. The polycyclic lactone structure can be a group having a bond resulting from elimination of one hydrogen atom from norbornane lactone. The lactone structure can be introduced into the fluorine-containing polymer (1) by copolymerization of a lactone structure-containing acrylic ester or methacrylic ester. In this case, the fluorine-containing polymer (1), when used as a resist component in lithography, attains not only improvement in substrate adhesion but also improvement in developer compatibility.

The following are examples of the repeating unit that allows the polymer to exhibit substrate adhesion when formed into a resist film.

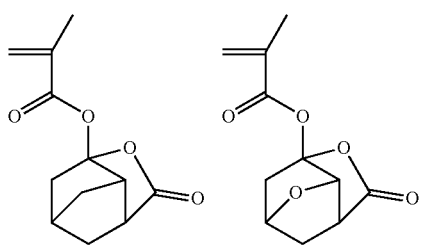

MNLA

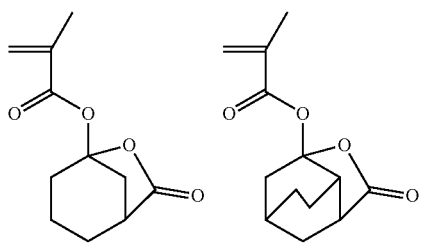

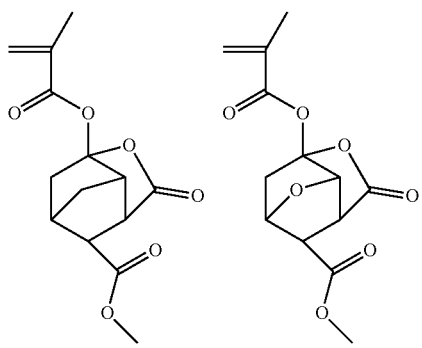

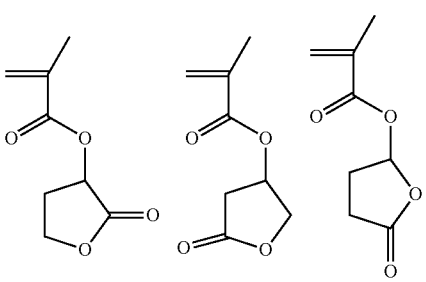

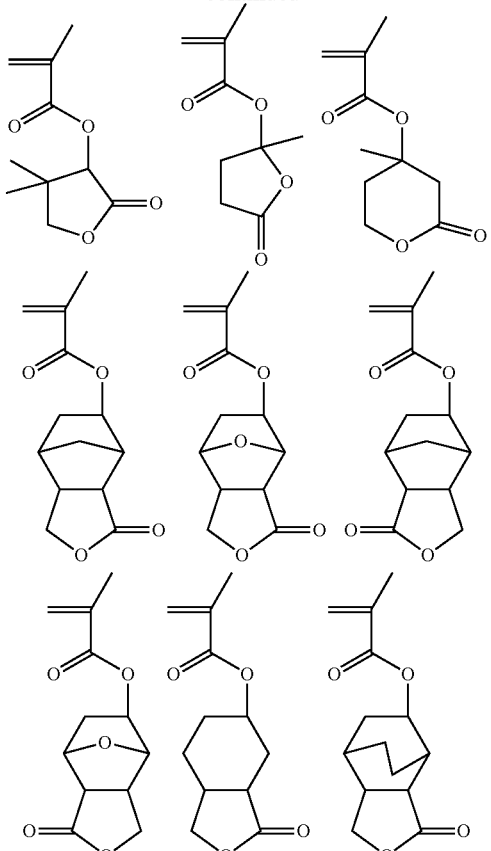

For ease of availability, particularly preferred is 5-methacryloyloxy-2,6-norbornanecarbolactone (hereinafter also referred to as "MNLA"). This structure is shown as MNLA in the above paragraph.

[Acrylic Ester]

Examples of the acrylic ester include methyl acrylate, ethyl acrylate, n-propyl acrylate, isopropyl acrylate, n-butyl acrylate, isobutyl acrylate, n-hexyl acrylate, n-octyl acrylate, 2-ethylhexyl acrylate, lauryl acrylate, 2-hydroxyethyl acrylate, 2-hydroxypropyl acrylate, acrylate containing ethylene glycol, propylene glycol or tetramethylene glycol, acrylamide, N-methylol acrylamide or diacetone acrylamide as unsaturated amide, tert-butyl acrylate, 3-oxocyclohexyl acrylate, adamantyl acrylate, methyladamantyl acrylate, ethyladamantyl acrylate, hydroxyadamantyl acrylate, cyclohexyl acrylate, tricyclodecanyl acrylate, acrylate having a ring structure such as lactone ring, norbornene ring or the like, and those having a cyano group in the or α-position.

[Fluorine-Containing Acrylic Ester]

As the fluorine-containing acrylic ester, there can be used those having a fluorine-containing organic group in the or α-position relative to the acrylic moiety or in the ester moiety thereof. The fluorine-containing acrylic ester may have fluorine-containing organic groups in both of the α-position and the ester moiety, or may have a cyano group in the α-position and a fluoroalkyl group in the ester moiety.

The fluorine-containing organic group contained in the α-position of the fluorine-containing acrylic ester can be a trifluoromethyl group, a trifluoroethyl group or a nonafluoro-n-butyl group.

The fluorine-containing organic group contained in the ester moiety of the fluorine-containing acrylic ester can be a perfluoroalkyl group, a fluoroalkyl group having a hydrogen atom, or a group having a fluorine-containing benzene ring, fluorine-containing cyclopentane ring, fluorine-containing cyclohexane ring or fluorine-containing cycloheptane ring in which a hydrogen atom on the ring structure has been substituted with a fluorine atom, a trifluoromethyl group, a HFIP group or the like.

Examples of the fluorine-containing acrylic ester include 2,2,2-trifluoroethyl acrylate, 2,2,3,3-tetrafluoropropyl acrylate, 1,1,1,3,3,3-hexafluoroisopropyl acrylate, heptafluoroisopropyl acrylate, 1,1-dihydroheptafluoro-n-butyl acrylate, 1,1,5-trihydrooctafluoro-n-pentyl acrylate, 1,1,2,2-tetrahydrotridecafluoro-n-octyl acrylate, 1,1,2,2-tetrahydroheptadecafluoro-n-decyl acrylate, 6-[3,3,3-trifluoro-2-hydroxy-2-(trifluoromethyl)propyl]bicyclo[2.2.1]heptyl-2-yl acrylate, 6-[3,3,3-trifluoro-2-hydroxy-2-(trifluoromethyl)propyl]bicyclo[2.2.1]heptyl-2-yl 2-(trifluorometyl)acrylate, 1,4-bis(1,1,1,3,3,3-hexafluoro-2-hydroxyiropropyl)cyclohexyl acrylate and 1,4-bis(1,1,1,3,3,3-hexafluoro-2-hydroxyisopropyl)cyclohexyl-2-trifluoromethyl acrylate.

[Methacrylic Ester]

Examples of the methacrylic ester include methyl methacrylate, ethyl methacrylate, n-propyl methacrylate, isopropyl methacrylate, n-butyl methacrylate, isobutyl methacrylate, n-hexyl methacrylate, n-octyl methacrylate, 2-ethylhexyl methacrylate, lauryl methacrylate, 2-hydroxyethyl methacrylate, 2-hydroxypropyl methacrylate, methacrylate containing ethylene glycol, propylene glycol or tetramethylene glycol, methacrylamide, N-methylol methaacrylamide or diacetone methacrylamide as unsaturated amide, tert-butyl methacrylate, 3-oxocyclohexyl methacrylate, adamantyl methacrylate, methyladamantyl methacrylate, ethyladamantyl methacrylate, hydroxyadamantyl methacrylate, cyclohexyl methacrylate, tricyclodecanyl methacrylate, and acrylate having a ring structure such as lactone ring, norbornene ring or the like.

[Fluorine-Containing Methacrylic Ester]

As the fluorine-containing methacrylic ester, there can be used those having a fluorine-containing organic group in the ester moiety thereof.

The fluorine-containing organic group can be a perfluoroalkyl group, a fluoroalkyl group having a hydrogen atom, or a group having a fluorine-containing benzene ring, fluorine-containing cyclopentane ring, fluorine-containing cyclohexane ring or fluorine-containing cycloheptane ring in which a hydrogen atom on the ring structure has been substituted with a fluorine atom, a trifluoromethyl group, a HFIP group or the like.

Examples of the fluorine-containing methacrylic ester include 2,2,2-trifluoroethyl methacrylate, 2,2,3,3-tetrafluoropropyl methacrylate, 1,1,1,3,3,3-hexafluoroisopropyl methacrylate, heptafluoroisopropyl methacrylate, 1,1-dihydroheptafluoro-n-butyl methacrylate, 1,1,5-trihydrooctafluoro-n-pentyl methacrylate, 1,1,2,2-tetrahydrotridecafluoro-n-octyl methacrylate, 1,1,2,2-tetrahydroheptadecafluoro-n-decyl methacrylate, perfluorocyclohexylmethyl methacrylate, perfluorocyclohexylmethyl methacrylate, 6-[3,3,3-trifluoro-2-hydroxy-2-(trifluoromethyl)propyl]bicyclo[2.2.1]heptyl-2-yl methacrylate and 1,4-bis(1,1,1,3,3,3-hexafluoro-2-hydroxyisopropyl)cyclohexyl methacrylate.

[HFIP-Containing Monomer]

Examples of the HFIP-containing monomer include those shown below.

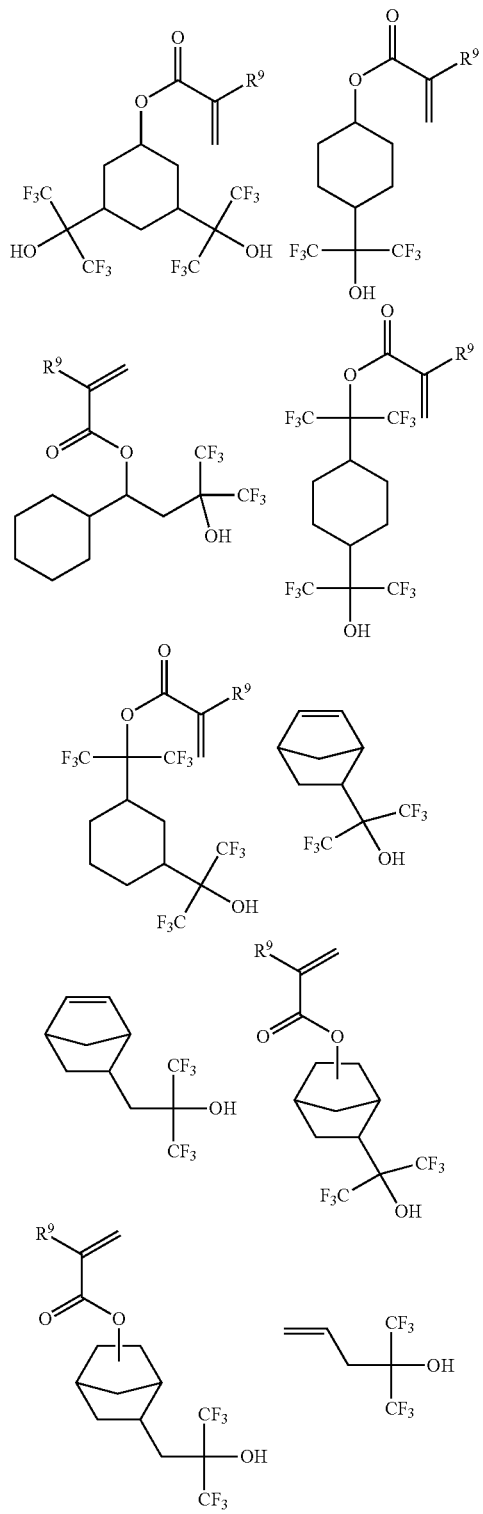

In the above formulas, $R^9$ is a hydrogen atom, a methyl group, a fluorine atom or a trifluoromethyl group; and the HFIP group may be partially or entirely protected with a protecting group.

[Styrene and Fluorine-Containing Styrene]

Examples of the styrene include styrene and hydroxystyrene.

Examples of the fluorine-containing styrene include pentafluorostyrene, (trifluoromethyl)styrene, bis(trifluoromethyl)styrene, a styrene in which a hydrogen atom on the aromatic ring structure has been substituted with a fluorine atom or a trifluoromethyl group, a styrene in which a hydrogen atom on the aromatic ring structure has been substituted with a HFIP group or a hydroxy-protected HFIP group, a styrene having a halogen atom, an alkyl group or a fluoroalkyl group bonded to its α-position, or a perfluorovinyl-containing styrene.

[Vinyl Ether, Allyl Ether, Fluorine-Containing Vinyl Ether and Fluorine-Containing Allyl Ether]

Examples of the vinyl ether and the allyl ether include those having a methyl group, ethyl group, n-propyl group, iso-propyl group, n-butyl group, iso-butyl group, sec-butyl group, t-butyl group, hydroxyethyl group and hydroxybutyl group. The vinyl ether and the allyl ether can be an alkyl vinyl ether and an alkyl allyl ether, respectively. In the case of the vinyl ether having a hydroxyethyl or hydroxybutyl group, the alcohol moiety may form an ester bond with an acetyl group, butyloyl group or propionyl group. Cyclic vinyl ethers and cyclic allyl ethers each having a cyclopentyl group, cyclohexyl group, norbornyl group, aromatic ring or hydrogen- or carbonyl-containing ring structure are also examples of the vinyl ether and the allyl ether. Examples of the fluorine-containing vinyl ether and the fluorine-containing allyl ether include those obtained by substituting a part or all of hydrogen atoms of the above vinyl ether and allyl ether with fluorine.

[Olefin and Fluorine-Containing Olefin]

Examples of the olefin include ethylene, propylene, isobutene, cyclopentene and cyclohexene. Examples of the fluorine-containing olefin are vinyl fluoride, vinylidene fluoride, trifluoroethylene, chlorotrifluoroethylene, tetrafluoroethylene, hexafluoropropylene, hexafluoroisobutene, 1-chloro-2,3,3,4,4,5,5-heptafluorocyclopentene, octafluorocyclopentene and decafluorocyclohexene.

[Norbornene and Fluorine-Containing Norbornene]

The norbornene and fluorine-containing norbornene can be of any kind having a polymerizable group. The norbornene and fluorine-containing norbornene may each have one norbornene skeleton or a plurality of norbornene skeletons. Examples of the norbornene and the fluorine-containing norbornene include those obtained by Diels-Alder addition reaction of an unsaturated compound and a diene compound.

As the unsaturated compound, there can be used a fluorine-containing olefin, an allyl alcohol, a fluorine-containing allyl alcohol, a homoallylic alcohol, a fluorine-containing a homoallylic alcohol, an acrylic acid, an α-fluoroacrylic acid, an α-trifluoromethyl acrylic acid, a methacrylic acid, any of the above-mentioned acrylic ester, methacrylic ester, fluorine-containing acrylic ester and fluorine-containing methacrylic ester, 2-(benzoyloxy)pentafluoropropane, 2-(methoxyethoxymethyloxy)pentafluoropropane, 2-(tetrahydroxypyranyloxy)pentafluoropropane, 2-(benzoyloxy)trifluoroethylene, 2-(methoxymethyloxy)trifluoroethylene or the like. As the diene compound, there can be used cyclopentadiene, cyclohexadiene or the like.

Examples of the fluorine-containing norbornene include 3-(5-bicyclo[2.2.1]heptane-2-yl)-1,1,1,1-trifluoro-2-(trifluoromethyl)-2-propanol.

[Other Monomer with Polymerizable Unsaturated Bond]

Examples of the other monomer with a polymerizable unsaturated bond include acrylic acid, methacrylic acid, maleic acid, fumaric acid and maleic anhydride.

In the case where the other monomer has a long-chain organic group from the polymerization site and in the case where the other monomer has an organic group with many hetero atoms, the influence of the organic group of the other monomer becomes strong so that there may occur a decrease in the liquid repellency imparting effect of the terminal fluoroalkyl group or in the solubility of the polymer. For this reason, the other monomer is preferably an acrylic or methacrylic ester of less than 10 carbon atoms. Particularly preferred are methyl methacrylate, ethyl methacrylate, n-propyl methacrylate, isopropyl methacrylate, n-butyl methacrylate and isobutyl methacrylate.

1-3. Content of Each Repeating Unit in Fluorine-Containing Polymer (1)

The content of the repeating unit of the formula (4) is preferably in the range of 10 mol % to 100 mol %, more preferably 10 mol % to 90 mol %, based on the total amount of the fluorine-containing polymer (1). When the content of the repeating unit (1) in the fluorine-containing polymer (1) is lower than 10 mol %, the pattern forming film obtained by exposure of the fluorine-containing polymer (1) does not render its unexposed portion water repellent.

The content of the repeating unit derived from the other monomer is preferably in the range of 0 mol % to 90 mol %, more preferably 10 mol % to 90 mol %, based on the total amount of the fluorine-containing polymer (1).

The repeating unit derived from the other monomer is used to improve the solubility of the fluorine-containing polymer (1) in an organic solvent and, at the time when a film is formed from the fluorine-containing polymer (1), to improve the surface adhesion or hardness of the film as mentioned above. The repeating unit derived from the other monomer may not be used if unnecessary. When the content of the repeating unit derived from the other monomer is lower than 10 mol %, however, the substrate adhesion or hardness of the film may not be sufficiently improved. When the content of the repeating unit derived from the other monomer exceeds 90 mol %, the content of the repeating unit (1) becomes low so that the pattern forming film obtained by exposure of the film of the fluorine-containing polymer (1) does not render its unexposed portion water repellent while maintaining its exposed portion hydrophilic.

1-4. Molecular Weight of Fluorine-Containing Polymer (1)

In the present invention, the number-average molecular weight of the fluorine-containing polymer (1) is generally in the range of 1,000 to 100,000, preferably 3,000 to 50,000. Further, the molecular weight dispersity of the fluorine-containing polymer (1) is generally in the range of 1 to 4, preferably 1 to 2.5. When the number-average molecular weight of the fluorine-containing polymer (1) is smaller than 1,000, a film of the pattern forming composition containing the fluorine-containing polymer (1) may become soft and become difficult to form with a desired thickness. It may also become difficult that the pattern forming film obtained after the exposure provides a fine pattern with liquid-repellent and liquid-philic portions. In addition, the pattern may become poor in durability. When the number-average molecular weight of the fluorine-containing polymer (1) is greater than 100,000, it becomes difficult to dissolve the fluorine-containing polymer (1) in a solvent and thereby becomes difficult to form a coating film of the pattern forming composition containing the fluorine-containing polymer (1) due to the occurrence of cracking.

2. Synthesis of Fluorine-Containing Polymer

[Synthesis of Fluorine-Containing Polymer (1)]

It is feasible to synthesize the fluorine-containing polymer (1) by an ordinary polymerization process. Among others, a radical polymerization process or ion polymerization process is preferred. In some cases, a coordination anionic polymerization process, living anionic polymerization process or cationic polymerization process may be selected. There is no particular limitation on the reactor used for the polymerization reaction. A polymerization solvent may be used in the polymerization reaction. Hereinafter, an explanation will be given of the radical polymerization.

The radical polymerization is conducted in the presence of a radical polymerization initiator or radical initiating source by a known polymerization method such as bulk polymerization, solution polymerization, suspension polymerization, emulsion polymerization etc. in a batch system, semi-continuous system or continuous system.

<Radical Polymerization Initiator>

As the radical polymerization initiator, there can be used an azo compound, a peroxide compound or a redox compound.

Examples of the azo compound include azobis(isobutyronitrile). Examples of the peroxide compound include t-butyl peroxypivalate, di-t-butyl peroxide, i-butyryl peroxide, lauroyl peroxide, succinic acid peroxide, dicinnamyl peroxide, d-n-propyl peroxydicarbonate, t-butyl peroxyallylmonocarbonate, benzoyl peroxide, hydrogen peroxide and ammonium persulfate.

<Polymerization Solvent>

The polymerization solvent is preferably of the kind that does not interfere with the radical polymerization. As the polymerization solvent, there can be used an ester solvent, a ketone solvent, a hydrocarbon solvent or an alcohol solvent. Water, an ether solvent, a cyclic ether solvent, a fluorocarbon solvent or an aromatic solvent may alternatively be used as the polymerization solvent.

Examples of the polymerization solvent include: ester solvents such as ethyl acetate and n-butyl acetate; ketone solvents such as acetone and methyl isobutyl ketone; hydrocarbon solvents such as toluene and cyclohexane; and alcohol solvents such as ethanol, isopropyl alcohol and ethylene glycol monomethyl ether.

The above polymerization solvents can be used solely or in combination of two kinds or more thereof. A molecular weight modifier such as mercaptan may be used in combination.

<Polymerization Conditions>

The polymerization temperature can be set as appropriate depending on the kind of the radical polymerization initiator or radical initiating source. It is desirable to select the kind of the radical polymerization initiator or radical initiating source such that the polymerization temperature is in the range of 20° C. to 200° C., preferably 30° C. to 140° C. The molecular weight of the fluorine-containing polymer (1) can be controlled by appropriately selecting the radical polymerization initiator or radical initiating source and adjusting the polymerization conditions.

After the polymerization, the polymerization solvent such as organic solvent or water can be removed from the solution or dispersion containing the fluorine-containing polymer (1) by a known method such as reprecipitation, filtration, heating distillation under reduced pressure, or the like.

In the case of using the fluorine-containing polymer (1) as a resist component, the conditions for patterning in lithography varies as the developer solubility of the fluorine-containing polymer (1) changes according to the molecular weight of the fluorine-containing polymer (1). When the molecular weight of the fluorine-containing polymer (1) is great, the dissolution rate of the fluorine-containing polymer (1) in the developer tends to be low. The dissolution rate of the fluorine-containing polymer (1) in the developer tends to be high when the molecular weight of the fluorine-containing polymer (1) is small. As mentioned above, the molecular weight of the fluorine-containing polymer (1) can be controlled by adjusting the polymerization conditions.

3. Resist Pattern Forming Composition

A resist pattern forming composition according to the present invention is prepared by adding an acid generator, a basic compound and a solvent to any of the fluorine-containing polymers (1) to (3), and can be used for lithography. Hereinafter, the resist pattern forming composition is also simply referred to as "resist".

Each of the fluorine-containing polymers (1) to (3) according to the present invention is suitably usable as a chemically amplified positive resist component. In other words, the resist according to the present invention is provided as a chemically amplified positive resist material containing any of the fluorine-containing polymers (1) to (3).

In the present invention, the resist preferably contains the following components: (A) any of the fluorine-containing polymers (1) to (3); (B) a photoacid generator; (C) a basic compound; (D) a solvent; and optionally (E) a surfactant.

3-1. (B) Photoacid Generator

In the present invention, there is no particular limitation on the photoacid generator used in the resist. It is feasible to select and use any arbitrary one of photoacid generators for chemically amplified resists. As the photoacid generator, there can be used an onium sulfonate salt or a sulfonic acid ester. Examples of the photoacid generator include iodonium sulfonate, sulfonium sulfonate, N-imide sulfonate, N-oxime sulfonate, o-nitrobenzyl sulfonate, trimethanesulfonate of pyrogallol, and the like.

In lithography, an acid generated from the photoacid generator by exposure to light. The thus-generated acid is an alkanesulfonic acid, an aryl sulfonic acid, a partially or completely fluorinated aryl sulfonic acid or alkanesulfonic acid, or the like. Among others, preferred is a photoacid generator capable of generating a partially or completely fluorinated alkanesulfonic acid. Specific examples of such a photoacid generator include triphenylsulfonium trifluoromethanesulfonate and triphenylsulfonium perfluoro-n-butanesulfonate.

3-2. (C) Basic Compound

The basic compound is added to the resist containing any one of the fluorine-containing polymers (1) to (3). The basic compound has the function of, when the acid is generated from the photoacid generator, decreasing the diffusion rate of the acid in the resist film. Further, it is expected that the addition of the basic compound leads to improvement in the shape of the resist pattern by control of the diffusion distance of the acid as well as stability improvement for the formation of the resist pattern with desired precision even in the case where the time lapsed until the exposure of the resist film is long.

As the basic compound, there can be used an aliphatic amine, an aromatic amine, a heterocyclic amine, an aliphatic polycyclic amine or the like. Among these amines, a secondary or tertiary aliphatic amine and an alkyl alcohol amine are preferred. Examples of the basic compound are trimethylamine, triethylamine, tripropylamine, tributylamine, tripentylamine, trihexylamine, triheptylamine, trioctylamine, trinonylamine, tridecanylamine, tridodecylamine, dimethyl-amine, diethylamine, dipropylamine, dibutylamine, dipentylamine, dihexylamine, diheptylamine, dioxtylamine, dinonylamine, didecanylamine, didodecylamine, dicyclohexylamine, methylamine, ethylamine, propylamine, butylamine, pentylamine, hexylamine, heptylamine, octylamine, nonylamine, decanylamine, dodecylamine, diethanolamine, triethanolamine, diisopropanolamine, triisopropanolamine, dioctanolamine, trioctanolamine, aniline, pyridine, picoline, lutidine, bipyridine, pyrrole, piperidine, piperazine, indole, and hexamethylenetetramine. These basic compounds can be used solely or in combination of two or more kinds thereof.

The content of the basic compound in the resist is generally in the range of 0.001 to 2 parts by mass, preferably 0.01 to 1 part by mass, per 100 parts by mass of the fluorine-containing polymer (1). When the content of the basic compound is lower than 0.01 parts by mass, the sufficient effect of the basic compound as the additive may not obtained. When the content of the basic compound exceeds 2 parts by mass, the resolution and sensitivity of the resist may be lowered.

3-3. (D) Solvent

The solvent (D) is contained in the resist in addition to any of the fluorine-containing polymers (1) to (3) as the polymer component (A), the photoacid generator (B) and the basic compound (C). The solvent can be of any kind capable of dissolving the resist components such as any of the fluorine-containing polymers (1) to (3) as the polymer component (A), the photoacid generator (B) and the basic compound (C) to form a uniform solution. It is feasible to select and use any one of conventional resist solvents. Two or more kinds of solvents may be used in the form of a mixture.

As such a solvent, there can be used a ketone, an alcohol, a polyalcohol, an ester, an aromatic solvent, an ether or a fluorinated solvent. A high-boiling solvent such as terpene-based petroleum naphtha solvent or paraffin solvent may alternatively be used for improvement of applicability.

Examples of the solvent includes: ketone solvents such as acetone, methyl ethyl ketone, cyclopentanone, cyclohexanone, methyl isobutyl ketone, methyl isopentyl ketone and 2-heptanone; alcohol solvents such as isopropanol, butanol, isobutanol, n-pentanol, isopentanol, tert-pentanol, 4-methyl-2-pentanol, 3-methyl-3-pentanol, 2,3-dimethyl-2-pentanol, n-hexanol, n-heptanol, 2-heptanol, n-octanol, n-decanol, s-amyl alcohol, t-amyl alcohol, isoamyl alcohol, 2-ethyl-1-butanol, lauryl alcohol, hexyldecanol and oleyl alcohol; polyalcohols such as ethylene glycol, diethylene glycol, propylene glycol, dipropylene glycol, ethylene glycol monoacetate, diethylene glycol monoacetate, propylene glycol monoacetate, dipropylene glycol monoacetate, propylene glycol monomethyl ether, propylene glycol monoethyl ether, propylene glycol monopropyl ether, propylene glycol monobutyl ether, propylene glycol monomethyl ether acetate (PGMEA) and propylene glycol monomethyl ether (PGME); derivatives of the polyalcohols; ester solvents such as methyl lactate, ethyl lactate (EL), methyl acetate, ethyl acetate, butyl acetate, methyl pyruvate, ethyl pyruvate, methyl methoxypropionate, ethyl ethoxypropionate; aromatic solvents such as toluene and xylene; ether solvents such as diethyl ether, dioxane, anisole and diisopropyl ether; and fluorinated solvents such as hexafluoroisopropyl alcohol.

Among others, propylene glycol monomethyl ether acetate (PGMEA), propylene glycol monomethyl ether (PGME), cyclohexanone, ethyl lactate (EL) are preferred for use in the resist.

There is no particular limitation on the content of the solvent in the resist. It is desirable to adjust the content of the solvent such that the concentration of solid matter in the resist is preferably in the range of 3 mass % to 25 mass %, more preferably 5 mass % to 15 mass %. The thickness of the resulting resist film can be controlled by adjusting the solid matter concentration of the resist.

Each of the fluorine-containing polymers (1) to (3) has a high solubility in a wide range of solvents. It is worthy of special note that, among the above alcohol solvents, the fluorine-containing polymer is soluble in a $C_5$-$C_{20}$ alcohol solvent. Examples of such an alcohol solvent are n-pentanol, isopentanol, tert-pentanol, 4-methyl-2-pentanol, 3-methyl-3-pentanol, 2,3-dimethyl-2-pentanol, n-hexanol, n-heptanol, 2-heptanol, n-octanol, n-decanol, s-amyl alcohol, t-amyl alcohol, isoamyl alcohol, 2-ethyl-1-butanol, lauryl alcohol, hexyldecanol and oleyl alcohol.

3-4. (E) Surfactant

The surfactant is optionally added to the resist as required. As the surfactant, there can be used a fluorine-based surfactant, a silicon-based surfactant or a surfactant containing both of fluorine and silicon. Two or more kinds of surfactants may be used in combination.

3-5. Resist

The resist according to the present invention is soluble in a $C_5$-$C_{20}$ alcohol solvent etc., in which conventional resist materials are insoluble, and thus is usable as a top resist in double patterning process. Further, the resist according to the present invention has high water resistance and combines adequate water repellency with developer compatibility.

The resist according to the present invention shows adequate water repellency before exposure to light and attains quick solubility in a developer after exposure to light. Accordingly, it is assumed that the resist according to the present invention enables the formation of a high-resolution pattern without roughness not only by dry exposure but also by liquid-immersion exposure in which the resist film is exposed to light with a medium of higher refractive index than air, such as water, being filled in a space between the resist film and lens. In photolithography by liquid-immersion exposure, a top coat film as a protecting film for the resist may be or may not be used. The resist according to the present invention can be applied to liquid-immersion exposure by adjusting the composition and component ratio of the resist.

Examples of the medium used for liquid-immersion exposure include not only water but also a fluorine-based solvent, a silicon-based solvent, a hydrocarbon-based solvent, a sulfur-containing solvent and the like. The resist containing the fluorine-containing polymer (1) according to the present invention is applicable to these mediums.

4. Resist Pattern Forming Method

A resist pattern forming method according to the present invention includes: a film forming step of forming a film of the resist according to the present invention by applying the resist onto a substrate; an exposure step of subjecting the film to exposure to electromagnetic wave or high energy ray radiation of wavelength 300 nm or shorter through a photomask to thereby transfer a pattern of the photomask to the film; and a development step of developing the film with a developer to obtain the pattern. In the present invention, the term "high energy ray" refers to an electron beam or soft X-ray.

The resist pattern forming method according to the present invention is based on lithography using the resist containing any one of the fluorine-containing polymers (1) to (3) and can be performed through the following steps. In the film forming step (A), a film of the resist is formed by applying the resist onto a substrate. In the exposure step (B), the resist film is heated and then subjected to electromagnetic wave or high energy ray radiation of wavelength 300 nm or shorter through a patterned photomask. In the development step (C), the exposed resist film is developed with an alkaline developer whereby there is obtained, on the substrate, a resist pattern to which a mask of the photomask is transferred.

For example, in the film forming step (A), the resist film is formed on a silicon wafer as the substrate by spin coating the resist, which contains any one of the fluorine-containing polymers (1) to (3) according to the present invention, onto the silicon wafer and prebaking the spin-coated resist by heating the silicon wafer on a hot plate at 60° C. to 200° C. for 10 seconds to 10 minutes, preferably at 80° C. to 150° C. for 30 seconds to 2 minutes. In the subsequent exposure step (B), the patterned photomask is set in exposure equipment. Then, the resist film is exposed through the photomask to high energy ray radiation or electron beam, such as ultraviolet radiation, excimer laser radiation or X-ray, by means of the exposure equipment such that the exposure amount of high energy ray radiation or electron beam is in the range of 1 mJ/cm$^2$ to 200 mJ/cm$^2$, preferably 10 mJ/cm$^2$ to 100 mJ/cm$^2$. After that, the resist film is subjected to post-exposure baking (PEB) as required on a hot plate at 60° C. to 150° C. for 10 seconds to 5 minutes, preferably at 80° C. to 130° C. for 30 seconds to 3 minutes. In the subsequent development step (C), an aqueous solution containing tetramethylammonium hydroxide (TMAH) in an amount of 0.1 mass % to 5 mass %, preferably 2 mass % to 3 mass % is provided as the developer. The resist is developed by contact with the aqueous solution of tetramethylammonium hydroxide for 10 seconds to 3 minutes, more preferably 30 seconds to 2 minutes, by a known method such as a dipping method, a puddle method or a spraying method. With this, the desired resist pattern is obtained.

As the substrate, there can be used not only a silicon wafer but also a substrate of metal or glass. An organic or inorganic film may be provided on the substrate. For example, the substrate may be provided with an anti-reflection film or an undercoat layer for multilayer resist or may be provided with a resist pattern.

There is no particular limitation on the wavelength of the electromagnetic wave used in the exposure step for lithography of the resist in the present invention. UV light (wavelength 248 nm) from a KrF excimer layer, UV light (wavelength 193 nm) from an ArF excimer laser, extreme ultraviolet radiation for extreme ultraviolet lithography (EUV), X-ray can be used. Particularly preferred is UV light from an ArF excimer laser.

As mentioned above, the resist according to the present invention shows adequate water repellency before the light exposure and quick developer solubility after the light exposure and thus enables high-resolution pattern formation without pattern roughness.

It is feasible to manufacture a semiconductor device by the pattern forming method based on lithography using the resist according to the present invention. There is no particular limitation on the kind of the device. Examples of the device include semiconductor devices manufactured by fine processing on substrate, such as CPU (central processing unit), SRAM (static random access memory), DRAM (dynamic random access memory) and the like.

5. Ink Pattern Forming Composition

An ink pattern forming composition according to the present invention is prepared by adding an acid generator and a solvent to any of the fluorine-containing polymers (1) to (3), and can be used for ink pattern formation in printed electronics. Hereinafter, a pattern of ink is also simply referred to as "ink pattern".

In the present invention, the ink pattern forming composition contains the following components: any of the fluorine-containing polymers (1) to (3), (A) a photoacid generator and (B) a solvent. Preferably, the ink pattern forming composition further contains: (C) a quencher; (D) a sensitizer; and (E) a polymerizable compound. The ink pattern forming composition optionally contains a surfactant, a storage stabilizer, an adhesion aid and a heat resistance improver as required.

The acid generator (A) is a compound capable of, when a film of the ink pattern forming composition is exposed to light, generating an acid by irradiation with light. The solvent (B) is a substance for dissolving or dispersing the components of the ink pattern forming composition. The quencher (C) is a substance for suppressing the diffusion of the acid from the acid generator during the exposure so as to thereby obtain a pattern with high precision. The sensitizer (D) is a substance for improving the exposure sensitivity of the ink pattern forming composition. The polymerizable compound (E) is a compound for increasing the hardness of the pattern forming film obtained after the exposure. The respective components will be explained below.

5-1. (A) Acid Generator

A photoacid generator, which is capable of generating an acid by light irradiation, is usable as the acid generator (A) in the ink pattern forming composition.

The acid generator (A) used in the ink pattern forming composition can be of any kind capable of generating an acid by light irradiation. As the acid generator, there can be used an oximesulfonate compound, an onium salt, a sulfone imide compound, a halogen-containing compound, diazomethane compound, a sulfone compound, a sulfonate compound or a carboxylate compound.

[Oximesulfonate Compound]

The oximesulfonate compound can be any of those having a $C_1$-$C_{12}$ alkyl group, a $C_1$-$C_{12}$ fluoroalkyl group, a $C_4$-$C_{12}$ alicyclic hydrocarbon group or a $C_6$-$C_{20}$ aryl group. A part or all of hydrogen atoms of the above group may be substituted with a halogen atom or a substitute. Preferred are those having a $C_1$-$C_{12}$ linear or $C_3$-$C_{12}$ branched alkyl group. As the substituent, there can be used a $C_1$-$C_{10}$ alkoxy group or an alicyclic group including a bridged alicyclic group such as 7,7-dimethyl-2-oxonorbornyl.

The $C_1$-$C_{12}$ fluoroalkyl group is exemplified by a trifluoromethyl group, a pentafluoroethyl group or a heptylfluoropropyl group. As the substituent on the $C_4$-$C_{12}$ alicyclic hydrocarbon group, there can be used a $C_1$-$C_5$ alkyl or alkoxy group.

The $C_6$-$C_{20}$ aryl group is exemplified by a phenyl group, a naphthyl group, a tolyl group or a xylyl group. As the substituent on the $C_6$-$C_{20}$ aryl group, there can be used a $C_1$-$C_5$ alkyl or alkoxy group or a halogen atom.

Examples of the oximesulfonate compound include (5-propylsulfonyloxyimino-5H-thiophene-2-ylidene)(2-methylphenyl)acetonitrile, (5-octylsulfonyloxyimino-5H-thiophene-2-ylidene)(2-methylphenyl)acetonitrile, (camphorsulfonyloxyimino-5H-thiophene-2-ylidene)(2-methylphenyl)acetonitrile, (5-p-toluenesulfonyloxyimino-5H-thiophene-2-ylidene)(2-methylphenyl)acetonitrile and (5-octylsulfonyloxyimino)(4-methoxyphenyl)acetonitrile.

[Onium Salt]

The onium salt can be a diphenyliodonium salt, a triphenylsulfonium salt, an alkylsulfonium salt, a benzylsulfonium salt, a dibenzylsulfonium salt, a substituted benzylsulfonium salt, a benzothiazonium salt or a tetrahydrothiophenium salt.

<Diphenyliodonium Salt>

Examples of the diphenyliodonium salt include diphenyliodonium tetrafluoroborate, diphenyliodonium hexafluorophosphonate, diphenyliodonium hexafluoroarsenate, diphenyliodonium trifluoromethanesulfonate, diphenyliodonium trifluoroacetate, diphenyliodonium p-toluenesulfonate, diphenyliodonium butyl tris(2,6-difluorophenyl)borate, 4-methoxyphenylphenyliodonium tetrafluoroborate, bis(4-t-butylphenyl)iodonium tetrafluoroborate, bis(4-t-butylphenyl)iodonium hexafluoroarsenate, bis(4-t-butylphenyl)iodonium trifluoromethanesulfonate, bis(4-t-butylphenyl) iodonium trifluoroacetate, bis(4-t-butylphenyl)iodonium p-toluenesulfonate and bis(4-t-butylphenyl)iodonium camphorsulfonic acid.

<Triphenylsulfonium Salt>

Examples of the triphenylsulfonium salt include triphenylsulfonium trifluoromethanesulfonate, triphenylsulfonium camphorsulfonic acid, triphenylsulfonium tetrafluoroborate, triphenylsulfonium trifluoroacetate, triphenylsulfonium p-toluenesulfonate and triphenylsulfonium butyl tris(2,6-difluorophenyl)borate.

<Alkylsulfonium Salt>

Examples of the alkylsulfonium salt include 4-acetoxyphenyldimethylsulfonium hexafluoroantimonate, 4-acetoxyphenyldimethylsulfonium hexafluoroarsenate, dimethyl-4-(benzyloxycarbonyloxy)phenylsulfonium hexafluoroantimonate, dimethyl-4-(benzoyloxy)phenylsulfonium hexafluoroantimonate, dimethyl-4-(benzoyloxy)phenylsulfonium hexafluoroarsenate and dimethyl-3-chloro-4-acetoxyphenylsulfonium hexafluoroantimonate.

<Benzylsulfonium Salt>

Examples of the benzylsulfonium salt include benzyl-4-hydroxyphenylmethylsulfonium hexafluoroantimonate, benzyl-4-hydroxyphenylmethylsulfonium hexafluorophosphate, 4-acetoxyphenylbenzylmethylsulfonium hexafluoroantimonate, benzyl-4-methoxyphenylmethylsulfonium hexafluoroantimonate, benzyl-2-methyl-4-hydroxyphenylmethylsulfonium hexafluoroantimonate, benzyl-3-chloro-4-hydroxyphenylmethylsulfonium hexafluoroarsenate and 4-methoxybenzyl-4-hydroxyphenylmethylsulfonium hexafluorophosphate.

<Dibenzylsulfonium Salt>

Examples of the dibenzylsulfonium salt include dibenzyl-4-hydroxyphenylsulfonium hexafluoroantimonate, dibenzyl-4-hydroxyphenylsulfonium hexafluorophosphate, 4-acetoxyphenyldibenzylsolfonium hexafluoroantimonate, dibenzyl-4-methoxyphenylsulfonium hexafluoroantimonate, dibenzyl-3-chloro-4-hydroxyphenylsulfonium hexafluoroarsenate, dibenzyl-3-methyl-4-hydoxy-5-t-butylphenylsulfonium hexafluoroantimonate and benzyl-4-methoxybenzyl-4-hydroxyphenylsulfonium hexafluorophosphate.

<Substituted Benzylsulfonium Salt>

Examples of the substituted benzylsulfonium salt include p-chlorobenzyl-4-hydroxyphenylmethylsulfonium hexafluoroantimonate, p-nitrobenzyl-4-hydroxyphenylmethylsulfonium hexafluoroantimonate, p-chlorobenzyl-4-hydroxyphenylmethylsulfonium hexafluorophosphate, p-nitrobenzyl-3-methyl-4-hydroxyphenylmethylsulfonium hexafluoroantimonate, 3,5-dichlorobenzyl-4-hydroxyphenylmethylsulfonium hexafluoroantimonate and o-chlorobenzyl-3-chloro-4-hydroxyphenylmethylsulfonium hexafluoroantimonate.

<Benzothiazonium Salt>

Examples of the benzothiazonium salt include 3-benzylbenzothiazonium hexafluoroantimonate, 3-benzylbenzothiazonium hexafluorophosphate, 3-benzylbenzothiazonium tetrafluoroborate, 3-(p-methoxybenzyl)benzothiazonium hexafluoroantimonate, 3-benzyl-2-methylthiobenzothiazonium hexafluoroantimonate and 3-benzyl-5-chlorobenzothiazonium hexafluoroantimonate.

<Tetrahydrothiophenium Salt>

Examples of the tetrahydrothiophenium salt include 4,7-di-n-butoxy-1-naphtyltetrahydrothiophenium trifluoromethanesulfonate, 1-(4-n-butoxynaphthalene-1-yl)tetrahydrothiophenium trifluoromethanesulfonate, 1-(4-n-butoxynaphthalene-1-yl)tetrahydrothiophenium nonafluoro-n-butanesulfonate, 1-(4-n-butoxynaphthalene-1-yl)tetrahydrothiophenium 1,1,2,2-tetrafluoro-2-(norbornane-2-yl)ethanesulfonate, 1-(4-n-butoxynaphthalene-1-yl)tetrahydrothiophenium 2-(5-t-butoxycarbonyloxybicyclo[2.2.1]heptane-2-yl)-1,1,2,2-tetrafluoroethanesulfonate and 1-(4-n-butoxynaphthalene-1-yl)tetrahydrothiophenium 2-(6-t-butoxycarbonyloxybicyclo[2.2.1]heptane-2-yl)-1,1,2,2-tetrafluoroethanesulfonate.

[Sulfone Imide Compound]

Examples of the sulfone imide compound include N-(trifluoromethylsulfonyloxy)succinimide, N-(camphorsulfonyloxy)succinimide, N-(4-methylphenylsulfonyloxy)succinimide, N-(2-trifluoromethylphenylsulfonyloxy)succinimide, N-(4-fluorophenylsulfonyloxy)succinimide, N-(trifluoromethylsulfonyloxy)phthalimide, N-(camphorsulfonyloxy)phthalimide, N-(2-trifluoromethylphenylsulfonyloxy)phthalimide, N-(2-fluorophenylsulfonyloxy)phthalimide, N-(trifluoromethylsulfonyloxy)diphenylmaleimide, N-(camphorsulfonyloxy)diphenylmaleimide, N-(4-methylphenylsulfonyloxy)diphenylmaleimide, N-(2-trifluoromethylphenylsulfonyloxy)diphenylmaleimide, N-(4-fluorophenylsulfonyloxy)diphenylmaleimide, N-(4-fluorophenylsulfonyloxy)diphenylmaleimide, N-(phenylsulfonyloxy)bicyclo[2.2.1]hept-5-ene-2,3-dicarboxyimide, N-(4-methylphenylsulfonyloxy)bicyclo[2.2.1]hept-5-ene-2,3-dicarboxyimide, N-(trifluoromethanesulfonyloxy)bicyclo[2.2.1]hept-5-ene-2,3-dicarboxyimide, N-(nonafluorobutanesulfonyloxy)bicyclo[2.2.1]hept-5-ene-2,3-dicarboxyimide, N-(camphorsulfonyloxy)bicyclo[2.2.1]hept-5-ene-2,3-dicarboxyimide, N-(camphorsulfonyloxy)-7-oxabicyclo[2.2.1]hept-5-ene-2,3-dicarboxyimide, N-(trifluoromethylsulfonyloxy)-7-oxabicyclo[2.2.1]hept-5-ene-2,3-dicarboxyimide, N-(4-methylphenylsulfonyloxy)bicyclo[2.2.1]hept-5-ene-2,3-dicarboxyimide, N-(4-methylphenylsulfonyloxy)-7-oxabicyclo[2.2.1]hept-5-ene-2,3-dicarboxyimide, N-(2-trifluoromethylphenylsulfonyloxy)bicyclo[2.2.1]hept-5-ene-2,3-dicarboxyimide, N-(2-trifluoromethylphenylsulfonyloxy)-7-oxabicyclo[2.2.1]hept-5-ene-2,3-dicarboxyimide, N-(4-fluorophenylsulfonyloxy)bicyclo[2,2,1]hept-5-ene-2,3-dicarboxyimide, N-(4-fluorophenylsulfonyloxy)-7-oxabicyclo[2.2.1]hept-5-ene-2,3-dicarboxyimide, N-(trifluoromethylsulfonyloxy)bicyclo[2.2.1]heptane-5,6-oxy-2,3-dicarboxyimide, N-(camphorsulfonyloxy)bicyclo[2.2.1]heptane-5,6-oxy-2,3-dicarboxyimide, N-(4-methylphenylsulfonyloxy)bicyclo[2.2.1]heptane-5,6-oxy-2,3-dicarboxyimide, N-(2-trifluoromethylphenylsulfonyloxy)bicyclo[2.2.1]heptane-5,6-oxy-2,3-dicarboxyimide, N-(4-fluorophenylsulfonyloxy)bicyclo[2.2.1]heptane-5,6-oxy-2,3-dicarboxyimide, N-(trifluoromethylsulfonyloxy)naphthyldicarboxyimide, N-(camphorsulfonyloxy)naphthyldicarboxyimide, N-(4-methylphenylsulfonyloxy)naphthyldicarboxyimide, N-(phenylsulfonyloxy)naphthyldicarboxyimide, N-(2-trifluoromethylphenylsulfonyloxy)naphthyldicarboxyimide, N-(4-fluorophenylsulfonyloxy)naphthyldicarboxyimide, N-(pentafluoroethylsulfonyloxy)naphthyldicarboxyimide, N-(heptafluoropropylsulfonyloxy)naphthyldicarboxyimide, N-(nonafluorobutylsulfonyloxy)naphthyldicarboxyimide, N-(ethylsulfonyloxy)naphthyldicarboxyimide, N-(propylsulfonyloxy)naphthyldicarboxyimide, N-(butylsulfonyloxy)naphthyldicarboxyimide, N-(pentylsulfonyloxy)naphthyldicarboxyimide, N-(hexylsulfonyloxy)naphthyldicarboxyimide, N-(heptylsulfonyloxy)naphthyldicarboxyimide, N-(octylsulfonyloxy)naphthyldicarboxyimide, and N-(nonylsulfonyloxy)naphthyldicarboxyimide.

[Halogen-Containing Compound]

Examples of the halogen-containing compound include a haloalkyl-containing hydrocarbon compound and a haloalkyl-containing heterocyclic compound.

[Diazomethane Compound]

Examples of the diazomethane compound include bis(trifluoromethylsulfonyl)diazomethane, bis(cyclohexylsulfonyl)diazomethane, bis(phenylsulfonyl)diazomethane, bis(p-tolylsulfonyl)diazomethane, bis(2,4-xylylsulfonyl)diazomethane, methylsulfonyl p-toluenesulfonyl diazomethane, cyclohexylsulfonyl(1,1-dimethylethylsulfonyl)diazomethane, bis(1,1-dimethylethylsulfonyl)diazomethane and phenylsulfonyl(benzoyl)diazomethane.

[Sulfone Compound]

Examples of the sulfone compound include β-ketosulfone compound, β-sulfonylsulfone compound and diaryldisulfone compound.

[Sulfonate Compound]

Examples of the sulfonate compound include alkyl sulfonic acid ester, haloalkyl sulfonic acid ester, aryl sulfonic acid ester, imino sulfonate.

[Carboxylate Compound]

Examples of the carboxylate compound include carboxylic acid o-nitrobenzyl ester.

<Acid Generator (A) in Ink Pattern Forming Composition>

The above acid generators can be used solely or in combination of two or more kinds thereof. Among others, preferred are the oxime sulfonate compound, the onium salt and the sulfonate compound because each of these compounds has a large effect of improving the exposure sensitivity of the film of the ink pattern forming composition. The oxime sulfonate compound is particularly preferred.

[Content of Acid Generator (A) in Ink Pattern Forming Composition]

The content of the acid generator (A) in the ink pattern forming composition is preferably in the range of 0.1% to 10%, more preferably 1% to 5%, in terms of mass % based on the total mass of the fluorine-containing polymer (1). When the content of the acid generator (A) is in the above range, the ink pattern forming composition attains high exposure sensitivity to form a finer pattern forming film with liquid-repellent and liquid-philic portions.

5-2. (B) Solvent

The solvent (B) can be of any kind capable of dissolving or dispersing the respective components of the ink pattern forming composition. As the solvent (B), there can be used an organic solvent such as an alcohol, an ether, an diethylene glycol alkyl ether, an ethylene glycol alkyl ether acetate, a propylene glycol alkyl ether acetate, a propylene glycol monoalkyl ether propionate, an aliphatic hydrocarbon, an aromatic hydrocarbon, a ketone or an ester. The following are examples of the solvent (B).

[Alcohol]

The alcohol can be a long-chain alkyl alcohol, an aromatic alcohol, an ethylene glycol monoalkyl ether, a propylene glycol monoalkyl ether, a dipropylene glycol monoalkyl ether, and the like.

<Long-Chain Alkyl Alcohol>

Examples of the long-chain alkyl alcohol include 1-hexanol, 1-octanol, 1-nonanol, 1-dodecanol, 1,6-hexanediol, and 1,8-octanediol.

<Aromatic Alcohol>

Examples of the aromatic alcohol include benzyl alcohol.

Examples of the ethylene glycol monoalkyl ether include ethylene glycol monomethyl ether, ethylene glycol monoethyl ether, ethylene glycol monopropyl ether, and ethylene glycol monobutyl ether.

<Propylene Glycol Monoalkyl Ether>

Examples of the propylene glycol monoalkyl ether include propylene glycol monomethyl ether, propylene glycol monoethyl ether, propylene glycol monopropyl ether, and propylene glycol monobutyl ether.

<Dipropylene Glycol Monoalkyl Ether>

Examples of the dipropylene glycol monoalkyl ether include dipropylene glycol monomethyl ether, dipropylene glycol monoethyl ether, dipropylene glycol monopropyl ether, and dipropylene glycol monobutyl ether.

Among these alcohols, benzyl alcohol, ethylene glycol monopropyl ether, ethylene glycol monobutyl ether, propylene glycol monomethyl ether and propylene glycol monoethyl ether are preferred for ease of dissolution and film formation of the ink pattern forming composition.

[Ether]

Examples of the ether include tetrahydrofuran, hexyl methyl ether, triethylene glycol dimethyl ether, triethylene glycol diethyl ether and 1,4-dioxane.

[Diethylene Glycol Alkyl Ether]

Examples of the diethylene glycol alkyl ether include diethylene glycol dimethyl ether, diethylene glycol diethyl ether and diethylene glycol ethyl methyl ether.

[Ethylene Glycol Alkyl Ether Acetate]

Examples of the ethylene glycol alkyl ether acetate include methyl cellosolve acetate, ethyl cellosolve acetate, ethylene glycol monobutyl ether acetate and ethylene glycol monoethyl ether acetate.

[Propylene Glycol Alkyl Ether Acetate]

Examples of the propylene glycol alkyl ether acetate include propylene glycol monomethyl ether acetate, propylene glycol monoethyl ether acetate, propylene glycol monopropyl ether acetate and propylene glycol monobutyl ether acetate.

[Propylene Glycol Monoalkyl Ether Propionate]

Examples of the propylene glycol monoalkyl ether propionate include propylene glycol monomethyl ether propionate, propylene glycol monoethyl ether propionate, propylene glycol monopropyl ether propionate and propylene glycol monobutyl ether propionate.

[Aliphatic Hydrocarbon]

Examples of the aliphatic hydrocarbon include n-pentane, n-hexane, n-heptane, n-octane, n-nonane, n-decane, n-undecane, n-dodecane, cyclohexane and decalin.

[Aromatic Hydrocarbon]

Examples of the aromatic hydrocarbon include benzene, toluene, xylene, ethylbenzene, n-propylbenzene, i-propylbenzene, n-butylbenzene, mesitylene, chlorobenzene and dichlorobenzene.

[Ketone]

Examples of the ketone include methyl ethyl ketone, methyl isobutyl ketone, cyclohexanone, 2-heptanone and 4-hydroxy-4-methyl-2-pentanone.

[Ester]

Examples of the ester include methyl acetate, ethyl acetate, propyl acetate, i-propyl acetate, butyl acetate, methyl 2-hydroxypropanoate, methyl 2-hydroxy-2-methylpropanoate, ethyl 2-hydroxy-2-methylpropanoate, methyl hydroxyacetate, ethyl hydroxyacetate, butyl hydroxyacetate, methyl lactate, ethyl lactate, propyl lactate, butyl lactate, methyl 3-hydroxypropanoate, ethyl 3-hydroxypropanoate, propyl 3-hydroxypropanoate, butyl 3-hydroxypropanoate, methyl 2-hydroxy-3-methylbutanoate, methyl methoxyacetate, ethyl methoxyacetate, propyl methoxyacetate, butyl methoxyacetate, methyl ethoxyacetate, ethyl ethoxyacetate, propyl ethoxyacetate, butyl ethoxyacetate, methyl propoxyacetate, ethyl propoxyacetate, propyl propoxyacetate, butyl propoxyacetate, methyl butoxyacetate, ethyl butoxyacetate, propyl butoxyacetate, butyl butoxyacetate, methyl 2-methoxypropionate, ethyl 2-methoxypropionate, propyl 2-methoxypropionate, butyl 2-methoxypropionate, methyl 2-ethoxypropionate and ethyl 2-ethoxypropionate.

The above solvents (B) can be used solely or in combination of two or more kinds thereof.

[Content of Solvent (B) in Ink Pattern Forming Composition]

The content of the solvent (B) in the ink pattern forming composition is preferably in the range of 200 to 1600 parts by mass, more preferably 400 to 1000 parts by mass, per 100 parts by mass of the ink pattern forming composition except the solvent (B). When the content of the solvent (B) is in the above range, the ink pattern forming composition is improved in substrate wettability and can form a uniform film by suppressing unevenness of application.

5-3. (C) Quencher

The quencher (C) functions as an acid diffusion suppression substance to suppress the diffusion of the acid from the acid generator (A) during the exposure of the film of the ink pattern forming composition. As the quencher (C), there can be used a photodegradable base capable of generating a weak acid by exposure to light. An onium salt compound is a preferred example of the photodegradable base.

The photodegradable base generates an acid in the exposed portion. On the other hand, the photodegradable base exerts a high acid trapping function by the action of an anion in the unexposed portion so as to trap the acid generated from the acid generator (A) and quench the acid diffused from the exposed portion to the unexposed portion. The quenching of the acid is caused only in the unexposed portion. Thus, the pattern forming film obtained after the exposure of the ink pattern forming composition shows a clear boundary between the liquid-repellent and liquid-philic portions so that the ink, when applied to the pattern forming film, attains a fine ink pattern with improved contrast. One kind of quencher or two or more kinds of quenchers in combination can be used.

[Content of Quencher (C) in Ink Pattern Forming Composition]

The content of the quencher (C) in the ink pattern forming composition is preferably in the range of 0.001 to 5 parts by mass, more preferably 0.005 to 3 parts by mass, per 100 parts by mass of the fluorine-containing polymer (1). When the content of the quencher (C) is in the above range, the pattern forming film after the exposure of the ink pattern forming composition shows a clear boundary between the liquid-repellent and liquid-philic portions so that the ink, when applied to the pattern forming film, attains a fine ink pattern with improved contrast.

5-4. (D) Sensitizer

The sensitizer (D) is added when further improvement in the exposure sensitivity of the ink pattern forming composition is intended. The sensitizer (D) is preferably a compound capable of being shifted to an excited state by absorption of a light beam or radiation. The sensitizer (D), when shifted to an excited state, causes an electron transfer, energy transfer or heat generation upon contact with the acid generator (A) so that the acid generator (A) is easily decomposed to form an acid under the influence of such an electron transfer, energy transfer or heat generation. The sensitizer (D) can be of any kind having an absorption wavelength in the region of 350 nm to 450 nm. As the sensitizer (D), there can be used a polynuclear aromatic compound, a xanthene, a xanthone, a cyanine, a merocyanine, a rhoda cyanine, an oxonol, a thiazine, an acridine, an acridone, an anthraquinone, a squarylium, a styryl, a styryl base or a coumarin.

The following are examples of the sensitizer (D).

[Polynuclear Aromatic Compound]

Examples of the polynuclear aromatic compound include pyrene, tolylene triphenylene, anthracene, 9,10-dibutoxyanthracene, 9,10-diethoxyanthracene, 3,7-dimethoxyanthracene and 9,10-dipropyloxyanthracene.

[Xanthene]

Examples of the xanthene include fluorescein, eosine, erythrosine, rhodamine B and rose bengal.

[Xanthone]

Examples of the xanthone include xanthone, thioxanthone, dimethyl thioxanthone, diethylthioxanthone and isopropyl thioxanthone.

[Cyanine]

Examples of the cyanine include thiacarbocyanine and oxacarbocyanine.

[Merocyanine]

Examples of the merocyanine include merocyanine and carbomerocyanine.

[Thiazine]

Examples of the thiazine include thionine, methylene blue and toluidine blue.

[Acridine]

Examples of the acridine include acridine orange, chloroflavin and acriflavin.

[Acridone]

Examples of the acridone include acridone and 10-butyl-2-chloroacridone.

[Anthraquinone]

Examples of the anthraquinone include anthraquinone.

[Squarylium]

Examples of the squarylium include squarylium.

[Styryl Base]

Examples of the styryl base include 2-[2-[4-(dimethylamino)phenyl]ethenyl]benzooxazol.

[Coumarin]

Examples of the coumarin include 7-diethylamino 4-methylcoumarin, 7-hydroxy 4-methylcoumarin and 2,3,6,7-tetrahydro-9-methyl-1H,5H,11H[1]benzopyrano[6,7,8-ij]quinolizin-11-one.

The above sensitizers (D) can be used solely or in combination of two or more kinds thereof.

<Sensitizer (D) in Ink Pattern Forming Composition>

As the sensitizer (D), the polynuclear aromatic compound, the acridone, the styryl, the styryl base, the coumarin and the xanthone are preferred because each of these compounds has a large effect of improving the exposure sensitivity of the ink pattern forming composition. Among various xanthones, diethylthioxanthone and isopropyl thioxanthone are particularly preferred.

[Content of Sensitizer (D) in Ink Pattern Forming Composition]

The content of the sensitizer (D) in the ink pattern forming composition is preferably in the range of 0.1 to 8 parts by mass, more preferably 1 to 4 parts by mass, per 100 parts by mass of the fluorine-containing polymer (1). When the content of the sensitizer (D) is in the above range, the exposure sensitivity of the ink pattern forming composition is improved. Thus, the pattern forming film after the exposure of the ink pattern forming composition shows a clear boundary between the liquid-repellent and liquid-philic portions so that the ink, when applied to the pattern forming film, attains a fine ink pattern with improved contrast.

5-5. (E) Polymerizable Compound

The polymerizable compound (E) is contained in the ink pattern forming composition so as to make the pattern forming film harder. The polymerizable compound (E) is an ethylenically unsaturated bond-containing compound other than the fluorine-containing polymer (1). As such a polymerizable compound (E), there can be used a monofunctional, bifunctional or higher functional acrylic ester or methacrylic ester that has good polymerizability and allows the formation of a harder pattern forming film from the ink pattern forming composition.

The following are examples of the polymerizable compound (E).

[Monofunctional Acrylic Ester and Methacrylic Ester]
<Monofunctional Acrylic Ester>

Examples of the monofunctional acrylic ester include 2-hydroxyethyl acrylate, diethylene glycol monoethyl ether acrylate, (2-acryloyloxyethyl)(2-hydroxypropyl)phthalate and (2-methacryloyloxyethyl)(2-hydroxypropyl)phthalate.

<Monofunctional Methacrylic Ester>

Examples of the monofunctional methacrylic ester include 2-hydroxyethyl methacrylate, diethylene glycol monoethyl ether methacrylate and ω-carboxypolycaprolactone monoacrylate.

The monofunctional acrylic ester and methacrylic ester may be those commercially available under the trade names of ARONIX (trademark) series M-101, M-11, M-114 and M-5300 from Toagosei Co., Ltd., KAYARAD series TC-110S and TC-120S from Nippon Kayaku Co., Ltd., and VISCOAT series 158 and 2311 from Osaka Organic Chemical Industry Ltd. etc.

[Bifunctional Acrylic Ester and Methacrylic Ester]

Examples of the bifunctional acrylic ester include ethylene glycol diacrylate, propylene glycol diacrylate, diethylene glycol diacrylate, tetraethylene glycol diacrylate, 1,6-hexanediol diacrylate and 1,9-nonanediol diacrylate.

Examples of the bifunctional methacrylic ester include propylene glycol dimethacrylate, ethylene glycol dimethacrylate, diethylene glycol dimethacrylate, tetraethylene glycol dimethacrylate, 1,6-hexanediol dimethacrylate and 1,9-nonanediol dimethacrylate.

The bifunctional acrylic ester and methacrylic ester may be those commercially available under the trade names of ARONIX (trademark) series M-210, M-240 and M-6200 from Toagosei Co., Ltd., KAYARAD series HDDA, HX-220 and R-604 from Nippon Kayaku Co., Ltd., VISCOAT series 260, 312 and 335HP from Osaka Organic Chemical Industry Ltd., and LIGHT ACRYLATE series 1,9-NDA from Kyoeisha Chemical Co., Ltd. etc.

Examples of the trifunctional or higher functional acrylic ester and methacrylic ester include trimethylolpropane triacrylate, trimethylolpropane trimethacrylate, pentaerythritol triacrylate, pentaerythritol trimethacrylate, pentaerythritol tetraacrylate, pentaerythritol tetramethacrylate, dipentaerythritol pentaacrylate, dipentaerythritol pentamethacrylate, dipentaerythritol hexaacrylate, a mixture of dipentaerythritol pentaacrylate and dipentaerythritol hexaacrylate, dipentaerythritol hexamethacrylate, ethylene oxide-modified dipentaerythritol hexaacrylate, tri(2-acryloyloxyethyl)phosphate, tri(2-methacryloyloxyethyl)phosphate, succinic acid-modified pentaerythritol triacrylate, succinic acid-modified dipentaerythritol pentaacrylate, tris(acryloxyethyl)isocyanulate, and polyfunctional urethane acrylate compounds each obtained by reaction of a compound having a linear alkylene group and an alicyclic structure as well as having two or more isocyanate groups with a compound having one or more hydrox groups and three, four or five (meth)acryloyloxy groups in the molecule.

The trifunctional or higher functional acrylic ester and methacrylic ester may be those commercially available under the trade names of e.g. ARONIX (trademark) series M-309, M-315, M-400, M-405, M-450, M-7100, M-8030, M-8060 and TO-1450 from Toagosei Co., Ltd., KAYARAD series TMPTA, DPHA, DPCA-20, DPCA-30, DPCA-60, DPCA-120, DPEA-12 from Nippon Kayaku Co., Ltd., VISCOAT series 295, 300, 360, GPT, 3PA and 400 from Osaka Organic Chemical Industry Ltd., and LIGHT ACRYLATE series 1,9-NDA from Kyoeisha Chemical Co., Ltd. etc. Further, the polyfunctional urethane acrylate compounds may be those commercially available under the trade names of NEW FRONTIER (trademark) series R-1150 from DKS Co. Ltd., KAYARAD series DPHA-40H from Nippon Kayaku Co., Ltd. etc.

As the polymerizable compound (E), preferred are co-carboxypolycaprolactone monoacrylate, 1,9-nonanediol dimethacrylate, trimethylolpropane triacrylate, pentaerythritol triacrylate, pentaerythritol tetraacrylate, dipentaerythritol pentaacrylate, dipentaerythritol hexaacrylate, mixture of dipentaerythritol pentaacrylate and dipentaerythritol hexaacrylate, ethylene oxide-modified dipentaerythritol hexaacrylate, succinic acid-modified pentaerythritol triacrylate, succinic acid-modified dipentaerythritol pentaacrylate and the polyfunctional urethane acrylate compounds because of each of these compounds has a large effect of making the pattern forming film of the ink pattern forming composition harder. Particularly preferred are the trifunctional or higher functional acrylic (or methacrylic) esters such as mixture of dipentaerythritol pentaacrylate and dipentaerythritol hexaacrylate.

[Content of Polymerizable Compound (E) in Ink Pattern Forming Composition]

The above polymerizable compounds (E) can be used solely or in combination of two or more kinds thereof. The content of the polymerizable compound (E) in the ink pattern forming composition is preferably in the range of 1 to 300 parts by mass, more preferably 3 to 200 parts by mass, still more preferably 5 to 100 parts by mass, per 100 parts by mass of the fluorine-containing polymer (1). When the content of the polymerizable compound (E) is in the above range, the pattern forming film of the ink pattern forming composition is made harder.

6. Ink Pattern Forming Method

An ink pattern forming method according to the present invention can be performed in two ways (A) and (B). The ink pattern forming method (A) utilizes a photomask, whereas the ink pattern forming method (B) utilizes drawing equipment.

[Ink Pattern Forming Method (A)]

The ink pattern forming method (A) according to the present invention includes: a film forming step of forming a film of the ink pattern forming composition by applying the ink pattern forming composition onto a substrate; an exposure step of subjecting the film to exposure to light radiation of wavelength 150 to 500 nm through a photomask to transfer a pattern of the photomask to the film, thereby obtaining a pattern forming film with liquid-repellent and liquid-philic portions; and a pattern forming step of forming a pattern of ink by applying the ink to the pattern forming film.

[Ink Pattern Forming Method (B)]

The ink pattern forming method (B) according to the present invention includes: a film forming step of forming a film of the ink pattern forming composition by applying the ink pattern forming composition on a substrate, and then, heating the film; a drawing step of drawing a pattern on the film by subjecting the film to scanning exposure to light radiation of wavelength 150 to 500 nm by means of drawing equipment, thereby obtaining a pattern forming film with liquid-repellent and liquid-philic portions; and an ink pattern forming step of applying an ink to the pattern forming film.

6-1. Film Forming Step, Exposure or Drawing Step and Ink Pattern Forming Step of Ink Pattern Forming Method The film forming step common to the ink pattern forming methods (A) and (B), the exposure fixing step in the ink pattern forming method (A), the drawing step in the ink pattern forming method (B) and the ink pattern forming step common to the ink pattern forming methods (A) and (B) will be explained below.

6-2. Film Forming Step

In the film forming step, the ink pattern forming composition according to the present invention is applied onto the substrate. Then, the thus-formed film is subjected to heating (prebaking).

[Substrate]

The substrate used in the film forming step can be a substrate of resin, glass, quartz or semiconductor e.g. silicon etc. conventionally used for electronic circuits. Examples of the resin substrate include those of polyethylene terephthalate, polybutylene terephthalate, polyethylene naphthalate, polyethersulfone, polycarbonate and polyimide.

Before the application of the ink pattern forming composition to the substrate, a surface of the substrate may be subjected to pretreatment such as washing, roughening, fine surface unevenness formation etc. as required.

[Application Method]

There is no particular limitation on the method for application of the ink pattern forming composition to the substrate. The ink pattern forming composition can be applied by a coating method using a brush, a dipping method, a spraying method, a roll coating method, a rotation coating (spin coating) method, a slit die coating method, a bar coating method, a flexographic printing method, an offset printing method, an ink-jet printing method, a dispense method or the like. In the ink pattern forming method, it is preferable to use a spin coating method.

[Film Thickness]

The thickness of the film formed in the film forming step can be adjusted as appropriate depending on the desired use. In the ink pattern forming method, the thickness of the film is preferably in the range of 0.1 μm to 20 μm.

[Prebaking]

The prebaking conditions vary depending on the chemical makeup of the ink pattern forming composition used. As to the common prebaking conditions for the ink pattern forming methods (A) and (B), it is preferable to adopt a heating temperature of 60° C. to 120° C. and a heating time of 1 minute to 10 minutes.

6-3. Exposure Step and Drawing Step

[Exposure Step]

In the exposure step of the ink pattern forming method (A), the film formed in the film forming step is subjected to exposure to light radiation of wavelength 150 to 500 nm through a photomask so as to transfer a pattern of the photomask to the film. There is thus obtained a pattern forming film with liquid-repellent and liquid-philic portions. The exposure step is carried out using a photomask with a predetermined pattern so that the exposed portion is formed in the same pattern as the desired pattern.

[Drawing Step]

In the drawing step of the ink pattern forming method (B), the film formed in the forming step is subjected to scanning exposure to light radiation of wavelength 150 to 500 nm by means of drawing equipment so as to draw a pattern on the film. There is thus obtained a pattern forming film with liquid-repellent and liquid-philic portions. The drawing step is carried out by, for example, performing scanning in a predetermined pattern with the use of a direct drawing exposure machine.

[Light Used]

In the exposure step and the drawing step, there can be used radiation of visible light, ultraviolet light, X-ray or charged particle beam. It is preferable to use ultraviolet radiation of wavelength 150 to 500 nm. Particularly preferred is ultraviolet radiation of wavelength 365 nm from an ultraviolet light emitting diode.

In the exposure step and the drawing step,

The acid-decomposable group is dissociated and evaporated from the fluorine-containing polymer (1) under the action of the acid generated from the acid generator (A). As a result, the film thickness of the exposed portion is made smaller than the film thickness of the unexposed portion to form a concave shape. Since the acid-decomposable group contains a fluorine atom, the unexposed portion remains liquid repellent; and the exposed portion becomes liquid-philic. Thus, the film on the substrate is processed into the pattern forming film with the liquid-repellent unexposed portion and the liquid-philic exposed portion of concave pattern.

[Heating]

It is preferable to heat the pattern forming film after the exposure. The heating of the pattern forming film after the exposure allows further evaporation of the acid dissociated from the fluorine-containing polymer (1) so as to achieve higher-definition pattern formation by the exposed concave portion and the unexposed convex portion.

The pattern forming film can be heated by using a hot plate, batch oven or conveyor oven, by a hot-air drying method using a dryer etc. or by a vacuum baking method.

The heating conditions vary depending on the chemical makeup of the composition, the thickness of the film etc. The heating is preferably performed at 60° C. to 150° C. for 3 minutes to 30 minutes.

6-4. Ink Pattern Forming Step

The ink pattern is obtained by applying the ink onto the above-obtained pattern forming film.

The difference between the contact angles of the liquid-repellent and liquid-philic portions of the pattern forming film after the exposure, with respect to the ink solvent such as water or hexadecane, is preferably 30° or greater, more preferably 50° or greater. When the contact angle difference is in the above range, the ink applied is readily rejected by the convex liquid-repellent portion and moved to the concave liquid-philic portion so that the ink pattern is formed with higher definition by the exposed concave portion and the unexposed convex portion.

[Formation of Conductive Ink Pattern]

By using a conductive ink as the ink in the ink pattern forming method, it is feasible to form a conductive ink pattern on the substrate.

6-5. Application to Electronic Circuit and Electronic Device

It is feasible to produce an electronic device using an electronic circuit formed with a conductive ink pattern on the substrate by the ink pattern forming method. The electronic circuit is a wiring system consisting of the conductive ink pattern formed on the substrate. The electronic device is a device with the electronic circuit. Examples of the electronic device include a portable information device such as liquid crystal display or mobile phone, a digital camera, an organic display, an organic EL lighting device and various sensors and wearable devices.

7. Fluorine-Containing Monomer

In the present invention, each of the fluorine containing monomers (1) to (3) is obtained by homopolymerization or copolymerization of a fluorine-containing monomer of the following formula (4).

[Fluorine-Containing Monomer (4)]

More specifically, a fluorine-containing monomer according to the present invention has a fluorine-containing cyclic acetal structure of the following formula (4). The fluorine-containing polymer (1) is obtained by homopolymerization or copolymerization of the fluorine-containing monomer of the formula (4). This monomer is hereinafter also referred to as "fluorine-containing monomer (4).

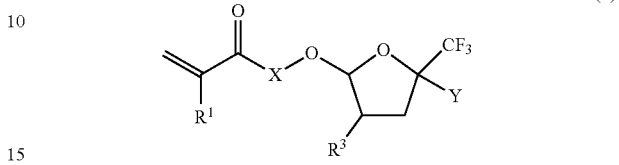

(4)

In the above formula (4), $R^1$ is a hydrogen atom, a fluorine atom, or a $C_1$-$C_{10}$ linear or $C_3$-$C_{10}$ branched alkyl group in which seven or less of hydrogen atoms bonded to carbon atoms may be substituted with fluorine; $R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; X is a single bond, or a divalent group in which seven or less of hydrogen atoms may be substituted with fluorine; Y is a $C_1$-$C_3$ fluoroalkyl or carboxylate (—COOR) group in which seven or less of hydrogen atoms may be substituted with fluorine; and R is a $C_1$-$C_3$ fluoroalkyl group. The same applies to the following.

[Fluorine-Containing Monomer (5)]

In the present invention, the fluorine-containing monomer (4) is preferably a fluorine-containing monomer of the following formula (5) corresponding to the case where $R^2$, $R^4$ and $R^5$ in the formula (4) are respectively hydrogen atoms.

In order for the fluorine-containing polymer (1), which is obtained by polymerization of the fluorine-containing monomer (4), to be soluble in a solvent such that the resulting resist or ink pattern forming composition can be applied as a film on a substrate, it is preferable that $R^2$, $R^4$ and $R^5$ in the formula (4) are respectively hydrogen atoms. In other words, a monomer having a fluorine-containing cyclic acetal structure of the following formula (5) is preferred in the present invention. This monomer is hereinafter also referred to as "fluorine-containing monomer (5)".

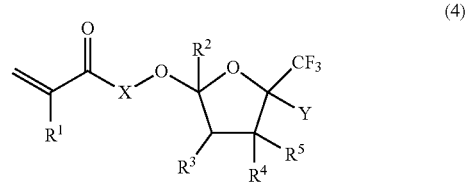

(5)

In the above formula (5), $R^1$, $R^3$, X and Y have the same definitions as those in the formula (4).

[Fluorine-Containing Monomer (6)]

Further, the fluorine-containing monomer (5) is preferably a fluorine-containing monomer of the following formula (6) corresponding to the case where Y in the formula (5) is a trifluoromethyl group. It is preferable that Y in the formula (4) is a trifluoromethyl group in order for the fluorine-containing polymer (2), which is obtained by homopolymerization or copolymerization of the fluorine-containing monomer (5), to soluble in the solvent such that the resulting resist or ink pattern forming composition can be applied as a film on the substrate. In other words, a monomer having a fluorine-containing cyclic acetal structure of the following formula (6) is preferred. This monomer is hereinafter also referred to as "fluorine-containing monomer (6)".

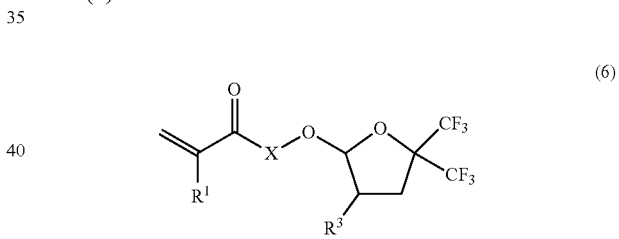

(6)

In the above formula (6), $R^1$, $R^3$ and X have the same definitions as those in the formula (4).

Examples of the fluorine-containing monomer (4) according to the present invention include, but are not limited to, the following structures.

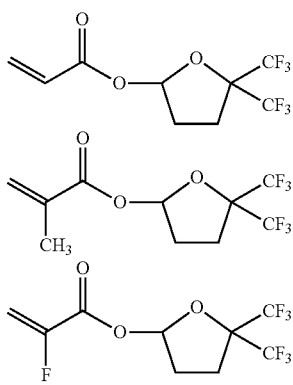

37
-continued
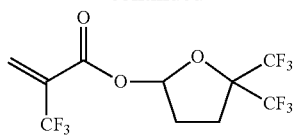
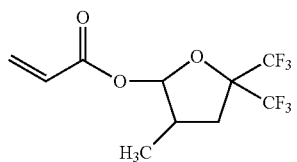
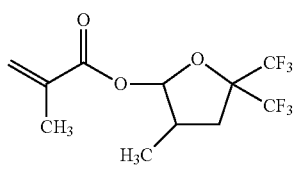
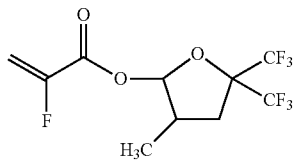
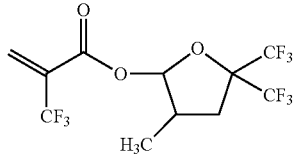
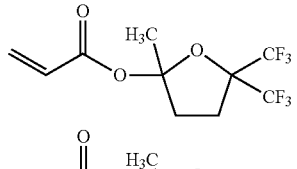
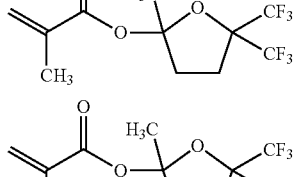
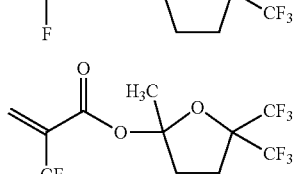
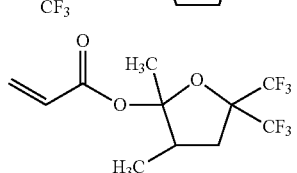
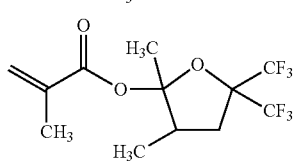
38
-continued
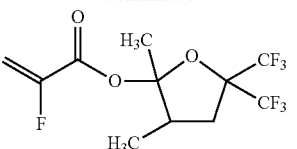
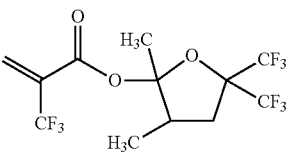
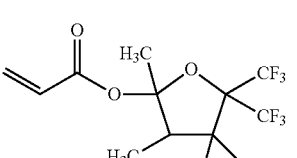
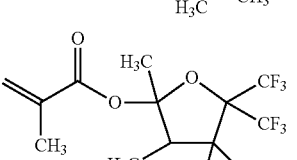
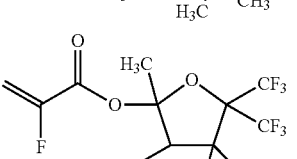
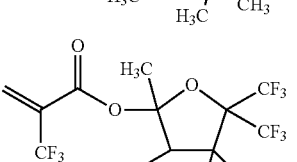
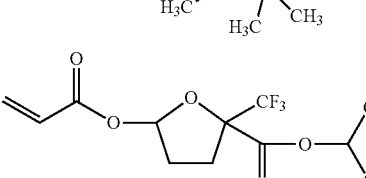
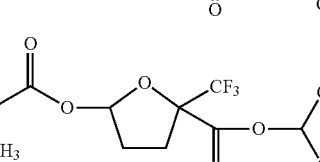
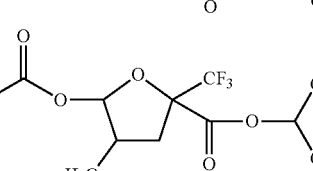
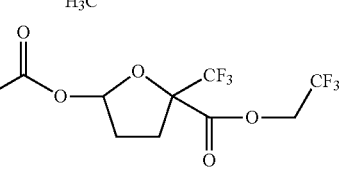

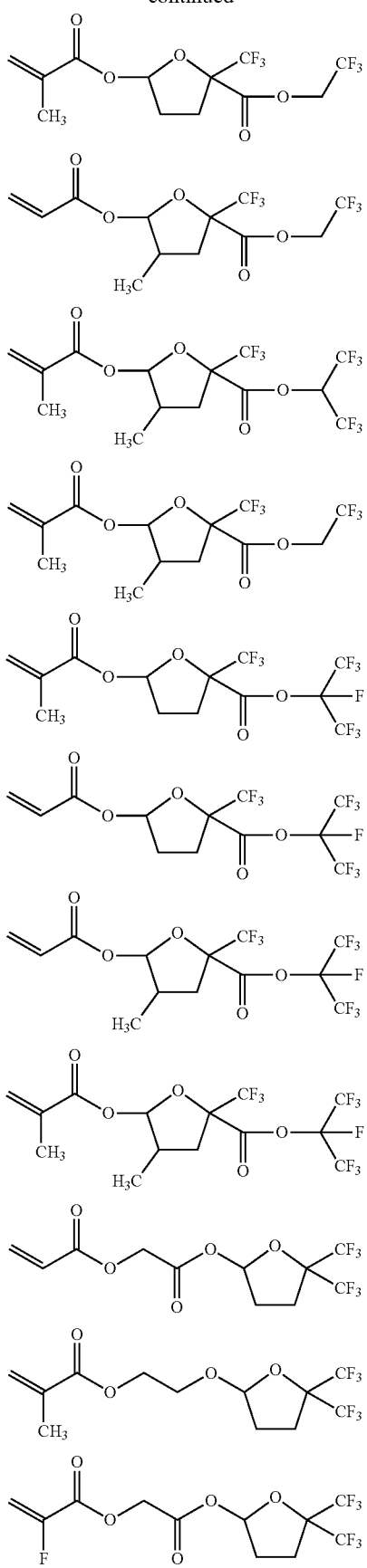
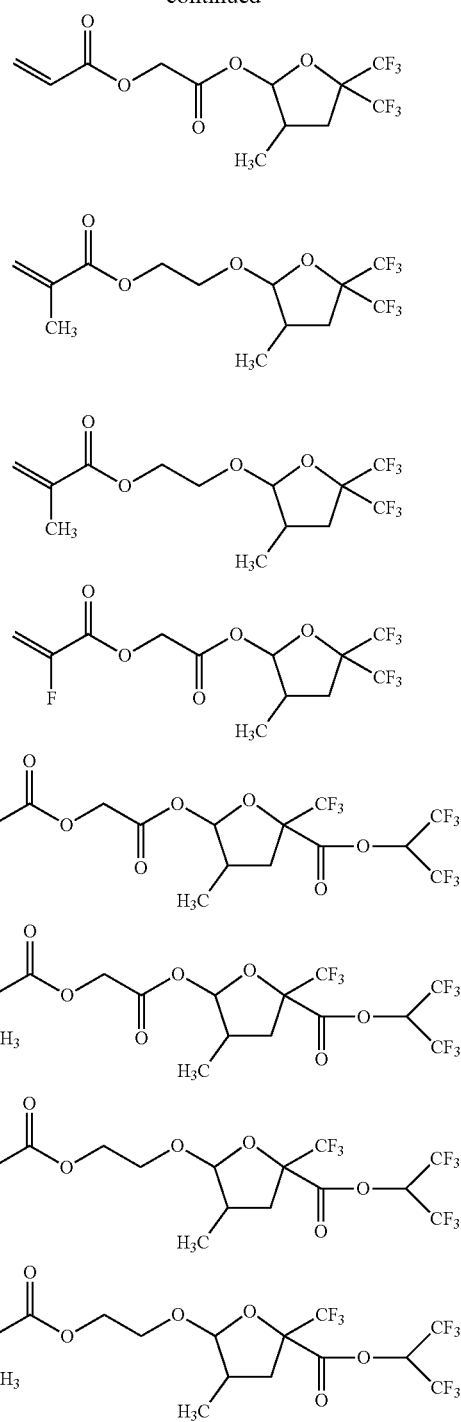

8. Production Method of Fluorine-Containing Monomer (4)

Next, an explanation will be given of a method for production of the fluorine-containing monomer (4) according to the present invention. In the present invention, the production method of the fluorine-containing monomer (4) includes formation of a cyclic hemiacetal compound of the following formula (7) by cyclization of a hydroxycarbonyl compound of the following formula (10) or a hydroxyvinyl ether or hydroxyvinyl ester of the following formula (11).

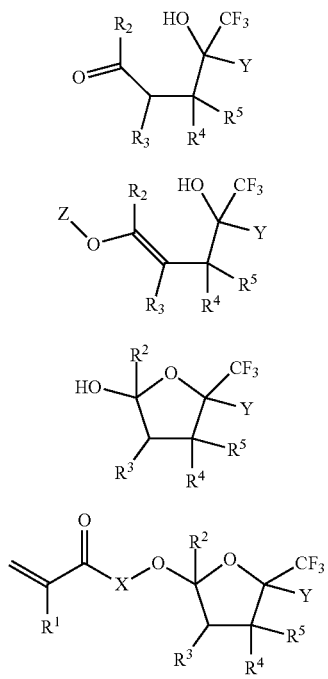

(10)

(11)

(7)

(4)

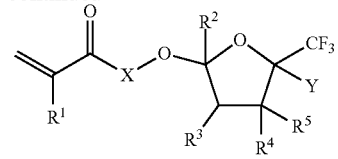

(4)

In the above formulas, $R^1$ is a hydrogen atom, a fluorine atom, or a $C_1$-$C_{10}$ linear or $C_3$-$C_{10}$ branched alkyl group in which seven or less of hydrogen atoms bonded to carbon atoms may be substituted with fluorine; $R^2$ to $R^3$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; X is a single bond, or a divalent group in which seven or less of hydrogen atoms may be substituted with fluorine; Y is a $C_1$-$C_3$ fluoroalkyl or carboxylate (—COOR) group in which seven or less of hydrogen atoms may be substituted with fluorine; R is a $C_1$-$C_3$ fluoroalkyl group; and Z is a hydrogen atom, or a $C_1$-$C_{20}$ liner or $C_3$-$C_{20}$ branched or cyclic alkyl group in which a part or all of hydrogen atoms may be substituted with fluorine and which may contain an ether bond, a siloxane bond, a thioether bond or a carbonyl bond. The same applies to the following.

8-1. Acylation or Alkylation of Fluorine-Containing Cyclic Hemiacetal Compound

The fluorine-containing monomer (4) is synthesized by introduction of a polymerizable group into the fluorine-containing cyclic hemiacetal compound of the formula (7) (hereinafter also referred to as "fluorine-containing cyclic hemiacetal compound (7)"). This reaction is shown in the follow scheme.

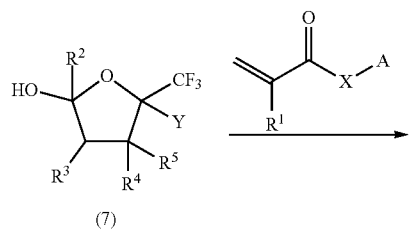

(7)

-continued (4)

In the scheme, $R^1$, $R^2$ to $R^5$, X and Y have the same definitions as those in the above scheme; and A is a hydrogen atom, a halogen atom, an acryloyl group or a methacryloyl group.

It is feasible to carry out this reaction by acylation or alkylation of a hydroxy group of the fluorine-containing cyclic hemiacetal compound (7). In other words, the fluorine-containing monomer (4) is obtained by reaction of the fluorine-containing cyclic hemiacetal compound with an acryloyl compound shown in the above reaction scheme, which serves as an acylation agent in the case where X is a single bond and as an alkylation agent in the case where X is a divalent organic group, in the presence of a base with or without the use of a solvent.

8-1-1. Acylation of Fluorine-Containing Cyclic Hemiacetal Compound

[Acylation Agent]

A carboxylic acid chloride or a carboxylic anhydride is usable as the acylation agent. Examples of the acylation agent include acrylic acid chloride, methacrylic acid chloride, acrylic anhydride, methacrylic anhydride, 2-fluoroacrylic acid chloride and 2-methacryloyloxyacetyl chloride.

The amount of the acylation agent used is preferably in the range of 0.5 mol to 10 mol per 1 mol of the fluorine-containing cyclic hemiacetal compound (7). In order for the acylation to proceed with high yield, the amount of the acylation agent used is more preferably in the range of 1 mol to 3 mol per 1 mol of the fluorine-containing cyclic hemiacetal compound (7). The acylation of the fluorine-containing cyclic hemiacetal compound with the acylation agent can be performed in the presence of a base and with or without the use of a solvent.

[Base]

The base can be an inorganic base or an organic base. For high reaction yield, the amount of the base used in the acylation reaction is preferably in the range of 0.05 mol to 10 mol, more preferably 1 mol to 3 mol, per 1 mol of the fluorine-containing cyclic hemiacetal compound (7).

<Inorganic Base>

Examples of the inorganic base include lithium hydroxide, sodium hydroxide, potassium hydroxide, barium hydroxide, sodium carbonate, potassium carbonate, sodium hydrogencarbonate and potassium hydrogencarbonate.

<Organic Base>

Examples of the organic base include trimethylamine, diisopropylethylamine, pyridine, imidazole, triethylenediamine, dimethylaminopyridine, and the like.

[Solvent]

As the solvent, there can be used a hydrocarbon solvent, an ether solvent or a chlorine-based solvent. The solvent may be used in combination with water as required.

<Hydrocarbon Solvent>

Examples of the hydrocarbon solvent include hexane, heptane, cyclohexane, methylcyclohexane, toluene and xylene.

<Ether Solvent>

Examples of the ether solvent include diethyl ether, dibutyl ether, tetrahydrofuran, 1,4-dioxane and ethylene glycol dimethyl ether.

<Chlorine-Based Solvent>

Examples of the chlorine-based solvent include methylene chloride, chloroform and 1,2-dichloroethylene.

8-1-2. Alkylation of Fluorine-Containing Cyclic Hemiacetal Compound

The polymerizable group can also be introduced by alkylation of a hydroxy group of the fluorine-containing cyclic hemiacetal compound (7) as mentioned above. In the alkylation reaction, a catalyst may be used for increase of reaction rate.

[Alkylation Agent]

An alkyl halide or a sulfonic acid ester is usable as the alkylation agent.

The alkylation reaction of the fluorine-containing cyclic hemiacetal compound with the alkylation agent can be performed in the presence of a base and with or without the use of a solvent. For high reaction yield, the amount of the alkylation agent used is preferably in the range of 0.5 mol to 10 mol, more preferably 1 mol to 3 mol, per 1 mol of the fluorine-containing cyclic hemiacetal compound (7).

<Alkyl Halide>

Examples of the alkyl halide include chloroethyl acrylate, chloroethyl methacrylate, bromoethyl acrylate and bromoethyl methacrylate.

<Sulfonic Acid Ester>

Examples of the sulfonic acid ester include 2-methylsulfonyloxyethyl acrylate, 2-methylsulfonyloxyethyl methacrylate, 2-p-tolunenesulfonyloxyethyl acrylate and 2-p-tolunenesulfonyloxyethyl methacrylate.

[Base]

The base can be an inorganic acid or an organic base. An organometallic salt is usable as the organic base. For high reaction yield, the amount of the base used in the reaction is preferably in the range of 0.05 mol to 10 mol, more preferably 1 mol to 3 mol.

<Inorganic Base>

Examples of the inorganic base include lithium hydroxide, sodium hydroxide, potassium hydroxide, barium hydroxide, sodium carbonate, potassium carbonate, sodium hydrogencarbonate, potassium hydrogencarbonate, lithium hydride, sodium hydride, potassium hydride and ammonia.

<Organic Base>

The organometallic salt can be an organic lithium salt, a Grignard reagent or an alkali metal salt.

Examples of the organic lithium salt include trimethylamine, diisopropylethylamine, pyridine, imidazole, triethylenediamine, dimethylaminopyridine, methyl lithium and n-butyl lithium.

Examples of the Grignard reagent include magnesium methyl bromide.

Examples of the alkali metal salt include sodium methoxide, sodium ethoxide and potassium t-butoxide.

[Solvent]

In general, the solvent is preferably of the kind suitable for nucleophilic substitution reaction. The solvent can be an aprotic polar solvent or a protic polar solvent.

A biphasic system of the solvent and water may be used.

Examples of the aprotic polar solvent include N,N-dimethylformamide, N,N-dimethylacetamide, dimethyl sulfoxide and N-methylpyrrolidone.

Examples of the protic polar solvent include acetone, methyl ethyl ketone, acetonitrile, propionitrile, diethyl ether, dibutyl ether, tetrahydrofuran, 1,4-dioxane, ethylene glycol dimethyl ether and dichloroethylene.

[Catalyst]

An iodide or bromide can be used as the catalyst in order to increase the reaction rate of the alkylation reaction. The amount of the catalyst used is preferably in the range of 0.001 to 1 mol, more preferably 0.005 to 0.5 mol, per 1 mol of the hemiacetal compound (7).

<Iodide>

Examples of the iodide include sodium iodide, lithium iodide and tetrabutylammonium iodide.

<Bromide>

Examples of the bromide include sodium bromide, lithium bromide and tetrabutylammonium bromide.

9. Fluorine-Containing Cyclic Hemiacetal Compound

[Fluorine-Containing Cyclic Hemiacetal Compound (7)]

In the present invention, the fluorine-containing polymer (1) is obtained by polymerization of the fluorine-containing monomer (4) as mentioned above. This fluorine-containing monomer has a fluorine-containing cyclic hemiacetal structure. The fluorine-containing cyclic hemiacetal compound (7) is a precursor of the fluorine-containing monomer (4).

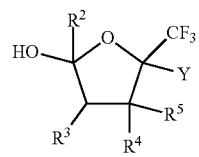

(7)

In the above formula (7), $R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; Y is a $C_1$-$C_3$ fluoroalkyl or carboxylate (—COOR) group in which seven or less of hydrogen atoms may be substituted with fluorine; and R is a $C_1$-$C_3$ fluoroalkyl group.

[Fluorine-Containing Cyclic Hemiacetal Compound (8)]

The fluorine-containing cyclic hemiacetal compound (7) is preferably a fluorine-containing cyclic hemiacetal compound of the following formula (8) corresponding to the case where $R^2$, $R^4$ and $R^5$ in the formula (7) are respectively hydrogen atoms.

In the present invention, the fluorine-containing polymer (2) is obtained by polymerization of the fluorine-containing monomer (5). This fluorine-containing monomer has a fluorine-containing cyclic hemiacetal structure. The fluorine-containing cyclic hemiacetal compound (8) is a precursor of the fluorine-containing monomer (5).

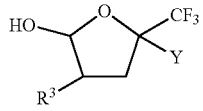

(8)

In the above formula (8), $R^3$ and X have the same definition as those in the formula (7).

[Fluorine-Containing Cyclic Hemiacetal Compound (9)]

The fluorine-containing cyclic hemiacetal compound (7) is further preferably a fluorine-containing cyclic hemiacetal compound of the following formula (9) corresponding to the case where Y in the formula (8) is a trifluoromethyl group.

In the present invention, the fluorine-containing polymer (3) is obtained by polymerization of the fluorine-containing monomer (6). This fluorine-containing monomer has a fluorine-containing cyclic hemiacetal structure. The fluorine-containing cyclic hemiacetal compound (9) is a precursor of the fluorine-containing monomer (6).

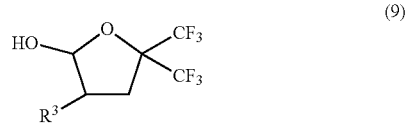

(9)

In the above formula (9), $R^3$ has the same definition as in the formula (7).

10. Production of Fluorine-Containing Cyclic Hemiacetal Compound (7)

An explanation will be given of a method for production of the fluorine-containing cyclic hemiacetal compound (7) according to the present invention.

In the present invention, the production method of the fluorine-containing cyclic hemiacetal compound includes cyclization of a hydroxycarbonyl compound of the formula (10) or a hydroxyvinyl ether or hydroxyvinyl ester of the formula (11) to the fluorine-containing cyclic hemiacetal compound of the formula (7).

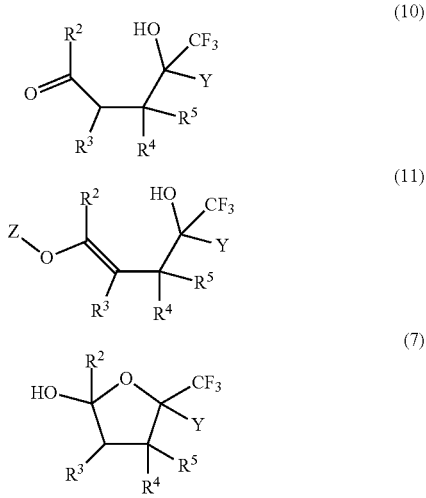

(10)

(11)

(7)

In the above formulas, $R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; Y is a $C_1$-$C_3$ fluoroalkyl or carboxylate (—COOR) group in which seven or less of hydrogen atoms may be substituted with fluorine; R is a $C_1$-$C_3$ fluoroalkyl group; and Z is a hydrogen atom, or a $C_1$-$C_{20}$ liner or $C_3$-$C_{20}$ branched or cyclic alkyl group in which a part or all of hydrogen atoms may be substituted with fluorine and which may contain an ether bond, a siloxane bond, a thioether bond or a carbonyl bond.

The fluorine-containing cyclic hemiacetal compound of the formula (7) can be principally obtained through the following two steps in the present invention.

10-1. First Step

In the first step, the hydroxycarbonyl compound of the formula (10) or the hydroxyvinyl ether or ester of the formula (11) is formed by carbonyl-ene reaction of an allyl alcohol, allyl ether or allyl ester with a trifluoropyruvic acid ester or hexafluoroacetone (hereinafter also referred to as "HFA").

The carbonyl-ene reaction of an allyl alcohol, allyl ether or allyl ester of the formula (12) with a trifluorocarbonyl compound of the formula (13) for formation of the hydroxycarbonyl compound of the formula (10) or the hydroxyvinyl ether or hydroxyvinyl ester of the formula (11) is shown below. Hereinafter, the hydroxycarbonyl compound of the formula (10), the hydroxyvinyl ether or hydroxyvinyl ester of the formula (11), the allyl alcohol, allyl ether or allyl ester of the formula (12) and the trifluorocarbonyl compound of the formula (13) are also referred to as "hydroxycarbonyl compound (10)", "hydroxyvinyl ether or ester (11)", "allyl alcohol, ether or ester (12)" and "trifluorocarbonyl compound (13)", respectively.

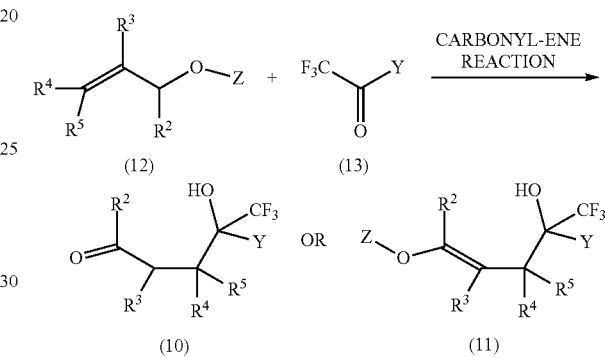

In the above formulas, $R^1$ is a hydrogen atom, a fluorine atom, or a $C_1$-$C_{10}$ linear or $C_3$-$C_{10}$ branched alkyl group in which seven or less of hydrogen atoms bonded to carbon atoms may be substituted with fluorine; $R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; Y is a $C_1$-$C_3$ fluoroalkyl or carboxylate (—COOR) group in which seven or less of hydrogen atoms may be substituted with fluorine; R is a $C_1$-$C_3$ fluoroalkyl group; Z is a hydrogen atom, or a $C_1$-$C_{20}$ liner or $C_3$-$C_{20}$ branched or cyclic alkyl group in which a part or all of hydrogen atoms may be substituted with fluorine and which may contain an ether bond, a siloxane bond, a thioether bond or a carbonyl bond.

It is feasible to selectively form the hydroxycarbonyl compound (10) or hydroxyvinyl ether or ester (11) by mixing the allyl alcohol (12) in which Z is a hydrogen atom, or the allyl ether or ester (12) in which Z is an alkyl group due to protection of a hydroxy group, with HFA in which Y is a trifluoromethyl group, and then, reacting the resulting mixture in a closed pressurized system such as autoclave optionally with heating. The reaction proceeds efficiently even in the case where the trifluoropyruvic acid ester is used in place of HFA.

This reaction is ene reaction of an allyl moiety of the allyl alcohol, ether or ester (12) with the fluorocarbonyl compound (13). The higher the electron density of the olefin moiety of the allyl alcohol, ether or ester (12), the more likely the ene reaction is to proceed. The ene reaction is carried out selectively with less side reaction when the electron density of the olefin moiety of the allyl alcohol, ether or ester is high. For this reason, it is preferable in the allyl alcohol, ether or ester (12) that one or more of $R^2$ to $R^5$ are substituted with an electron-donating group as compared to the case where all of $R^2$ to $R^5$ are hydrogen atoms. As the electron-donating group, a methyl group is preferred.

The amount of the HFA or trifluoropyruvic acid ester used is preferably in the range of 0.5 mol to 10 mol, more preferably 1 mol to 3 mol, per 1 mol of the allyl alcohol, ether or ester (12).

[Allyl Alcohol]

Examples of the allyl alcohol (12) in which Z is a hydrogen atom include allyl alcohol, β-methylallyl alcohol, 1-buten-3-ol, crotyl alcohol and 3-methyl-2-buten-1-ol.

[Allyl Ether or Allyl Ester]

Examples of the allyl ether or ester (12) in which Z is a group other than hydrogen include those obtained by introduction of a protecting group to a hydroxy group of the above allyl alcohol (12). As the protecting group, there can be used a silyl group, an acetal group, an acyl group, a benzyl group or a carbamate group. The protecting group is preferably an acetal group, a silyl group, a carbamate group or a benzyl group to increase the electron density of the olefin moiety and to promote the reaction.

<Silyl Group>

Examples of the silyl group include trimethylsilyl, triethylsilyl, tributylsilyl, t-butyldimethylsilyl and t-butyldiphenylsilyl.

<Acetal Group>

Examples of the acetal group include tetrahydropyranyl, ethoxyethyl, butoxyethyl, methoxymethyl, methylthiomethyl, benzyloxymethyl and methoxyethoxymethyl.

<Acyl Group>

Examples of the acyl group include formyl, acetyl, trifluoroacetyl, propionyl, benzoyl, pivaloyl, acrylyl and methacrylyl.

<Benzyl Group>

Examples of the benzyl group include benzyl and p-methoxybenzyl.

<Carbamate Group>

Examples of the carbamate group include t-butoxycarbonyl and benzyloxycarbonyl.

10-2. First Step

The reaction of the first step proceeds with or without the use of a solvent. In order to promote the reaction, the reaction can be performed with the use of an acid catalyst in a solvent. For lower-cost production, it is preferable to perform the reaction with the use of no solvent and no catalyst, and then, isolate the hydroxycarbonyl compound of the formula (10) or the hydroxyvinyl ether or ester of the formula (11) from the reaction product by purification operation such as distillation.

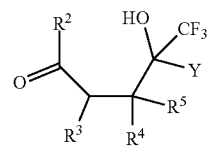
(10)

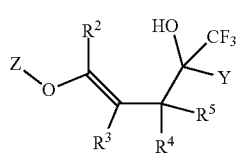
(11)

There is no particular limitation on whether the catalyst is used or not in the reaction. In the case of using the catalyst, either an inorganic acid, an organic acid or a Lewis acid is usable as the catalyst.

Examples of the inorganic acid include hydrochloric acid, sulfuric acid, nitric acid, phosphoric acid, boric acid and zeolite. As the organic acid, there can be used a carboxylic acid, a sulfonic acid, a cation exchange resin or a Lewis acid. Examples of the carboxylic acid include formic acid, acetic acid and trifluoroacetic acid. Examples of the sulfonic acid include methanesulfonic acid, triflouromethanesulfonic acid, benzenesulfonic acid and p-toluenesulfonic acid. Examples of the Lewis acid include aluminium chloride, titanium tetrachloride and tin chloride.

The reaction proceeds without the use of the solvent as mentioned above. In the case of using the solvent, the solvent is preferably of the kind inert to the reaction raw materials such as allyl alcohol, ether or ester (12) and HFA or trifluoropyruvic acid ester (13) and to the target fluorine-containing compound of the formula (10) or (11). As such a solvent, there can be used an aliphatic hydrocarbon, an aromatic hydrocarbon, a halogenated hydrocarbon or an ether.

[Aliphatic Hydrocarbon]

Examples of the aliphatic hydrocarbon include hexane, heptane, cyclohexane, cyclic aliphatic hydrocarbons such as methylcyclohexane, and the like.

[Aromatic Hydrocarbon]

Examples of the aromatic hydrocarbon include benzene, toluene and xylene.

[Halogenated Hydrocarbon]

Examples of the halogenated hydrocarbon include methylene chloride.

[Ether]

Examples of the ether include diethyl ether, dibutyl ether, tetrahydrofuran and ethylene glycol dimethyl ether.

10-3. Second Step

In the second step, the hydroxycarbonyl compound of the formula (10) or the hydroxyvinyl ether or hydroxyvinyl ester of the formula (11) is subjected to intramolecular cyclization and thereby converted to the cyclic hemiacetal compound (7).

The reaction process varies depending on the kind and substituents of the product in the first step. Principally, the following three processes (process 1 to process 3) are possible.

10-3-1. Process 1

The process 1 is to form the fluorine-containing cyclic hemiacetal compound (7) by selective intermolecular cyclization of the hydroxycarbonyl compound (10) in a solvent under the action of an acid or base as shown in the following reaction scheme.

PROCESS 1

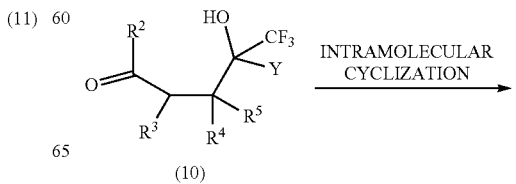

-continued

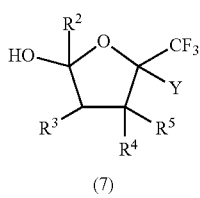

(7)

In this process, it is preferable to perform the reaction in the solvent under acidic conditions or basic conditions.

The acid can be an inorganic acid, an organic acid or a Lewis acid. The amount of the acid used in the reaction is preferably in the range of 0.01 mol to 1 mol, more preferably 0.05 mol to 0.2 mol, per 1 mol of the hydroxycarbonyl compound (10).

The base can be an inorganic base or an organic base. It is preferable to use the base, in particular, sodium hydroxide or potassium hydroxide in an organic solvent-water biphasic system which is capable of removing an unreacted reaction raw material and a slightly contained fluorine-containing alcohol. The amount of the base used in the reaction is preferably in the range of 0.5 mol to 10 mol per 1 mol of the hydroxycarbonyl compound (10). For higher reaction yield, the amount of the base used is more preferably in the range of 1 mol to 3 mol per 1 mol of the hydroxycarbonyl compound (10).

[Inorganic Acid]

Examples of the inorganic acid include hydrochloric acid, sulfuric acid, nitric acid, phosphoric acid, boric acid and zeolite.

[Organic Acid]

As the organic acid, there can be used a carboxylic acid, a sulfonic acid, a cation exchange resin or a Lewis acid. Examples of the carboxylic acid include formic acid, acetic acid and trifluoroacetic acid. Examples of the sulfonic acid include methanesulfonic acid, triflouromethanesulfonic acid, benzenesulfonic acid and p-toluenesulfonic acid. Examples of the Lewis acid include aluminium chloride, titanium tetrachloride and tin chloride.

[Inorganic Base]

Examples of the inorganic base include lithium hydroxide, sodium hydroxide, potassium hydroxide, barium hydroxide, sodium carbonate, potassium carbonate, sodium hydrogencarbonate, potassium hydrogencarbonate, lithium hydride, sodium hydride, potassium hydride and ammonia.

[Organic Base]

As the organic base, there can be used an organic lithium salt, a Grignard reagent or an organic alkali metal salt.

Examples of the organic lithium salt include trimethylamine, diisopropylethylamine, pyridine, imidazole, triethylenediamine, dimethylaminopyridine, methyl lithium and n-butyl lithium. Examples of the Grignard reagent include magnesium methyl bromide. Examples of the organic alkali metal salt include sodium methoxide, sodium ethoxide and potassium t-butoxide.

[Solvent]

The reaction proceeds without the use of the solvent as mentioned above. In the case of using the solvent, the solvent is preferably of the kind inert to the reaction raw material, that is, the hydroxycarbonyl compound (10) and to the target fluorine-containing cyclic hemiacetal (7). As such a solvent, there can be used water, an alcohol, an aliphatic hydrocarbon, an aromatic hydrocarbon, a halogenated hydrocarbon or an ether.

Examples of the aliphatic hydrocarbon include hexane, heptane, cyclohexane, cyclic aliphatic hydrocarbons such as methylcyclohexane, and the like. Examples of the aromatic hydrocarbon include benzene, toluene and xylene. Examples of the halogenated hydrocarbon include methylene chloride. Examples of the ether include diethyl ether, dibutyl ether, tetrahydrofuran and ethylene glycol dimethyl ether.

10-3-2. Process 2

The process 2 is to convert the hydroxyvinyl ether or ester (11) to a hydroxycarbonyl compound by deprotection, and then, perform selective intermolecular cyclization of the hydroxycarbonyl compound by picking up a hydrogen atom from a hydroxy group of the hydroxycarbonyl compound in a solvent under the action of an acid or base, to thereby form the fluorine-containing cyclic hemiacetal compound (7) as shown in the following reaction scheme.

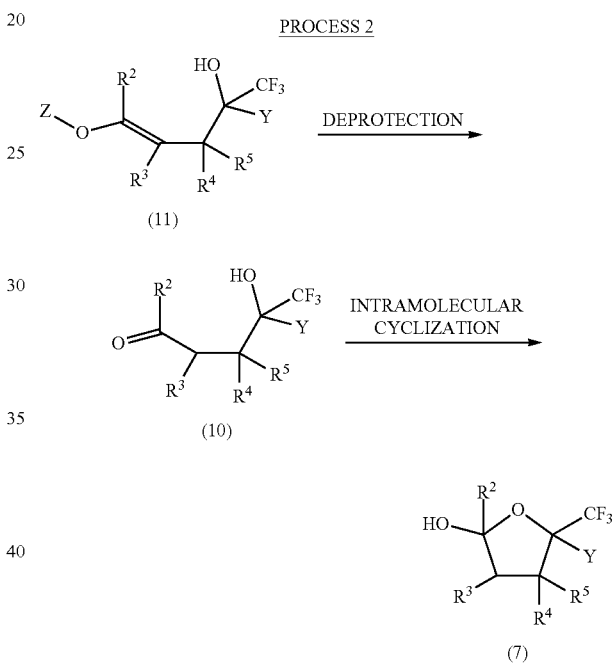

Since the hydroxyvinyl ether or ester (11) is a protected hydroxy compound, the hydroxyvinyl ether or ester (11) is converted to the hydroxycarbonyl compound (10) by deprotecting the protecting group of the hydroxyvinyl ether or ester (11). After the deprotection, the hydroxycarbonyl compound (10) is subjected to intermolecular cyclization in the same manner as in the process 1, whereby the fluorine-containing cyclic hemiacetal compound (7) is obtained. The deprotection can be performed by an ordinary deprotection technique. The acid or base and solvent usable in this process are the same as those in the process 1.

10-3-3. Process 3

The process 3 is to perform selective intermolecular cyclization of the hydroxyvinyl ether or ester (11) by picking up a hydrogen atom from a hydroxy group of the hydroxyvinyl ether or ester in a solvent under the action of an acid or base, and then, convert the resulting fluorine-containing cyclic hemiacetal intermediate (14) to the fluorine-containing cyclic hemiacetal compound (7) by deprotection as shown in the following reaction scheme.

PROCESS 3

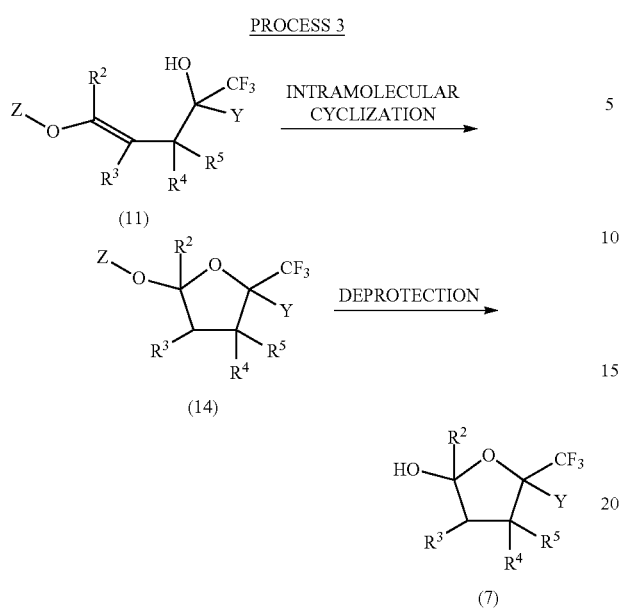

(11) → (14) → (7)

[Intermolecular Cyclization]

The fluorine-containing cyclic hemiacetal intermediate of the formula (14) is formed by, in the absence of a solvent or in a solvent with the addition of an acid catalyst, heating the hydroxyvinyl ether or ester (11) to about the boiling point of the solvent.

It is particularly preferable to use trifluoroacetic acid, methanesulfonic acid or sulfuric acid for high-yield production of the fluorine-containing cyclic hemiacetal intermediate (14). The amount of the acid used in the reaction is preferably in the range of 0.01 mol to 1 mol, more preferably 0.05 mol to 0.2 mol, per 1 mol of the hydroxyvinyl ether or ester (11).

[Acid]

In the process 3, either an inorganic acid, an organic acid or a Lewis acid is usable as the acid.

<Inorganic Acid>

Examples of the inorganic acid include hydrochloric acid, sulfuric acid, nitric acid, phosphoric acid, boric acid and zeolite.

<Organic Acid>

The organic acid can be a carboxylic acid, a sulfonic acid, a cation exchange resin or a Lewis acid.

Examples of the carboxylic acid include formic acid, acetic acid and trifluoroacetic acid. Examples of the sulfonic acid include methanesulfonic acid, triflouromethanesulfonic acid, benzenesulfonic acid and p-toluenesulfonic acid. Examples of the Lewis acid include aluminium chloride, titanium tetrachloride and tin chloride.

[Deprotection]

The fluorine-containing cyclic hemiacetal intermediate (14) is a derivative of the fluorine-containing cyclic hemiacetal compound (7) in which a hydroxy group is protected by another substituent group. The fluorine-containing cyclic hemiacetal compound (7) is formed by deprotecting the protecting group of the fluorine-containing cyclic hemiacetal intermediate (14). The deprotection can be performed by an ordinary deprotection technique.

In the case of a fluorine-containing compound (15) that corresponds to the case where Z of the hydroxyvinyl ether (11) has a polymerizable group, on the other hand, the fluorine-containing monomer (4) is obtained by the first intermolecular cyclization stage of the process 3 as shown in the following reaction scheme.

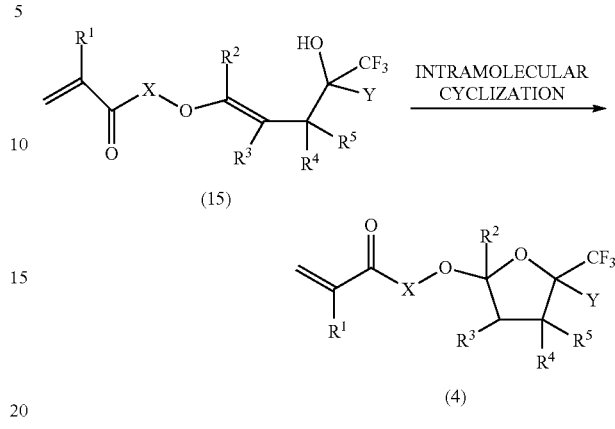

(15) → (4)

EXAMPLES

The present invention will be described in more detail below by way of the following examples and comparative examples. It should however be understood that the present invention is not limited to the following examples.

1. Synthesis of Fluorine-Containing Cyclic Hemiacetals

Fluorine-containing cyclic hemiacetals 1 to 7, each of which belongs to the fluorine-containing cyclic hemiacetal compound of the formula (7) as a precursor for formation of the fluorine-containing monomer (4), were synthesized by the following methods.

1-1-1. Synthesis of Fluorine-Containing Cyclic Hemiacetal 1 (Synthesis Example 1).

In a reactor with a stirrer, 1.6 g (0.2 mol) of allyl alcohol (available from Tokyo Chemical Industry Co., Ltd.) was put. The reactor was closed and evacuated by a vacuum pump. Subsequently, 66.4 g (0.40 mol) of HFA was introduced into the reactor while the contents of the reactor were stirred with the stirrer. The inside temperature of the reactor was raised to 150° C. Then, the contents of the reactor were kept stirred for 40 hours. After the completion of the reaction, the resulting reaction mixture was taken out of the reactor and put into a separatory funnel. To the reaction mixture, 50 ml of 3.5 mass % hydrochloric acid was added. The thus-obtained mixture was stirred for 2 hours and then separated into an organic layer and an aqueous layer. The organic layer was admixed with 50 ml of an aqueous solution of 4 mass % sodium hydroxide, followed by stirring the admixture for 1 hour. After that, the organic layer was separated and subjected to vacuum distillation under the conditions of a pressure of 3.0 kPa and a temperature of 60 to 62° C. As a result, 22.4 g of the following fluorine-containing cyclic hemiacetal 1 was obtained. The yield of the hemiacetal was 50%. This synthesis reaction process is as shown below.

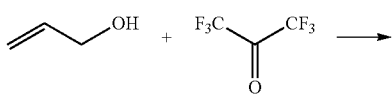

-continued

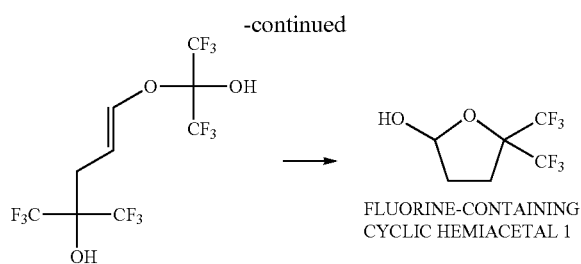

FLUORINE-CONTAINING CYCLIC HEMIACETAL 1

<NMR Analysis Results>

The nuclear magnetic resonance (NMR) analysis results of the hemiacetal are shown below.

$^1$H-NMR (solvent: deuterated chloroform, standard substance: TMS) δ (ppm) 2.32-2.59 (2H, m), 2.65-2.78 (2H, m), 4.11 (1H, br), 6.20 (1H, d)

$^{19}$F-NMR (solvent: deuterated chloroform, standard substance: $C_6D_6$) δ (ppm) −77.5 (3F, s), −79.5 (3F, s)

1-1-2. Synthesis of Fluorine-Containing Cyclic Hemiacetal 1 (Synthesis Example 2)

In a reactor with a stirrer, 11.6 g (0.2 mol) of allyl alcohol and 0.2 g (0.0002 mol) of methanesulfonic acid were put. The reactor was closed and evacuated by a vacuum pump. Subsequently, 66.4 g (0.40 mol) of HFA was introduced into the reactor while the contents of the reactor was stirred with the stirrer. The inside temperature of the reactor was raised to 120° C. Then, the contents of the reactor were kept stirred for 20 hours. After the completion of the reaction, the resulting reaction mixture was taken out of the reactor and put into a separatory funnel. To the reaction mixture, 50 ml of an aqueous solution of 4 mass % sodium hydroxide was added. The thus-obtained mixture was stirred for 1 hour and separated into two layers. The organic layer was recovered and subjected to vacuum distillation under the conditions of a pressure of 3.0 kPa and a temperature of 60 to 62° C. As a result, 28 g of the following fluorine-containing cyclic hemiacetal 1 was obtained. The yield of the hemiacetal was 63%. This synthesis reaction process is as shown below.

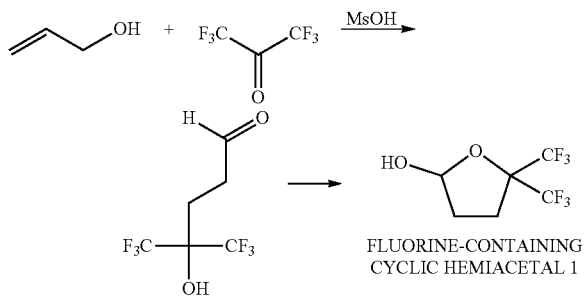

FLUORINE-CONTAINING CYCLIC HEMIACETAL 1

1-2. Synthesis of Fluorine-Containing Cyclic Hemiacetal 2

In a reactor with a stirrer, 14.4 g (0.2 mol) of β-methallyl alcohol (available from Tokyo Chemical Industry Co., Ltd.) was put. The reactor was closed and evacuated by a vacuum pump. Subsequently, 66.4 g (0.40 mol) of HFA was introduced into the reactor while the contents of the reactor were stirred with the stirrer. The inside temperature of the reactor was raised to 40° C. Then, the contents of the reactor were kept stirred for 2 hours. After the completion of the reaction, the resulting reaction mixture was taken out of the reactor and put into a separatory funnel. To the reaction mixture, 50 ml of 3.5 mass % hydrochloric acid was added. The thus-obtained mixture was stirred for 2 hours and then separated into an organic layer and an aqueous layer. The organic layer was admixed with 50 ml of an aqueous solution of 4 mass % sodium hydroxide, followed by stirring the admixture for 1 hour. After that, the organic layer was separated and subjected to vacuum distillation under the conditions of a pressure of 3.0 kPa and a temperature of 68 to 69° C. As a result, 43.7 g of the following fluorine-containing cyclic hemiacetal 2 was obtained. The yield of the hemiacetal was 92%. This synthesis reaction process is as shown below.

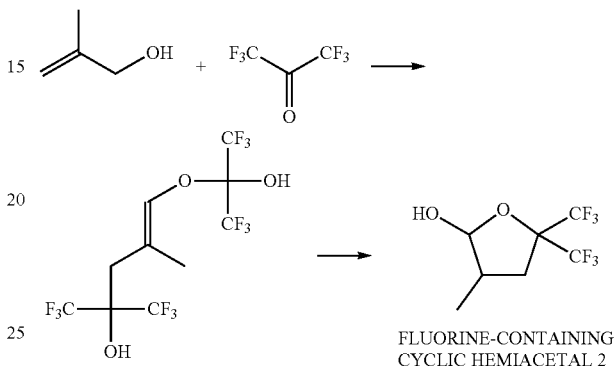

FLUORINE-CONTAINING CYCLIC HEMIACETAL 2

<NMR Analysis Results>

$^1$H-NMR (solvent: deuterated chloroform, standard substance: TMS) δ (ppm)

Isomer 1: 1.14 (3H, d), 1.93-2.05 (1H, m), 2.40 (2H, dd), 3.80 (1H, d), 5.19 (1H, d)

Isomer 2: 1.10 (3H, d), 2.18 (1H, dd), 2.2-2.5 (1H, m), 2.55 (1H, dd), 3.25 (1H, d), 5.55 (1H, d)

$^{19}$F-NMR (solvent: deuterated chloroform, standard substance: $C_6D_6$) δ (ppm) −77.5 (3F, m), −79.5 (3F, m)

1-3. Synthesis of Fluorine-Containing Cyclic Hemiacetal 3

The reaction shown below was performed in the same manner as in the synthesis of the fluorine-containing cyclic hemiacetal 2, except that 2-methyl-3-buten-2-ol (available from Tokyo Chemical Industry Co., Ltd.) was used in place of the β-methallyl alcohol used in the synthesis of the fluorine-containing cyclic hemiacetal 2. As a result, the following fluorine-containing cyclic hemiacetal 3 was obtained with a yield of 87%.

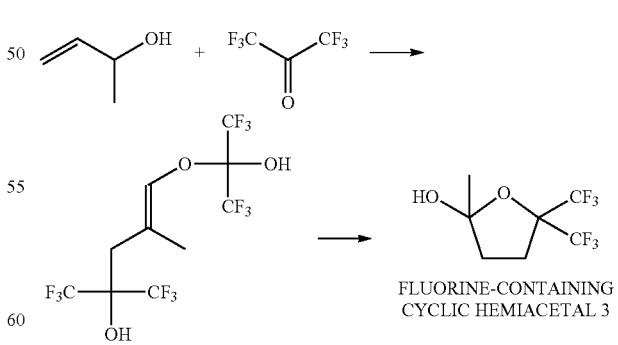

FLUORINE-CONTAINING CYCLIC HEMIACETAL 3

1-4. Synthesis of Fluorine-Containing Cyclic Hemiacetal 4

The reaction shown below was performed in the same manner as in the synthesis of the fluorine-containing cyclic hemiacetal 2, except that crotyl alcohol (available from Tokyo Chemical Industry Co., Ltd.) was used in place of the β-methallyl alcohol used in the synthesis of the fluorine-containing cyclic hemiacetal 2. As a result, the following fluorine-containing cyclic hemiacetal 4 was obtained with a yield of 75%.

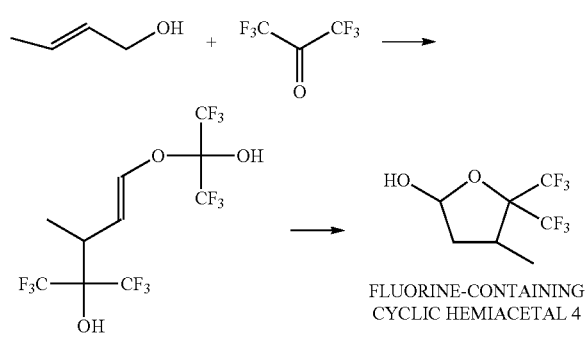

1-5. Synthesis of Fluorine-Containing Cyclic Hemiacetal 5

The reaction shown below was performed in the same manner as in the synthesis of the fluorine-containing cyclic hemiacetal 2, except that 3-methyl-2-buten-1-ol (available from Tokyo Chemical Industry Co., Ltd.) was used in place of the β-methallyl alcohol used in the synthesis of the fluorine-containing cyclic hemiacetal 2. As a result, the following fluorine-containing cyclic hemiacetal 5 was obtained with a yield of 65%.

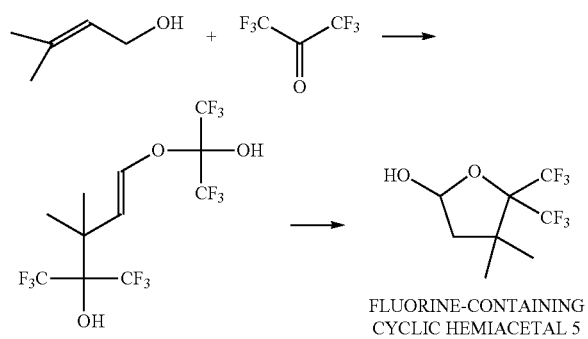

1-6. Synthesis of Fluorine-Containing Cyclic Hemiacetal 6

In a 100-ml glass flask with a stirrer, 1.86 g (0.01 mol) of βmetallyl-t-butyldimethylsilyl ether, which had previously been prepared by protecting β-metallyl alcohol with t-butyldimethylsilyl according to a predetermined method, was mixed with 2.92 g (0.01 mol) of separately prepared 1,1,1,3,3,3-hexafluoroisopropyl trifluoropyruvate. The inside temperature of the flask was raised to 50° C. Then, the contents of the flask were kept stirred for 18 hours. After the completion of the reaction, the resulting reaction mixture was taken out of the flask and put into a separatory funnel. To the reaction mixture, 10 ml of 3.5 mass % hydrochloric acid was added. The thus-obtained mixture was stirred for 2 hours and then separated into an organic layer and an aqueous layer. The organic layer was admixed with 10 ml of an aqueous solution of 4 mass % sodium hydroxide, followed by stirring the admixture for 1 hour. The organic layer was recovered and subjected to separation by silica gel column chromatography. As a result, 19.0 g of the following fluorine-containing cyclic hemiacetal 6 was obtained. The yield of the hemiacetal was 52%. This reaction process is as shown below.

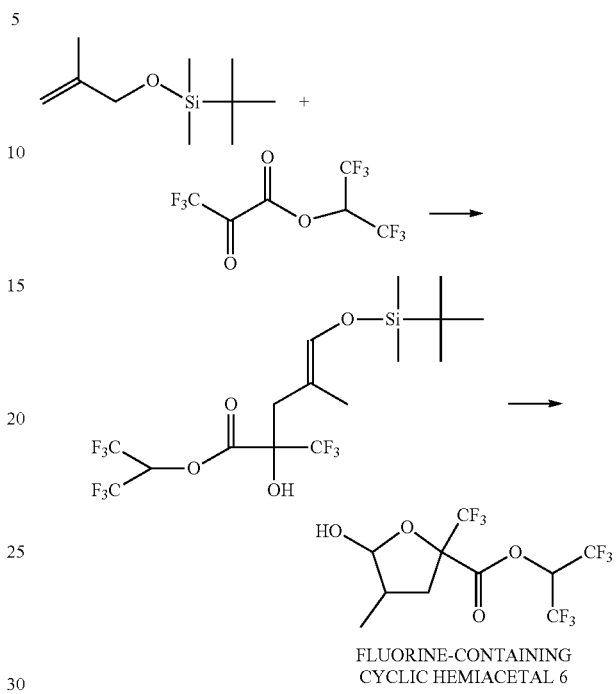

<NMR Analysis Results>
$^1$H-NMR (solvent: deuterated chloroform, standard substance: TMS) δ (ppm)
Isomer 1: 1.17 (3H, d), 1.97-2.11 (1H, m), 2.45 (2H, dd), 3.81 (1H, d), 5.25 (1H, d), 5.68 (1H, m)
Isomer 2: 1.11 (3H, d), 2.22 (1H, dd), 2.25-2.53 (1H, m), 2.65 (1H, dd), 3.30 (1H, d), 5.60 (1H, d), 5.68 (1H, m)
$^{19}$F-NMR (solvent: deuterated chloroform, standard substance: $C_6D_6$) δ (ppm) −77.1 (6F, m), −78.5 (3F, m)

[Preparation of 1,1,1,3,3,3-Hexafluoroisopropyl Trifluoropyruvate]

The method for preparation of the 1,1,1,3,3,3-hexafluoroisopropyl trifluoropyruvate used in the synthesis of the fluorine-containing cyclic hemiacetal 6 was as follows.

In a 100-ml glass flask with a stirrer, 17.0 g (0.1 mol) of ethyl trifluoropyruvate (available under the trade name of E-TFPA from Central Glass Company, Ltd.) and 50 ml of an aqueous solution of 10 mass % sodium hydroxide were put. The mixture inside the flask was stirred for 2 hours and concentrated under reduced pressure. After ethanol was evaporated from the mixture, the mixture was neutralized with the addition of 55 ml of 10 mass % hydrochloric acid. Subsequently, 30 ml of dichloromethane was added to the mixture so that trifluoropyruvic acid formed was extracted into a dichloromethane layer. The dichloromethane solution was separated. Water was removed from the dichloromethane solution with the use of a drying agent. Then, 16.2 g (0.1 mol) of CDI (carbonyldiimidazole) (available from Wako Pure Chemical Corporation) was added to the dichloromethane solution. The resulting liquid was stirred for 1 hour at room temperature, admixed with 16.8 g (0.1 mol) of HFIP (available from Central Glass Company, Ltd.) and further stirred for 2 hours. The reaction liquid was admixed with 30 ml of 3.5 mass % hydrochloric acid and washed twice with 30 ml of pure water. The thus-formed organic layer was separated and subjected to vacuum distillation under the conditions of kPa and a temperature of 65° C. As a result, 16 g of 1,1,1,3,3,3-hexafluoroisopropyl trifluoropyruvate was obtained. The yield of the target product was 55%. This reaction process is as shown below.

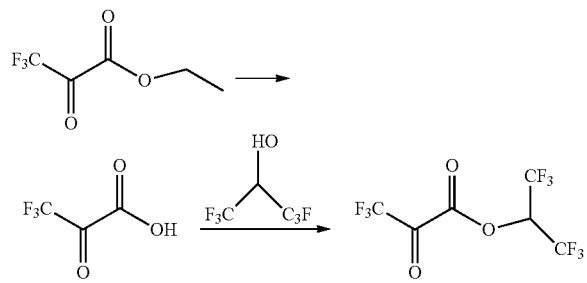

<NMR Analysis Results>
$^1$H-NMR (solvent: deuterated chloroform, standard substance: TMS) δ (ppm) 5.65 (1H, m)
$^{19}$F-NMR (solvent: deuterated chloroform, standard substance: $C_6D_6$) δ (ppm) −76.6 (6F, s), −83.1 (3F, s)

1-7. Synthesis of Fluorine-Containing Cyclic Hemiacetal 7

The reaction shown below was performed in the same manner as in the synthesis of the fluorine-containing cyclic hemiacetal 6, except that separately prepared 2,2,2-trifluoroethyl trifluoropyruvate was used in place of the 1,1,1,3,3,3-hexafluoroisopropyl trifluoropyruvate used in the synthesis of the fluorine-containing cyclic hemiacetal 6. As a result, the following fluorine-containing cyclic hemiacetal 7 was obtained with a yield of 61%.

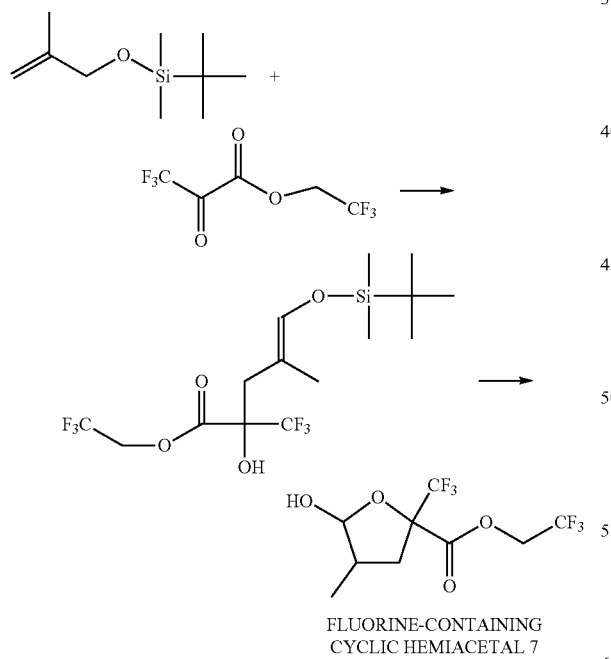

FLUORINE-CONTAINING CYCLIC HEMIACETAL 7

[Preparation of 2,2,2-Trifluoroethyl Trifluoropyruvate]

The method for preparation of the 2,2,2-trifluoroethyl trifluoropyruvate used in the synthesis of the fluorine-containing cyclic hemiacetal 7 was as follows.

In a 100-ml glass flask with a stirrer, the dichloromethane solution of trifluoropyruvic acid was provided as mentioned in the above preparation example. Then, 16.2 g (0.1 mol) of CDI (carbonyldiimidazole) was added to the dichloromethane solution. The resulting liquid was stirred for 1 hour at room temperature. The liquid was admixed with 10.0 g (0.1 mol) of 2,2,2-trifluoroethanol (available from Wako Pure Chemical Corporation) and further stirred for 2 hours. The reaction liquid was admixed with 30 ml of 3.5 mass % hydrochloric acid and washed twice with 30 ml of pure water. The thus-formed organic layer was separated and subjected to vacuum distillation under the conditions of a pressure of 30 kPa and a temperature of 65° C. As a result, 11 g of 2,2,2-trifluoroethyl trifluoropyruvate was obtained. The yield of the target product was 50%/a. This reaction process is as shown below.

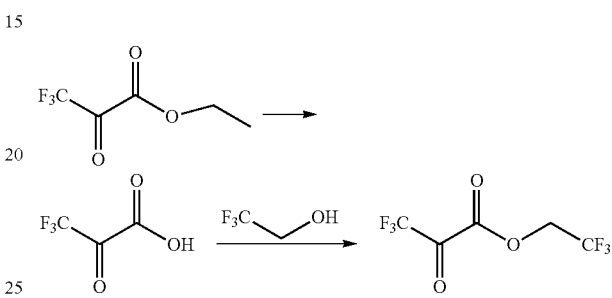

2. Synthesis of Fluorine-Containing Monomers

Some kinds of the fluorine-containing monomer (4) were synthesized using the fluorine-containing cyclic hemiacetals 1, 2, 6 and 7 as the fluorine-containing cyclic hemiacetal compound of the formula (7).

2-1. Synthesis of Fluorine-Containing Monomer 1

In a 300-ml glass flask with a stirrer, 22.4 g (0.1 mol) of the fluorine-containing cyclic hemiacetal 1, 15.1 g (0.15 mol) of trimethylamine and methoxyphenol (1000 ppm) as a polymerization inhibitor were put. While the inside temperature of the flask was maintained at 30° C. or lower, 16.9 g (0.11 mol) of methacrylic anhydride was dropped into the flask. The resulting mixture was stirred for 2 hours. To the mixture, 40 ml of diisopropyl ether and 30 ml of pure water were added. The mixture was stirred and then subjected to separation. The separated organic layer was admixed with 20 ml of an aqueous solution of 1 wt % sodium hydroxide, stirred for 1 hour and subjected to separation. The separated organic layer was washed twice with 30 ml of pure water and then subjected to vacuum distillation under the conditions of a pressure of 1.1 kPa and a temperature of 70 to 72° C. As a result, the following fluorine-containing monomer 1 was obtained with a yield of 85%. This reaction process is as shown below.

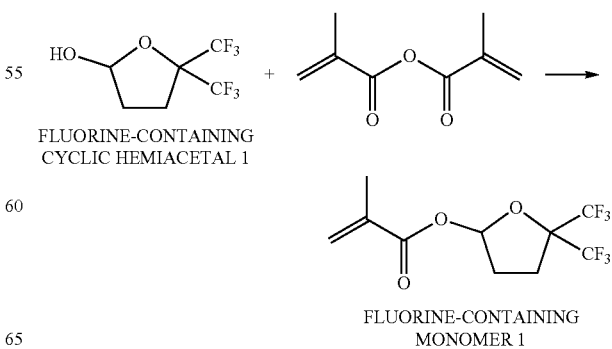

FLUORINE-CONTAINING CYCLIC HEMIACETAL 1

FLUORINE-CONTAINING MONOMER 1

<NMR Analysis Results>

$^1$H-NMR (solvent: deuterated chloroform, standard substance: TMS) δ (ppm) 1.92 (3H, s), 2.32-2.59 (2H, m), 2.72-2.89 (2H, m), 5.65 (1H, q), 6.12 (1H, q), 6.68 (1H, d)

$^{19}$F-NMR (solvent: deuterated chloroform, standard substance: $C_6D_6$) δ (ppm) −77.5 (3F, s), −79.5 (3F, s)

2-2. Synthesis of Fluorine-Containing Monomer 2

The reaction shown below was performed in the same manner as in the synthesis of the fluorine-containing monomer 1, except that the fluorine-containing cyclic hemiacetal 2 was used in place of the fluorine-containing cyclic hemiacetal 1 used in the synthesis of the fluorine-containing monomer 1. As a result, the following fluorine-containing monomer 2 was obtained with a yield of 93%.

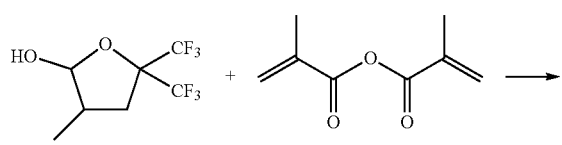

FLUORINE-CONTAINING
CYCLIC HEMIACETAL 2

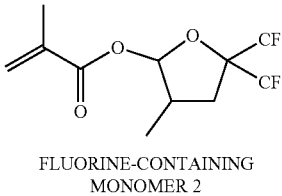

FLUORINE-CONTAINING
MONOMER 2

<NMR Analysis Results>

$^1$H-NMR (solvent: deuterated chloroform, standard substance: TMS) δ (ppm) 1.19 (3H, s) (Isomer A), 1.23 (3H, s) (Isomer B); the following peaks were assigned to the isomer mixture without peak separation of the isomers: 1.92 (3H, s), 2.32-2.59 (2H, m), 2.72-2.89 (2H, m), 5.65 (1H, q), 6.14 (1H, q), 6.17 (1H, dd)

$^{19}$F-NMR (solvent: deuterated chloroform, standard substance: $C_6D_6$) δ (ppm) −77.3 (3F, s), −79.0 (3F, s)

2-3. Synthesis of Fluorine-Containing Monomer 3

The reaction shown below was performed in the same manner as in the synthesis of the fluorine-containing monomer 2, except that 2-fluoroacrylic acid chloride was used in place of the methacrylic anhydride used in the synthesis of the fluorine-containing monomer 2. As a result, the following fluorine-containing monomer 3 was obtained with a yield of 70/%.

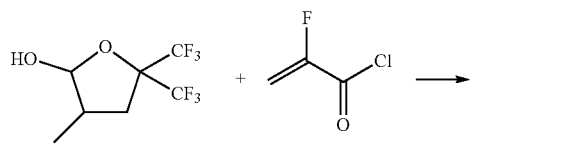

FLUORINE-CONTAINING
CYCLIC HEMIACETAL 2

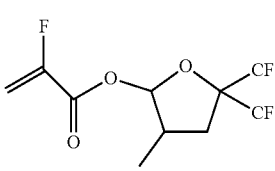

FLUORINE-CONTAINING
MONOMER 3

<NMR Analysis Results>

$^1$H-NMR (solvent: deuterated chloroform, standard substance: TMS) δ (ppm) 1.17 (3H, s) (Isomer A), 1.22 (3H, s) (Isomer B); the following peaks were assigned to the isomer mixture without peak separation of the isomers: 1.92 (3H, s), 2.32-2.59 (2H, m), 2.72-2.89 (2H, m), 6.12 (1H, q), 6.45 (1H, q), 6.68 (1H, d)

$^{19}$F-NMR (solvent: deuterated chloroform, standard substance: $C_6D_6$) δ (ppm) −10.3 (1F, s), −77.3 (3F, s), −79.0 (3F, s)

2-4. Synthesis of Fluorine-Containing Monomer 4

The reaction shown below was performed in the same manner as in the synthesis of the fluorine-containing monomer 2, except that 2-methacryloyloxyacetyl chloride was used in place of the methacrylic anhydride used in the synthesis of the fluorine-containing monomer 2. As a result, the following fluorine-containing monomer 4 was obtained with a yield of 80/a %.

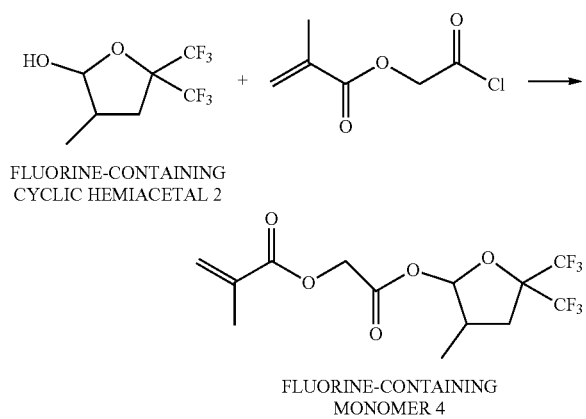

FLUORINE-CONTAINING
CYCLIC HEMIACETAL 2

FLUORINE-CONTAINING
MONOMER 4

<NMR Analysis Results>

$^1$H-NMR (solvent: deuterated chloroform, standard substance: TMS) δ (ppm) 1.21 (3H, s), 1.90 (3H, s), 2.30-2.55 (2H, m), 2.74-2.86 (2H, m), 4.43 (2H, s), 5.60 (1H, q), 6.09 (1H, q), 6.15 (1H, dd)

$^{19}$F-NMR (solvent: deuterated chloroform, standard substance: $C_6D_6$) δ (ppm) −77.7 (3F, s), −79.6 (3F, s)

2-5. Synthesis of Fluorine-Containing Monomer 5

In a 300-ml glass flask with a stirrer, 22.4 g (0.1 mol) of the fluorine-containing cyclic hemiacetal 2, 15.1 g (0.15 mol) of trimethylamine, 0.8 g (0.05 mol) of potassium iodide, 20 ml of dimethylformamide and methoxyphenol (1000 ppm) as a polymerization inhibitor were put. While the inside temperature of the flask was maintained at 30° C. or lower, 16.3 g (0.11 mol) of chloroethyl methacrylate was dropped into the flask. The resulting mixture was stirred for 2 hours. To the mixture, 40 ml of diisopropyl ether and 30 ml of pure water were added. The mixture was stirred and then subjected to separation. The separated organic layer was admixed with 50 ml of an aqueous solution of 5 wt % hydrochloric acid, stirred for 30 minutes and subjected to separation. The separated organic layer was washed twice with 50 ml of pure water and then subjected to vacuum distillation under the conditions of a pressure of 1.0 kPa and a temperature of 89 to 91° C. As a result, the following fluorine-containing monomer 5 was obtained with a yield of 45%. This reaction process is as shown below.

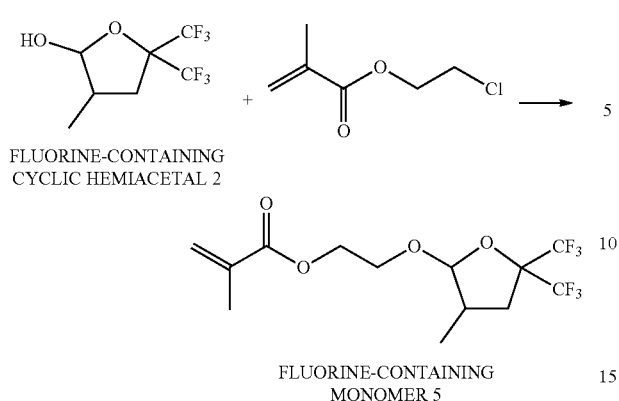

FLUORINE-CONTAINING
CYCLIC HEMIACETAL 2

FLUORINE-CONTAINING
MONOMER 5

<NMR Analysis Results>
$^1$H-NMR (solvent: deuterated chloroform, standard substance: TMS) δ (ppm) 1.23 (31H, s), 1.92 (3H, s), 2.22-2.50 (2H, m), 2.70-2.81 (2H, m), 3.85 (2H, m), 4.03 (2H, m), 5.63 (1H, q), 6.15 (H, q), 6.22 (H, dd)
$^{19}$F-NMR (solvent: deuterated chloroform, standard substance: $C_6D_6$) δ (ppm) −77.0 (3F, s), −79.3 (3F, s)

2-6. Synthesis of Fluorine-Containing Monomer 6

The reaction shown below was performed in the same manner as in the synthesis of the fluorine-containing monomer 2, except that the fluorine-containing cyclic hemiacetal 6 was used in place of the fluorine-containing cyclic hemiacetal 2 used in the synthesis of the fluorine-containing monomer 2. As a result, the following fluorine-containing monomer 6 was obtained with a yield of 78%.

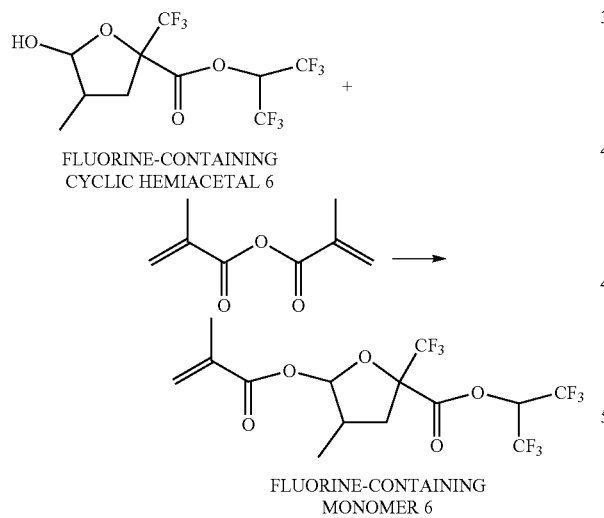

FLUORINE-CONTAINING
CYCLIC HEMIACETAL 6

FLUORINE-CONTAINING
MONOMER 6

<NMR Analysis Results>
$^1$H-NMR (solvent: deuterated chloroform, standard substance: TMS) δ (ppm) 1.16 (3H, s), 1.95 (3H, s), 2.27-2.54 (2H, m), 2.65-2.80 (2H, m), 5.61 (1H, q), 5.83 (1H, m), 6.12 (1H, q), 6.18 (1H, dd)
$^{19}$F-NMR (solvent: deuterated chloroform, standard substance: $C_6D_6$) δ (ppm) −77.5 (6F, m), −79.5 (3F, m)

2-7. Synthesis of Fluorine-Containing Monomer 7

The reaction shown below was performed in the same manner as in the synthesis of the fluorine-containing monomer 2, except that the fluorine-containing cyclic hemiacetal 7 was used in place of the fluorine-containing cyclic hemiacetal 2 used in the synthesis of the fluorine-containing monomer 2. As a result, the following fluorine-containing monomer 7 was obtained with a yield of 74%.

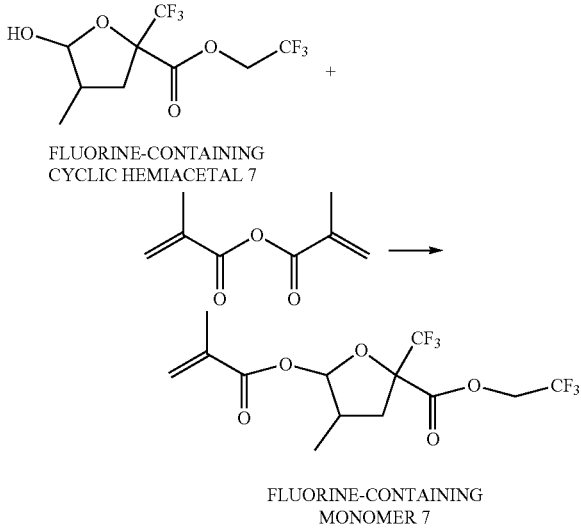

FLUORINE-CONTAINING
CYCLIC HEMIACETAL 7

FLUORINE-CONTAINING
MONOMER 7

<NMR Analysis Results>
$^1$H-NMR (solvent: deuterated chloroform, standard substance: TMS) δ (ppm) 1.22 (3H, s), 1.89 (3H, s), 2.24-2.50 (2H, m), 2.68-2.87 (2H, m), 4.86 (2H, m), 5.65 (1H, q), 6.13 (1H, q), 6.18 (1H, dd)
$^{19}$F-NMR (solvent: deuterated chloroform, standard substance: $C_6D_6$) δ (ppm) −77.9 (3F, m), −78.5 (3F, m)

2-8. Synthesis of Fluorine-Containing Monomer 8

The reaction shown below was performed in the same manner as in the synthesis of the fluorine-containing monomer 6, except that 2-fluoroacrylic acid chloride was used in place of the methacrylic anhydride used in the synthesis of the fluorine-containing monomer 6. As a result, the following fluorine-containing monomer 8 was obtained with a yield of 68%.

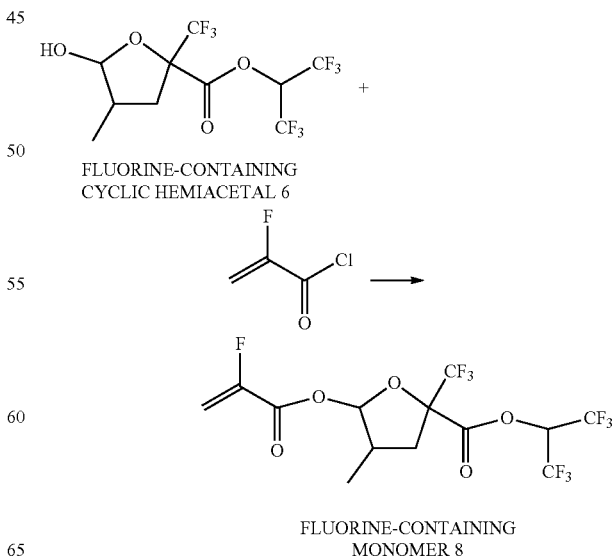

FLUORINE-CONTAINING
CYCLIC HEMIACETAL 6

FLUORINE-CONTAINING
MONOMER 8

<NMR Analysis Results>

¹H-NMR (solvent: deuterated chloroform, standard substance: TMS) δ (ppm) 1.17 (3H, s), 2.27-2.52 (2H, m), 2.62-2.82 (2H, m), 5.64 (1H, q), 5.93 (1H, m), 6.42 (1H, q), 6.68 (1H, dd)

¹⁹F-NMR (solvent: deuterated chloroform, standard substance: $C_6D_6$) δ (ppm) -10.1 (1F, s), -77.9 (6F, m), -79.0 (3F, m)

2-9. Synthesis of Fluorine-Containing Monomer 9

The reaction shown below was performed in the same manner as in the synthesis of the fluorine-containing monomer 7, except that 2-fluoroacrylic acid chloride was used in place of the methacrylic anhydride used in the synthesis of the fluorine-containing monomer 7. As a result, the following fluorine-containing monomer 9 was obtained with a yield of 65%.

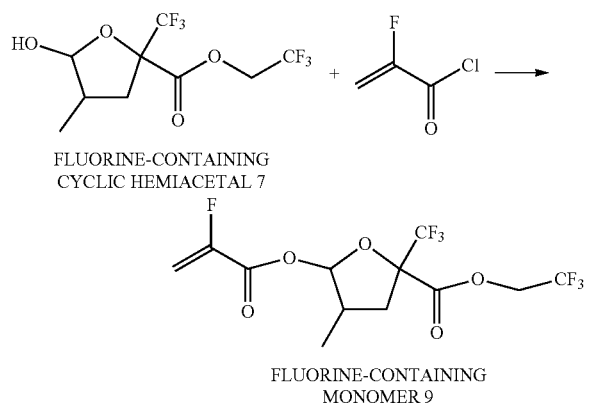

<NMR Analysis Results>

¹H-NMR (solvent: deuterated chloroform, standard substance: TMS) δ (ppm) 1.17 (3H, s), 2.27-2.52 (2H, m), 2.62-2.82 (2H, m), 4.93 (2H, m), 5.64 (1H, q), 6.42 (1H, q), 6.68 (1H, dd)

¹⁹F-NMR (solvent: deuterated chloroform, standard substance: $C_6D_6$) δ (ppm) -10.4 (1F, s), -77.1 (6F, m), -79.3 (3F, m)

3. Synthesis of Comparative Monomers

For comparison with the fluorine-containing monomers 1 to 7 according to the present invention, synthesized were comparative monomers 1 to 3 each of which does not belong to the fluorine-containing monomer of the formula (6).

3-1. Synthesis of Comparative Monomer 1

The comparative monomer 1 was synthesized by a method disclosed in Patent Document 3. In a 1000-ml glass flask with a stirrer, 30.0 g of methacrylic acid and 58.6 g of hydroxypyrane were dissolved in 450 ml of ethylene dichloride. To the solution, 0.1 g of paratoluenesulfonic acid was further added. The solution was stirred for 1 hour. Then, the reaction was stopped with the addition of 3 ml of triethylemine to the solution. The thus-obtained reaction mixture was washed with 50 ml of water and then dried with anhydrous magnesium sulfate. After the solvent was evaporated from the reaction mixture, the reaction mixture was subjected to vacuum distillation under the conditions of a pressure of 0.4 kPa and a temperature of 66 to 67° C. As a result, the comparative monomer 1 was obtained in an amount of 1.50 g. This reaction process is as shown below.

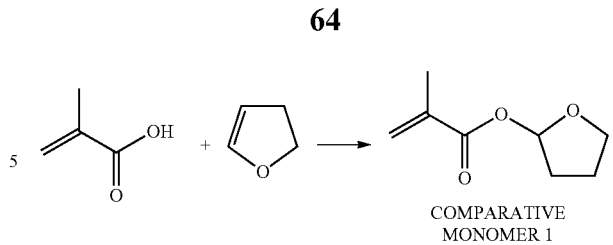

3-2. Synthesis of Comparative Monomer 2

The comparative monomer 2 was synthesized by a method disclosed in Patent Document 5. Into a mixture of 16.8 g of HFIP and 129 g of tetrahydrofuran, 129 ml of butyl lithium (in the form of a 1.6 M hexane solution) was added at 5° C. in an atmosphere of nitrogen. The mixture was stirred for 1 hour at 5° C. Then, 14.2 g of 2-oxopropyl methacrylate was added to the mixture at 5° C. After the mixture was stirred for 10 hours, the reaction was stopped with the addition of dilute hydrochloric acid to the mixture. The thus-obtained reaction mixture was neutralized, subjected to ordinary aqueous post-treatment, and then, subjected to purification by silica gel column chromatography. There was thus obtained 25.3 g of a triol compound as a synthesis intermediate. A mixture of 24 g of the triol compound, 15.6 g of trimethylamine and 15 g of toluene was stirred for 4 hours at 70° C. After the mixture was cooled to room temperature, the mixture was neutralized with dilute hydrochloric acid. The thus-formed organic layer was collected and subjected to ordinary post-treatment operations, i.e., washing, drying and concentration, thereby yielding a crude product. By vacuum distillation of the crude product, 20 g of acetal was obtained. A mixture of 3.2 g of the above-obtained acetal, 2.8 g of methyl iodide, 2.8 g of silver (I) oxide and 150 g of ethyl acetate was stirred for 24 hours at 40° C. An insoluble substance was filtered out of the mixture. The mixture was concentrated under reduced pressure and subjected to purification by silica gel column chromatography. As a result, the comparative monomer 2 was obtained in an amount of 3 g. This reaction process is as shown below.

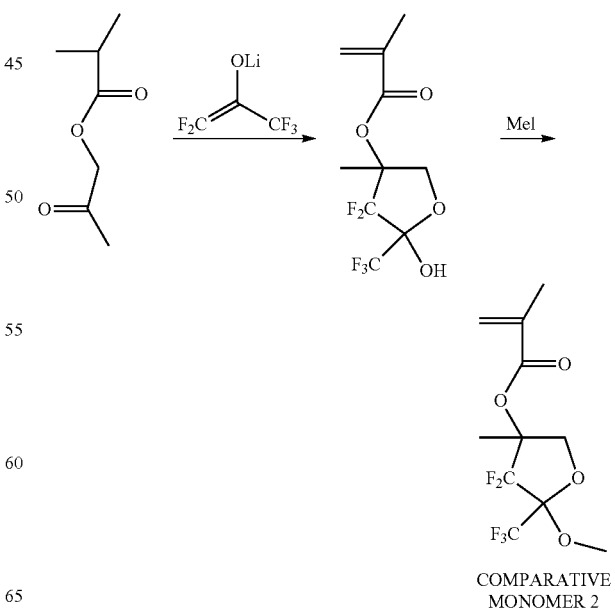

In the above scheme, MeI represents methyl iodide.

3-3. Synthesis of Comparative Monomer 3

In a 300-ml glass flask with a stirrer, 33.6 g (0.3 mol) of vinyl methacrylate (available from Tokyo Chemical Industry Co., Ltd.; the same applies to the following), 52.9 g (0.315 mol) of HFIP were put. After that, 0.74 g (7.5 mmol) of sulfuric acid was gradually put into the flask. The reaction shown below was performed by stirring the mixture for 6 hours at a reaction temperature of 40° C.

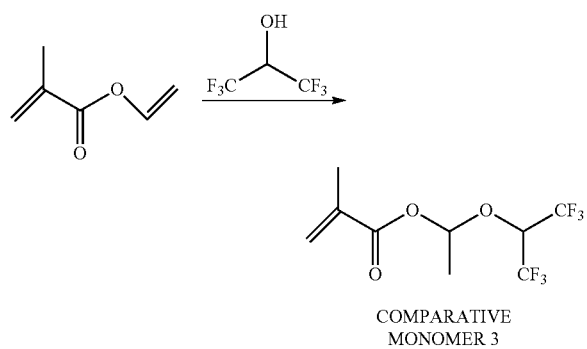

COMPARATIVE
MONOMER 3

After the thus-obtained reaction liquid was cooled to room temperature, the reaction liquid was admixed with 50 ml of 6 mass % sodium bicarbonate water and stirred. Subsequently, the reaction liquid was put into a separatory funnel, left still and thereby separated into two layers. The organic layer was collected and subjected to vacuum distillation. As a result, the comparative monomer 3 was obtained in an amount of 39 g. The yield of the monomer was 47%. The comparative monomer 3 had a boiling point of 62° C. at a pressure of 4.0 kPa.

4. Synthesis of Polymers

Fluorine-containing polymers 1 to 12 and comparative polymers 1 to 7 were synthesized using the fluorine-containing monomers 1 to 9, the comparative monomers 1 to 3, and hexafluoroisopropyl methacrylate (available under the trade name of HFIP-M from Central Glass Company, Ltd.) as a comparative monomer 4. The fluorine-containing polymers 1 to 12 each belong to the fluorine-containing polymer (1). On the other hand, the comparative polymers 1 to 7 are for comparison with the fluorine-containing polymers 1 to 12 and each does not belong to the fluorine-containing polymer (1).

The fluorine-containing polymers 1 to 9 and the comparative monomers 1 to 4 were provided in homopolymer form such that the effects and performance of the respective monomers were clearly shown for comparison. The fluorine-containing polymers 10 to 12 and the comparative polymers 5 to 7 were provided in copolymer form using 5-methacryloyloxy-2,6-norbornanecarbolactone (MNLA) as a copolymerization monomer for performance comparison of the fluorine-containing polymer according to the present invention and the comparative monomer as resist materials.

[Analysis of Polymers]
<NMR>

The repeating unit composition of the polymer was determined based on values of $^1$H-NMR and $^{19}$F-NMR measurements by NMR spectroscopy.

<Molecular Weight>

The number-average molecular weight Mn and the molecular weight dispersity (i.e. ratio Mw/Mn between the number-average molecular weight Mn and the mass-average molecular weight Mw) of the polymer were determined by high-speed gel-permeation chromatography (also referred to as "GPC"; available as HLC-8320GPC from Tosoh Corporation) using an ALPHA-M column and an ALPHA-2500 column, both of which are available from Tosoh Corporation, connected in series and using tetrahydrofuran as an elution solvent.

4-1. Synthesis of Fluorine-Containing Polymer 1

In a 300-ml glass flask with a stirrer, 29.2 g (0.1 mol) of the fluorine-containing monomer 1 and 60 g of 2-butanone as a solvent were mixed at room temperature so that a butanone solution containing 33 mass % of the monomer was provided. To the solution, 0.8 g (0.005 mol) of 2,2'-azobis(isobutyronitrile) (also referred to as "AIBN"; available from Wako Pure Chemical Corporation) as a polymerization initiator was added. The solution was subjected to degassing while stirring. Then, the inside of the flask was replaced by nitrogen gas. After the inside temperature of the flask was raised to 80° C., the solution was reacted for 6 hours. After the completion of the reaction, the contents of the flask were dropped into 500 g of n-heptane to form a white precipitate. The precipitate was filtered out and subjected to vacuum drying at a temperature of 60° C. There was thus obtained 25.6 g of the fluorine-containing polymer 1, whose repeating unit was derived from the fluorine-containing monomer 1, as a white solid. The yield of the fluorine-containing polymer 1 was 88%.

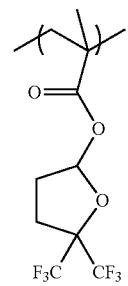

FLUORINE-CONTAINING
POLYMER 1

<GPC Measurement Results>
Mw=22,000; Mw/Mn=2.0

4-2. Synthesis of Fluorine-Containing Polymer 2

The fluorine-containing polymer 2 containing the following repeating unit was synthesized in the same manner as in the synthesis of the fluorine-containing polymer 1, except that the fluorine-containing monomer 2 was used in place of the fluorine-containing monomer 1 used in the synthesis of the fluorine-containing polymer 1. The yield of the fluorine-containing polymer 2 was 87%.

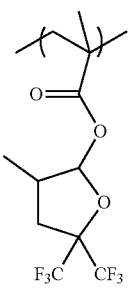

FLUORINE-CONTAINING
POLYMER 2

<GPC Measurement Results>

Mw=23,100; Mw/Mn=2.1

4-3. Synthesis of Fluorine-Containing Polymer 3

The fluorine-containing polymer 3 containing the following repeating unit was synthesized in the same manner as in the synthesis of the fluorine-containing polymer 1, except that the fluorine-containing monomer 3 was used in place of the fluorine-containing monomer 1 used in the synthesis of the fluorine-containing polymer 1. The yield of the fluorine-containing polymer 3 was 93%.

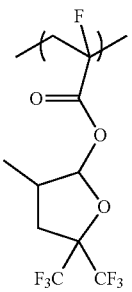

FLUORINE-CONTAINING
POLYMER 3

<GPC Measurement Results>

Mw=21,200; Mw/Mn=2.3

4-4. Synthesis of Fluorine-Containing Polymer 4

The fluorine-containing polymer 4 containing the following repeating unit was synthesized in the same manner as in the synthesis of the fluorine-containing polymer 1, except that the fluorine-containing monomer 4 was used in place of the fluorine-containing monomer 1 used in the synthesis of the fluorine-containing polymer 1. The yield of the fluorine-containing polymer 4 was 92%.

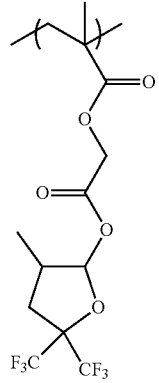

FLUORINE-CONTAINING
POLYMER 4

<GPC Measurement Results>

Mw=22,500; Mw/Mn=2.1

4-5. Synthesis of Fluorine-Containing Polymer 5

The fluorine-containing polymer 5 containing the following repeating unit was synthesized in the same manner as in the synthesis of the fluorine-containing polymer 1, except that the fluorine-containing monomer 5 was used in place of the fluorine-containing monomer 1 used in the synthesis of the fluorine-containing polymer 1. The yield of the fluorine-containing polymer 5 was 90%.

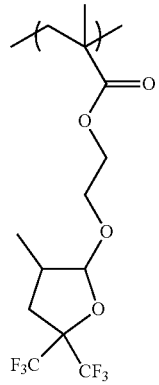

FLUORINE-CONTAINING
POLYMER 5

<GPC Measurement Results>

Mw=24,200; Mw/Mn=2.3

4-6. Synthesis of Fluorine-Containing Polymer 6

The fluorine-containing polymer 6 containing the following repeating unit was synthesized in the same manner as in the synthesis of the fluorine-containing polymer 1, except that the fluorine-containing monomer 6 was used in place of the fluorine-containing monomer 1 used in the synthesis of the fluorine-containing polymer 1. The yield of the fluorine-containing polymer 6 was 72%.

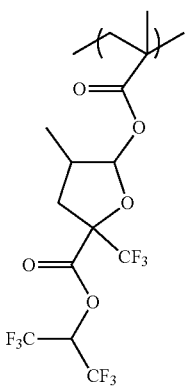

FLUORINE-CONTAINING
POLYMER 6

<GPC Measurement Results>

Mw=20,700; Mw/Mn=2.5

4-7. Synthesis of Fluorine-Containing Polymer 7

The fluorine-containing polymer 7 containing the following repeating unit was synthesized in the same manner as in the synthesis of the fluorine-containing polymer 1, except that the fluorine-containing monomer 7 was used in place of the fluorine-containing monomer 1 used in the synthesis of the fluorine-containing polymer 1. The yield of the fluorine-containing polymer 7 was 78%.

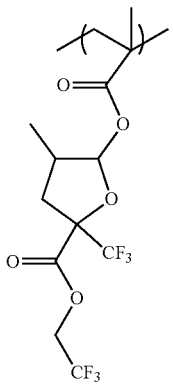

FLUORINE-CONTAINING
POLYMER 7

<GPC Measurement Results>

Mw=20,100; Mw/Mn=2.2

4-8. Synthesis of Fluorine-Containing Polymer 8

The fluorine-containing polymer 8 containing the following repeating unit was synthesized in the same manner as in the synthesis of the fluorine-containing polymer 1, except that the fluorine-containing monomer 8 was used in place of the fluorine-containing monomer 1 used in the synthesis of the fluorine-containing polymer 1. The yield of the fluorine-containing polymer 8 was 90/a %.

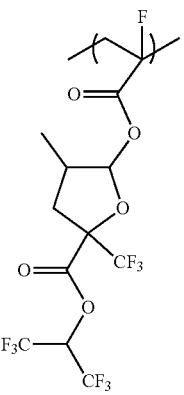

FLUORINE-CONTAINING
POLYMER 8

<GPC Measurement Results>

Mw=19,700; Mw/Mn=2.3

4-9. Synthesis of Fluorine-Containing Polymer 9

The fluorine-containing polymer 9 containing the following repeating unit was synthesized in the same manner as in the synthesis of the fluorine-containing polymer 1, except that the fluorine-containing monomer 9 was used in place of the fluorine-containing monomer 1 used in the synthesis of the fluorine-containing polymer 1. The yield of the fluorine-containing polymer 9 was 89/a %.

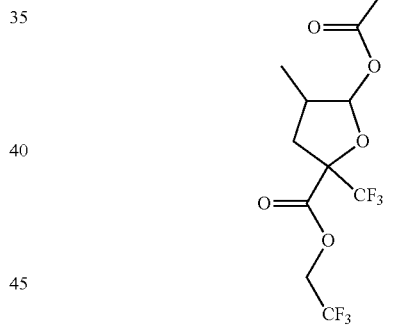

FLUORINE-CONTAINING
POLYMER 9

<GPC Measurement Results>

Mw=20,900; Mw/Mn=2.1

4-10. Synthesis of Fluorine-Containing Polymer 10

In a glass flask, 29.2 g (0.1 mol) of the fluorine-containing monomer 1, 11.1 g (0.05 mol) of 5-methacryloyloxy-2,6-norbornanecarbolactone (MNLA) for formation of an adhesive repeating unit as a resist material and 0.67 g of n-dodecyl mercaptan (available from Tokyo Chemical Industry Co., Ltd.) were put at room temperature (about 20° C.). Subsequently, 82.9 g of 2-butanone was added to dissolve the contents of the flask. To the resulting solution, 1.7 g of 2,2'-azobis(isobutyronitrile) (also referred to as "AIBN"; available from Wako Pure Chemical Corporation) as a polymerization initiator was added. The solution was subjected to degassing while stirring. Then, the inside of the flask was replaced by nitrogen gas. After the inside temperature of the flask was raised to 75° C., the solution was reacted for 16 hours. After the completion of the reaction, the contents of the flask were dropped into 620.0 g of n-heptane to form a white precipitate. The precipitate was filtered out and subjected to vacuum drying at a temperature of 60° C. There was thus obtained 34 g of the fluorine-containing polymer 10, whose repeating units were respectively derived from the fluorine-containing monomer 1 and the MNLA, as a white solid. The yield of the fluorine-containing polymer was 85%.

FLUORINE-CONTAINING POLYMER 10

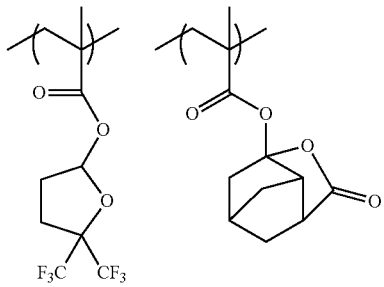

<NMR Measurement Results>

The content ratio of the repeating units in the fluorine-containing polymer 10 was determined by NMR. The content ratio of the repeating unit derived from the fluorine-containing monomer 1 to the repeating unit derived from MNLA was 67:33 in terms of mol %.

<GPC Measurement Results>

Mw=8,500; Mw/Mn=1.7

4-11. Synthesis of Fluorine-Containing Polymer 11

The fluorine-containing polymer 11 containing the following repeating units was synthesized in the same manner as in the synthesis of the fluorine-containing polymer 10, except that the fluorine-containing monomer 2 was used in place of the fluorine-containing monomer 1 used in the synthesis of the fluorine-containing polymer 10.

FLUORINE-CONTAINING POLYMER 11

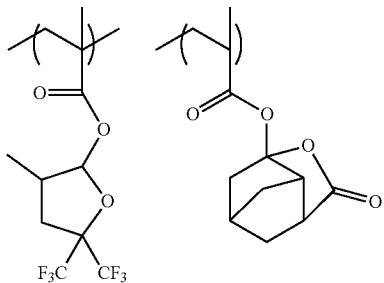

<NMR Measurement Results>

The content ratio of the repeating units in the fluorine-containing polymer 11 was determined by NMR. The content ratio of the repeating unit derived from the fluorine-containing monomer 2 to the repeating unit derived from MNLA was 65:35 in terms of mol %.

<GPC Measurement Results>

Mw=8,700; Mw/Mn=1.6

4-12. Synthesis of Fluorine-Containing Polymer 12

The fluorine-containing polymer 12 containing the following repeating units was synthesized in the same manner as in the synthesis of the fluorine-containing polymer 10, except that the fluorine-containing monomer 6 was used in place of the fluorine-containing monomer 1 used in the synthesis of the fluorine-containing polymer 10.

FLUORINE-CONTAINING POLYMER 12

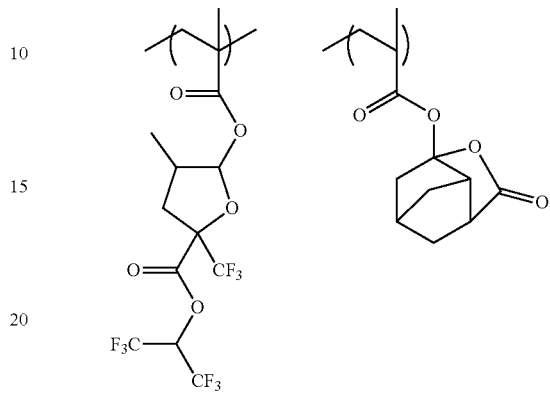

<NMR Measurement Results>

The content ratio of the repeating units in the fluorine-containing polymer 11 was determined by NMR. The content ratio of the repeating unit derived from the fluorine-containing monomer 6 to the repeating unit derived from MNLA was 64:36 in terms of mol %.

<GPC Measurement Results>

Mw=7,700; Mw/Mn=1.7

5. Synthesis of Comparative Polymers

For comparison with the fluorine-containing polymers 1 to 10 according to the present invention, synthesized were the comparative polymers 1 to 7 each of which does not belong to the fluorine-containing polymer (1).

5-1. Synthesis of Comparative Polymer 1

The comparative polymer 1 containing the following repeating unit was synthesized in the same manner as in the synthesis of the fluorine-containing polymer 1, except that the comparative monomer 1 was used in place of the fluorine-containing monomer 1 used in the synthesis of the fluorine-containing polymer 1.

COMPARATIVE POLYMER 1

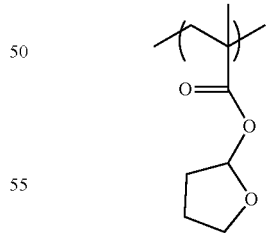

<GPC Measurement Results>

Mw=20,100; Mw/Mn=2.2

5-2. Synthesis of Comparative Polymer 2

The comparative polymer 2 containing the following repeating unit was synthesized in the same manner as in the synthesis of the fluorine-containing polymer 1, except that the comparative monomer 2 was used in place of the fluorine-containing monomer 1 used in the synthesis of the fluorine-containing polymer 1.

COMPARATIVE POLYMER 2

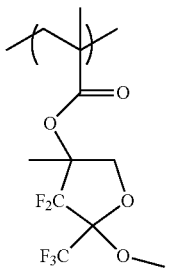

<GPC Measurement Results>
Mw=23,400; Mw/Mn=2.1

5-3. Synthesis of Comparative Polymer 3

The comparative polymer 3 containing the following repeating unit was synthesized in the same manner as in the synthesis of the fluorine-containing polymer 1, except that the comparative monomer 3 was used in place of the fluorine-containing monomer 1 used in the synthesis of the fluorine-containing polymer 1.

COMPARATIVE POLYMER 3

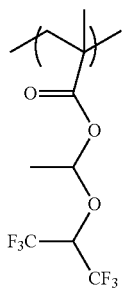

<GPC Measurement Results>
Mw=22,800; Mw/Mn=2.1

5-4. Synthesis of Comparative Polymer 4

The comparative polymer 4 containing the following repeating unit was synthesized in the same manner as in the synthesis of the fluorine-containing polymer 1, except that the comparative monomer 4 was used in place of the fluorine-containing monomer 1 used in the synthesis of the fluorine-containing polymer 1.

COMPARATIVE POLYMER 4

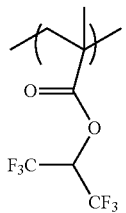

<GPC Measurement Results>
Mw=20,100; Mw/Mn=2.1

5-5. Synthesis of Comparative Polymer 5

The comparative polymer 5 containing the following repeating units was synthesized in the same manner as in the synthesis of the fluorine-containing polymer 10, except that the comparative monomer 1 was used in place of the fluorine-containing monomer 1 used in the synthesis of the fluorine-containing polymer 10. The yield of the comparative polymer 5 was 89/a %.

COMPARATIVE POLYMER 5

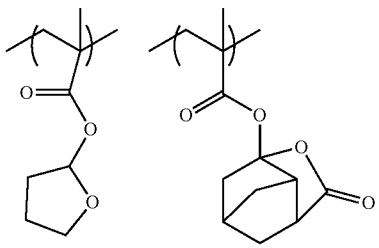

<NMR Measurement Results>

The content ratio of the repeating units in the comparative polymer 5 was determined by NMR. The content ratio of the repeating unit derived from the comparative monomer 1 to the repeating unit derived from MNLA was 67:33 in terms of mol %.

<GPC Measurement Results>
Mw=8,300; Mw/Mn=1.7

5-6. Synthesis of Comparative Polymer 6

The comparative polymer 6 containing the following repeating units was synthesized in the same manner as in the synthesis of the fluorine-containing polymer 10, except that the comparative monomer 2 was used in place of the fluorine-containing monomer 1 used in the synthesis of the fluorine-containing polymer 10. The yield of the comparative polymer 6 was 83%.

COMPARATIVE POLYMER 6

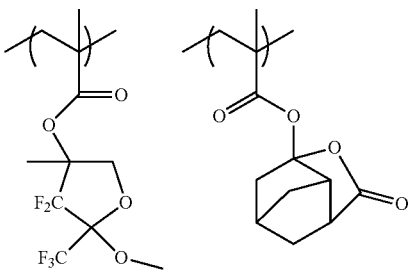

<NMR Measurement Results>

The content ratio of the repeating units in the comparative polymer 6 was determined by NMR. The content ratio of the repeating unit derived from the comparative monomer 2 to the repeating unit derived from MNLA was 65:35 in terms of mol %.

<GPC Measurement Results>
Mw=8,900; Mw/Mn=1.6

5-7. Synthesis of Comparative Polymer 7

The comparative polymer 7 containing the following repeating units was synthesized in the same manner as in the synthesis of the fluorine-containing polymer 10, except that the comparative monomer 3 was used in place of the fluorine-containing monomer 1 used in the synthesis of the fluorine-containing polymer 10. The yield of the comparative polymer 7 was 81%.

COMPARATIVE POLYMER 7

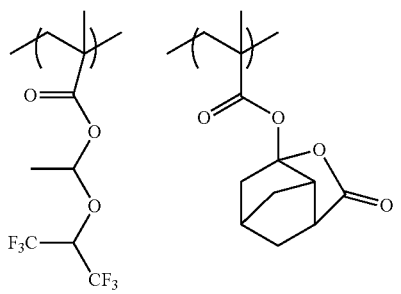

<NMR Measurement Results>

The content ratio of the repeating units in the comparative polymer 7 was determined by NMR. The content ratio of the repeating unit derived from the comparative monomer 3 to the repeating unit derived from MNLA was 66:34 in terms of mol %.

<GPC Measurement Results>

Mw=8,100; Mw/Mn=1.6

5-8. Repeating Units of Fluorine-Containing Polymers 1 to 10 and Comparative Polymers 1 to 7

The repeating units of the fluorine-containing polymers 1 to 10 and the comparative polymers 1 to 7 are shown below.

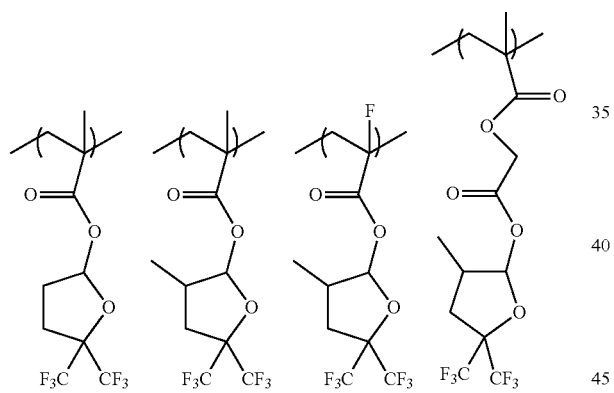

FLUORINE-CONTAINING POLYMER 1   FLUORINE-CONTAINING POLYMER 2   FLUORINE-CONTAINING POLYMER 3   FLUORINE-CONTAINING POLYMER 4

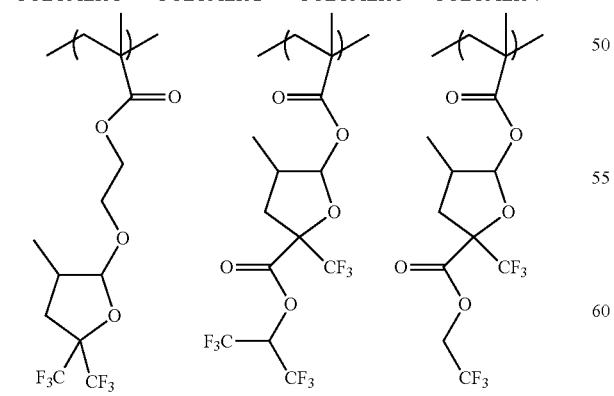

FLUORINE-CONTAINING POLYMER 5   FLUORINE-CONTAINING POLYMER 6   FLUORINE-CONTAINING POLYMER 7

-continued

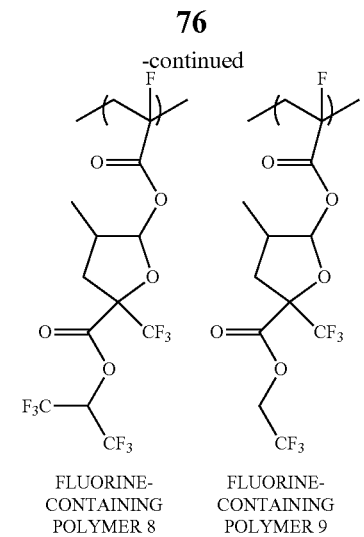

FLUORINE-CONTAINING POLYMER 8   FLUORINE-CONTAINING POLYMER 9

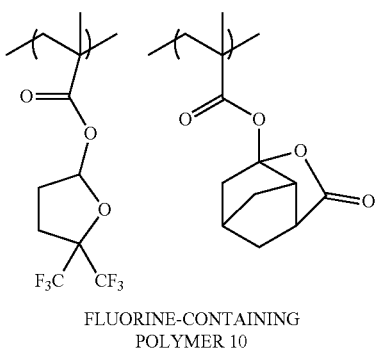

FLUORINE-CONTAINING POLYMER 10

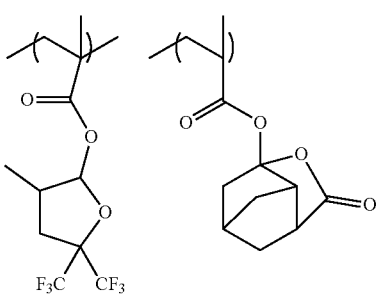

FLUORINE-CONTAINING POLYMER 11

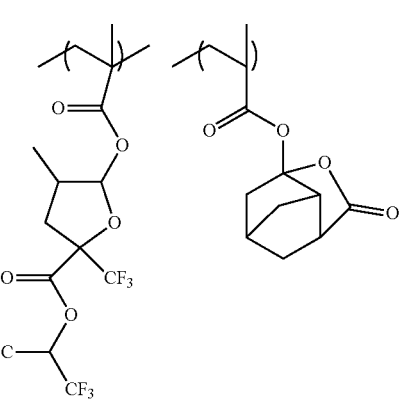

FLUORINE-CONTAINING POLYMER 12

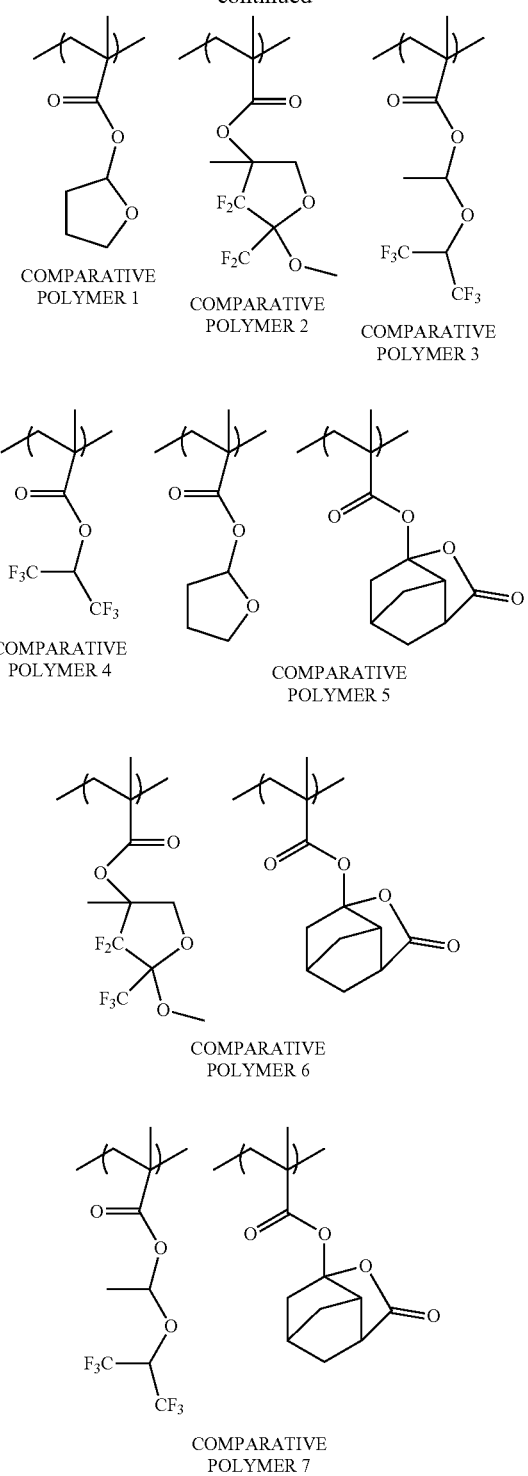

COMPARATIVE POLYMER 1
COMPARATIVE POLYMER 2
COMPARATIVE POLYMER 3
COMPARATIVE POLYMER 4
COMPARATIVE POLYMER 5
COMPARATIVE POLYMER 6
COMPARATIVE POLYMER 7

5-9. Composition, Molecular Weight and Yield of Fluorine-Containing Polymers 1 to 10 and Comparative Polymers 1 to 7

The composition (i.e. the content ratio of the repeating unit), the weight-average molecular weight, the molecular weight dispersity and the yield of the fluorine-containing polymers 1 to 10 and the comparative polymers 1 to 7 are summarized in TABLE 1.

TABLE 1

| Polymer | Composition (content ratio of repeating units) (mol %) Monomer | MNLA | Weight-average molecular weight (Mw) | Molecular weight dispersity (Mw/Mn) | Yield (%) |
|---|---|---|---|---|---|
| Fluorine-containing polymer 1 | 100 | — | 22000 | 2.0 | 88 |
| Fluorine-containing polymer 2 | 100 | — | 23100 | 2.1 | 87 |
| Fluorine-containing polymer 3 | 100 | — | 21200 | 2.3 | 93 |
| Fluorine-containing polymer 4 | 100 | — | 22500 | 2.1 | 92 |
| Fluorine-containing polymer 5 | 100 | — | 24200 | 2.3 | 90 |
| Fluorine-containing polymer 6 | 100 | — | 20700 | 2.5 | 72 |
| Fluorine-containing polymer 7 | 100 | — | 20100 | 2.2 | 78 |
| Fluorine-containing polymer 8 | 100 | — | 19700 | 2.3 | 90 |
| Fluorine-containing polymer 9 | 100 | — | 20900 | 2.1 | 89 |
| Fluorine-containing polymer 10 | 67 | 33 | 8500 | 1.7 | 85 |
| Fluorine-containing polymer 11 | 65 | 35 | 8700 | 1.6 | 86 |
| Fluorine-containing polymer 12 | 64 | 36 | 7700 | 1.7 | 73 |
| Comparative polymer 1 | 100 | — | 20100 | 2.2 | 85 |
| Comparative polymer 2 | 100 | — | 23400 | 2.1 | 87 |
| Comparative polymer 3 | 100 | — | 22800 | 2.5 | 89 |
| Comparative polymer 4 | 100 | — | 20100 | 2.1 | 78 |
| Comparative polymer 5 | 67 | 33 | 8300 | 1.7 | 89 |
| Comparative polymer 6 | 65 | 35 | 8900 | 1.6 | 83 |
| Comparative polymer 7 | 66 | 34 | 8100 | 1.6 | 81 |

Note:
"Monomer" refers to the content of the fluorine-containing monomer or comparative monomer in the polymer; and "MNLA" refers to the content of MNLA (5-methacryloyloxy-2,6-norbornanecarbolactone) in the polymer.

5-10. Glass Transition Point and 5% Weight Reduction Rate of Fluorine-Containing Polymers 1 to 9 and Comparative Polymers 1 to 4

Measurements of the glass transition point and 5% weight reduction rate of the fluorine-containing polymers 1 to 9 and the comparative polymers 1 to 4 were made by the following methods.

[Measurement Methods of Glass Transition Point and 5% Weight Reduction Rate]

The thermal properties, such as glass transition point (referred to as "Tg") and 5% weight reduction (referred to as "Td5") in thermogravimetric analysis, of the fluorine-containing polymers 1 to 9 and the comparative polymers 1 to 4 were measured with a differential scanning calorimeter (hereinafter also referred to as "DSC") and a simultaneous thermogravimetric analyzer (hereinafter also referred to as "DTA") both available from Hitachi High-Technologies Corporation.

[Measurement Results]

The measurement results of the Tg and Td5 values of the fluorine-containing polymers 1 to 9 and the comparative polymers 1 to 4 are shown in TABLE 2. It is known that a pattern forming material for lithography and printed electronics tends to provide a pattern with good line edge roughness and line width roughness as the higher the values of Tg and Td5, the more faithfully the mask pattern can be transferred.

TABLE 2

| Example | Polymer | Thermal properties | |
| --- | --- | --- | --- |
| | | Tg (° C.) | Td5 (° C.) |
| Example 1 | Fluorine-containing polymer 1 | 99 | 251 |
| Example 2 | Fluorine-containing polymer 2 | 97 | 245 |
| Example 3 | Fluorine-containing polymer 3 | 102 | 248 |
| Example 4 | Fluorine-containing polymer 4 | 92 | 233 |
| Example 5 | Fluorine-containing polymer 5 | 89 | 234 |
| Example 6 | Fluorine-containing polymer 6 | 95 | 238 |
| Example 7 | Fluorine-containing polymer 7 | 94 | 237 |
| Example 8 | Fluorine-containing polymer 8 | 98 | 249 |
| Example 9 | Fluorine-containing polymer 9 | 97 | 247 |
| Comparative Example 1 | Comparative polymer 1 | 95 | 250 |
| Comparative Example 2 | Comparative polymer 2 | 90 | 235 |
| Comparative Example 3 | Comparative polymer 3 | 73 | 226 |
| Comparative Example 4 | Comparative polymer 4 | 71 | 220 |

The fluorine-containing polymers 1 to 9 and the comparative polymers 1 and 2, each of which had a cyclic acetal structure, showed a Tg value about 25° C. higher than those of the linear comparative polymers 3 and 4. The fluorine-containing polymers 1 to 3, 8 and 9 showed a Tg value higher than that of the comparative polymer 1 whose skeleton was similar to those of the fluorine-containing polymers 1 to 3, 8 and 9 but did not contain a fluorine atom.

6. Pattern Forming Compositions for Printed Electronics 6-1. Preparation of Pattern Forming Composition for Printed Electronics Pattern forming compositions 1 to 9 according to the present invention and comparative compositions 1 to 4 as comparison samples were repapered. The repeating units of the respective polymers were as shown below.

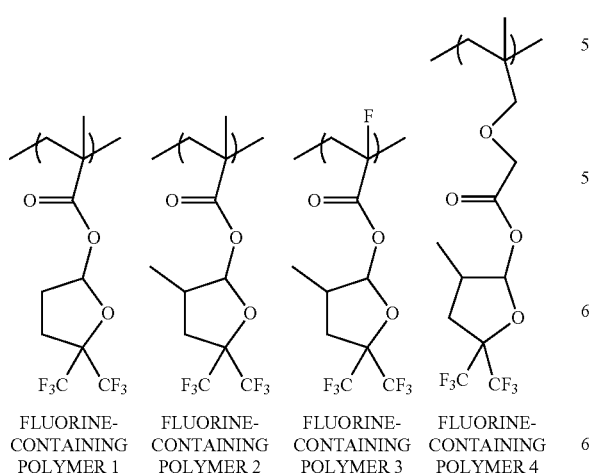

FLUORINE-CONTAINING POLYMER 1  FLUORINE-CONTAINING POLYMER 2  FLUORINE-CONTAINING POLYMER 3  FLUORINE-CONTAINING POLYMER 4

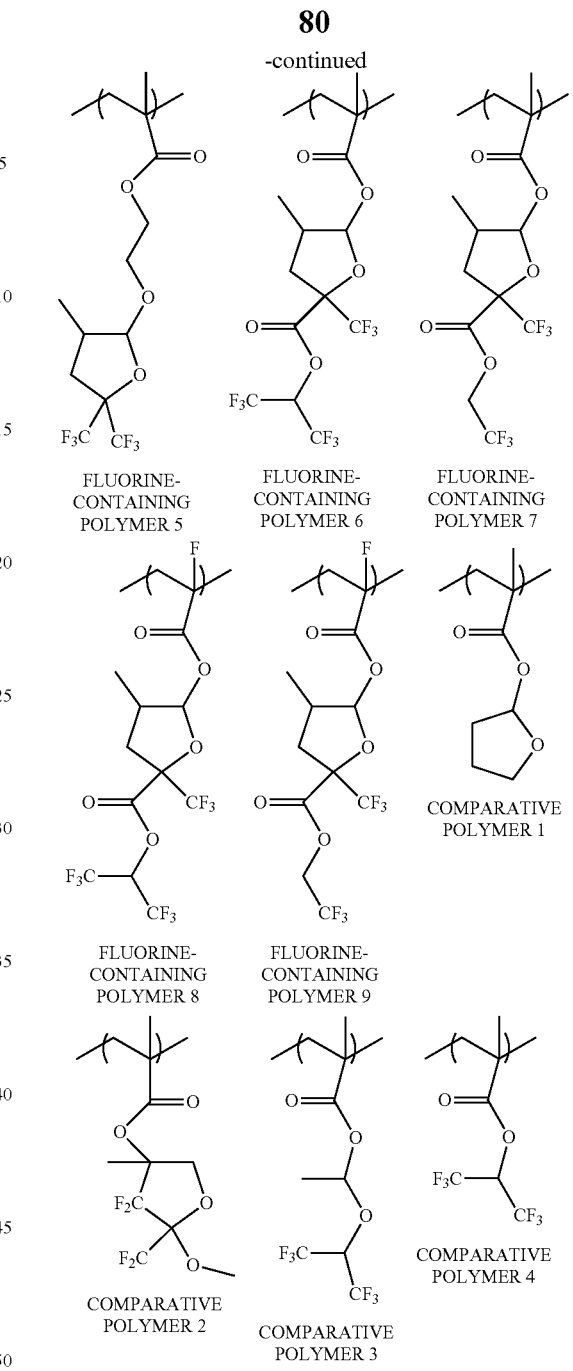

FLUORINE-CONTAINING POLYMER 5  FLUORINE-CONTAINING POLYMER 6  FLUORINE-CONTAINING POLYMER 7

FLUORINE-CONTAINING POLYMER 8  FLUORINE-CONTAINING POLYMER 9  COMPARATIVE POLYMER 1

COMPARATIVE POLYMER 2  COMPARATIVE POLYMER 3  COMPARATIVE POLYMER 4

More specifically, the pattern forming compositions 1 to 9 and the comparative compositions 1 to 4 were respectively prepared by adding, to the fluorine-containing polymers 1 to 9 and the comparative polymers 1 to 4, N-hydroxynaphthalimide-trifluoromethanesulfonate as an acid generator (A), 2-isopropylthioxanthone as a sensitizer (D), 2-phenylbenzyl alcohol as a quencher (C) and diethylene glycol methyl ether as an organic solvent (B) such that content ratio of polymer: acid generator (A):sensitizer (D):quencher (C):organic solvent (B) was 100:2:1:0.5:300 in terms of parts by mass.

6-2. Formation of Film from Pattern Forming Composition for Printed Electronics

Each of the above-prepared pattern forming compositions 1 to 9 and comparative compositions 1 to 4 was applied by a spinner onto a glass substrate. The applied composition was dried for 2 minutes on a hot plate heated at 100° C., thereby forming a film with a thickness of 0.5 μm. Subsequently, the film was exposed to light from a high-pressure mercury-vapor lamp. The film was then exposed to ultraviolet light from the high-pressure mercury-vapor lamp through a photomask so that a pattern of the photomask was transferred to the film. After that, the film was dried by heating at 100° C. for 5 minutes on the hot plate whereby there was obtained a pattern with water repellent and hydrophilic portions (referred to as "water-repellent/hydrophilic pattern").

6-3. Measurement of Contact Angle of Film of Pattern Forming Composition Before and after Exposure and Formation of Pattern of Water-Based Ink

[Measurement of Contact Angle]

A droplet of water was put onto the above-formed film on the substrate. Using a contact angle meter (available from Kyowa Interface Science Co., Ltd.), the static contact angles of the water droplet relative to the ultraviolet-unexposed and -exposed portions of the film were measured by sessile drop method; and the dynamic receding contact angle of the water droplet relative to the ultraviolet-unexposed portion of the film was measured by extension/contraction method. In the present invention, the term "static contact angle" refers to, when a droplet of water was deposited onto a surface of a film, an angle formed between the water droplet and the film surface; and the term "dynamic receding contact angle" refers to, when the water droplet is sucked in by a needle etc., a contact angle of the water droplet with the film surface during contraction of the water droplet; and the term "dynamic advancing contact angle" refers to, when the water droplet is sucked out by a needle etc., a contact angle of the water droplet with the film surface during extension of the water droplet.

As a pattern forming material for lithography and printed electronics, it is preferable that, when a pattern forming film is formed from the pattern forming material and exposed, the static contact angle of the unexposed portion of the pattern forming film is high. As the static contact angle of the unexposed portion of the pattern forming film is higher, a mask pattern is transferred more faithfully to the pattern forming film so that a pattern is obtained with good line edge roughness and line width roughness and is high in resolution. Further, it is easy to cut the pattern as the static contact angle of the exposed portion of the pattern forming film is lower and as the difference between the contact angles of the unexposed and exposed portions of the pattern forming film is greater.

As the dynamic contact angle of the unexposed portion of the pattern forming film is higher, a mask pattern is transferred more faithfully to the pattern forming film so that a pattern is obtained with good line edge roughness and line width roughness and is high in resolution. In order to obtain a pattern with high resolution, it is preferable that: both of the static and dynamic contact angles of the unexposed portion of the pattern forming film are high; and the hysteresis (dynamic advancing contact angle—dynamic receding contact angle) of the pattern forming film is small.

[Ink Patterns]

Onto the above-formed water-repellent/hydrophilic pattern on the substrate, 50 pl of an water-based ink was dropped through a borosilicate glass capillary tube (microcapillary). After the lapse of 5 seconds, the pattern was observed with an automatic micro contact angle meter (available as MCA-2 from Kyowa Interface Science Co., Ltd.). The ink pattern was evaluated as follows: "good" when the water-based ink was patterned along the water-repellent/hydrophilic pattern was observed; "failing" when the water-based ink overflowed the water-repellent/hydrophilic pattern; and "fair" when it was impossible to judge whether the water-based ink was patterned or overflowed.

[Measurement Results]

The measurement results of the static and dynamic contact angles of the pattern forming compositions 1 to 9 and the comparative compositions 1 to 4 are shown in TABLE 3. In TABLE 3, Examples 1 to 9 respectively correspond to the pattern forming compositions 1 to 9; and Comparative Examples 1 to 4 respectively correspond to the comparative compositions 1 to 4.

TABLE 3

| | | Static contact angle (°) | | UV unexposed portion | | |
|---|---|---|---|---|---|---|
| | Polymer | UV unexposed portion | UV exposed portion | Dynamic receding contact angle (°) | Hysteresis | Ink pattern |
| Example 1 | Fluorine-containing polymer 1 | 106 | 60 | 93 | 17 | good |
| Example 2 | Fluorine-containing polymer 2 | 105 | 63 | 92 | 19 | good |
| Example 3 | Fluorine-containing polymer 3 | 106 | 62 | 94 | 18 | good |
| Example 4 | Fluorine-containing polymer 4 | 102 | 64 | 82 | 26 | good |
| Example 5 | Fluorine-containing polymer 5 | 103 | 65 | 81 | 27 | good |
| Example 6 | Fluorine-containing polymer 6 | 107 | 63 | 97 | 16 | good |
| Example 7 | Fluorine-containing polymer 7 | 106 | 61 | 95 | 18 | good |
| Example 8 | Fluorine-containing polymer 8 | 108 | 65 | 98 | 15 | good |
| Example 9 | Fluorine-containing polymer 9 | 106 | 63 | 97 | 16 | good |
| Comparative Example 1 | Comparative polymer 1 | 73 | 61 | 58 | 16 | failing |
| Comparative Example 2 | Comparative polymer 2 | 94 | 63 | 80 | 30 | fair |

TABLE 3-continued

| | Polymer | Static contact angle (°) UV unexposed portion | | UV unexposed portion | | |
| --- | --- | --- | --- | --- | --- | --- |
| | | UV unexposed portion | UV exposed portion | Dynamic receding contact angle (°) | Hysteresis | Ink pattern |
| Comparative Example 3 | Comparative polymer 3 | 104 | 62 | 88 | 22 | good |
| Comparative Example 4 | Comparative polymer 4 | 107 | 103 | 97 | 15 | failing |

Hysteresis: Dynamic advancing contact angle − Dynamic receding contact angle

[Contact Angle]

As for each of the films of the pattern forming compositions of Examples 1 to 9, the ultraviolet-unexposed portion exhibited a high contact angle and showed high water repellency.

As for the film of the comparative composition 1 in which the comparative polymer 1 did not contain a fluorine atom, the ultraviolet-unexposed portion exhibited a static contact angle of 73° and a dynamic receding contact angle of 58°. As for the film of the comparative composition 2 in which the comparative polymer 2 contained a fluorine atom, the ultraviolet-unexposed portion exhibited a static contact angle of 94°. The film of the comparative composition 2 was thus inferior in water repellency to the films of the pattern forming compositions of Examples 1 to 9. As for the film of the comparative composition 4 in which the comparative polymer 4 contained a hexafluoriisopropyl group not decomposable by an acid, the ultraviolet-exposed portion had a high contact angle and did not show hydrophilicity.

[Ink Pattern]

As for the water-repellent/hydrophilic patterns of Examples 1 to 9 formed from the pattern forming compositions 1 to 9 using the fluorine-containing polymers 1 to 9, the difference between the contact angles of the unexposed and exposed portions was 40° or greater; and the dynamic receding contact angle of the unexposed portion was high. Thus, each of these water-repellent/hydrophilic patterns allowed rapid flow of the water-based ink from water-repellent portion to the hydrophilic portion.

As for the water-repellent/hydrophilic pattern formed from the comparative composition 2 using the comparative polymer 2, by contrast, the difference between the contact angles of the unexposed and exposed portions was about 300; and the dynamic receding contact angle of the unexposed portion was at a low level of 80°. For these reasons, there was observed a residue of the water-based ink on the water-repellent portion. As for Comparative Example 1 in which the comparative polymer 1 did not contain a fluorine atom, the water-repellent portion did not show sufficient water repellency and had wettability with water whereby there occurred a residue of the water-based ink on the water-repellent portion. As for Comparative Example 4 in which the comparative polymer 4 contained a hexafluoriisopropyl group not decomposable by an acid, the water-repellent/hydrophilic pattern was not formed so that a film of the water-based ink was present on a surface of the film.

7. Resists 7.1 Preparation of Resist

Resists 1 to 3 and comparative resists 1 to 4 as resist solutions were repapered using the fluorine-containing polymers 10 to 12 and the comparative polymers 5 to 7. The repeating units of the respective polymers were as shown below.

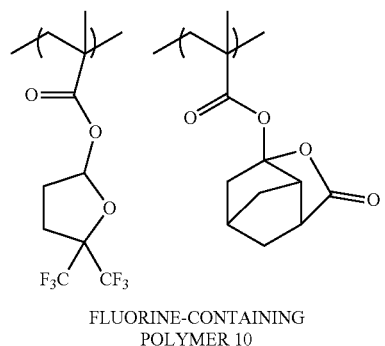

FLUORINE-CONTAINING POLYMER 10

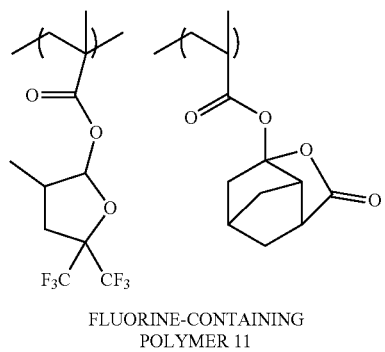

FLUORINE-CONTAINING POLYMER 11

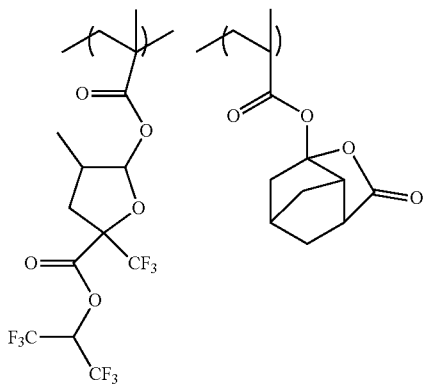

FLUORINE-CONTAINING POLYMER 12

-continued

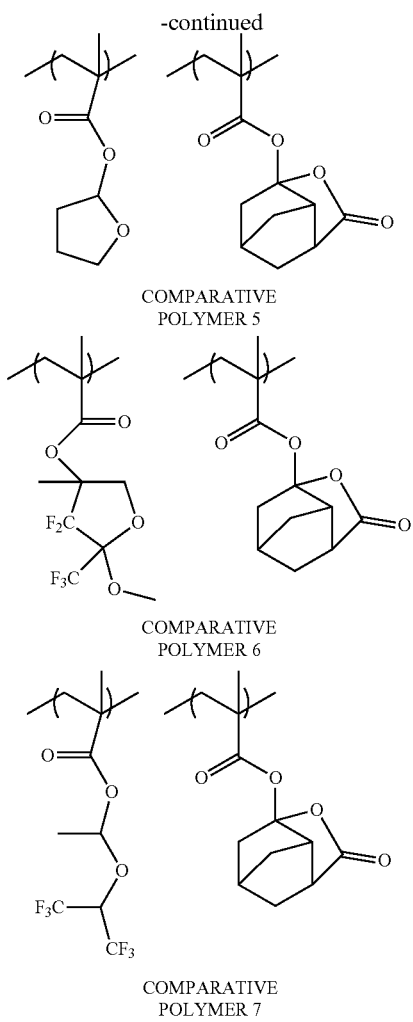

COMPARATIVE POLYMER 5

COMPARATIVE POLYMER 6

COMPARATIVE POLYMER 7

More specifically, the respective resist solutions were prepared by adding triphenylsulfonium nonafluorobutanesulfonate as a photoacid generator, triethanolamine as a basic compound and propylene glycol monomethyl ether acetate (PGMEA) as a solvent to the polymer such that content ratio of polymer:photoacid generator:basic compound:solvent was 100:5:1:900 in terms of parts by mass.

[Formation of Resist Film]

An anti-reflection film was formed with a thickness of 78 nm on a silicon wafer by applying an anti-reflection film forming solution (available under the product name of ARC29A from Nissan Chemical Corporation) to the silicon wafer and drying the applied film at 200° C. for 60 seconds. Subsequently, the above-prepared resist solution was filtered with a 0.2-μm membrane filter, applied onto the anti-reflection film by a spinner at 1500 rpm, and then, dried on a hot plate at 100° C. for 90 seconds, whereby there was obtained a resist film.

7.2 Evaluations of Developer Solubility of Resist and Resist Pattern Resolution

Evaluations of the developer solubility and resist pattern resolution of the respective resist films and measurement of the contact angle of the respective resist films were made by the following methods.

[Evaluation of Developer Solubility]

The above-formed resist film on the silicon wafer was tested for the solubility in a developer by immersing the resist film in an alkaline developer solution for 60 seconds at room temperature. The alkaline developer solution used was an aqueous solution of 2.38 mass % tetramethylammonium hydroxide (TMAH). The developer solubility of the resist film was judged by measuring the thickness of the resist film after the immersion with an optical interference type thickness meter. The resist film was evaluated as: "soluble" when the resist film completely disappeared; and "insoluble" when there was seen no change in the thickness of the film.

[Evaluations of Resist Sensitivity and Resist Pattern Resolution]

Provided was a photomask having a line-and-space pattern in which both the width of lines and the space between adjacent lines were 30 nm. The above-formed resist film on the silicon wafer was subjected to prebaking at 100° C. for 60 seconds. Then, the resist film was exposed to ultraviolet light, which was emitted from an argon fluoride excimer laser with an oscillation wavelength of 193 nm, through the photomask such that the pattern of the photomask was transferred to the resist film. While rotating the silicon wafer, pure water was dropped onto the resist film. The resist film was subjected to post-exposure baking at 120° C. for 60 seconds. After that, the resist film was developed with an alkaline developer solution of TMAH. The resist film was immersed in water for 30 seconds and dried by an air knife. Subsequently, post baking treatment was performed to dry the resist film at 100° C. for 45 seconds. With this, there was obtained a resist pattern on the silicon wafer.

<Sensitivity>

In the above operation, the optimum exposure amount Eop (mj/cm$^2$) at which the pattern of 30-nm line and space was reproduced by one exposure was determined and utilized as an index of sensitivity.

<Resolution>

The above-obtained resist pattern on the silicon, to which the photomask pattern of 30-nm line and space was transferred, was cut and then was observed with a microscope. The resolution of the resist pattern was evaluated as: "excellent" when no line edge roughness was seen; "good" when line edge roughness was seen but was very low; and "failing" when line edge roughness was pronounced.

[Measurement of Contact Angle]

Using a contact angle meter (available from Kyowa Interface Science Co., Ltd.), the contact angle of a water droplet with the above-formed resist film on the silicon wafer was measured. As the contact angle of a resist film is higher, a mask pattern is transferred more faithfully to the resist film so that a pattern is obtained with good line edge roughness and line width roughness and is high in resolution. Further, there occurs less water mark defect without the entry of water into the film in lithography when the contact angle is high.

The evaluation results of the developer solubility, sensitivity and resist pattern resolution of the respective resist films and the measurement results of the contact angle of the respective resist films are shown in TABLE 4.

TABLE 4

| Resist | Polymer | Solubility in alkaline developer | | Resist performance | | Dynamic receding contact angle (°) | |
|---|---|---|---|---|---|---|---|
| | | Before exposure | After exposure | Sensitivity (mJ/cm²) | Resolution | Before exposure | After development |
| Resist 1 | Fluorine-containing polymer 10 | insoluble | soluble | 34 | good | 82 | 60 |
| Resist 2 | Fluorine-containing polymer 11 | insoluble | soluble | 35 | good | 82 | 61 |
| Resist 3 | Fluorine-containing polymer 12 | insoluble | soluble | 38 | good | 84 | 58 |
| Comparative Resist 1 | Comparative polymer 5 | insoluble | soluble | 48 | failing | 65 | 58 |
| Comparative Resist 2 | Comparative polymer 6 | insoluble | soluble | 44 | good | 76 | 62 |
| Comparative Resist 3 | Comparative polymer 7 | insoluble | soluble | 60 | fair | 81 | 61 |

[Evaluation Results of Developer Solubility]

As shown in TABLE 4, each of the resists 1 to 3 and the comparative resists 1 to 3 was insoluble in the alkaline developer solution before the exposure, but became soluble in the alkaline developer solution after the exposure. Thus, all of the tested resists served as photosensitive resin compositions and had dissolution contrast in TMAH as the alkaline developer solution.

[Evaluation Results of Resist Pattern Sensitivity and Resolution]

<Sensitivity>

Each of the optimum exposure amounts of the comparative resists 1 to 3 corresponded to a lower sensitivity level than those of the resists 1 to 3. The resists 1 to 3 were higher in sensitivity than the comparative resist 2 in which the polymer had a cyclic acetal structure. The comparative resist 1 in which the polymer had a cyclic acetal structure but did not contain a fluorine atom was low in sensitivity. The comparative resist 3 in which the polymer had an acyclic acetal structure was the lowest in sensitivity.

<Resolution>

In the case of using each of the resists 1 to 3 and the comparative resist 2, the resist pattern was formed with a line-and-space of 30 nm as desired and was high in resolution so that the resolution of the resist pattern was evaluated as "good" as shown in TABLE 4. As for the comparative resist 1, by contrast, line edge roughness was seen on the resist pattern so that the resolution of the resist pattern was evaluated as "failing".

[Measurement Results of Contact Angle]

In either case, the films of the resists 1 to 3 had a dynamic receding contact angle higher than those of the comparative resists 1 and 2. The film of the comparative resist 2 was lower in contact angle than the films of the resists 1 to 3 even though the polymer with a fluorine-containing cyclic hemiacetal structure was contained in the comparative resist 2.

The invention claimed is:

1. A fluorine-containing polymer comprising a repeating unit of the following formula (1)

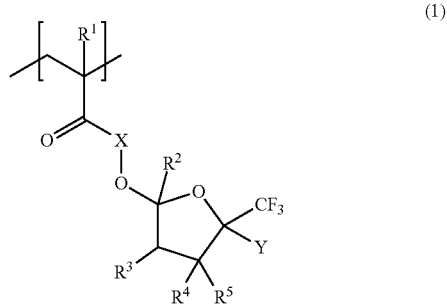

where $R^1$ is a hydrogen atom, a fluorine atom, or a $C_1$-$C_{10}$ linear or $C_3$-$C_{10}$ branched alkyl group in which seven or less of hydrogen atoms bonded to carbon atoms may be substituted with fluorine; $R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; X is a single bond, or a divalent group in which seven or less of hydrogen atoms may be substituted with fluorine; Y is a $C_1$-$C_3$ fluoroalkyl group or a carboxylate group represented by —COOR in which R is a $C_1$-$C_3$ fluoroalkyl group.

2. The fluorine-containing polymer according to claim 1, wherein $R^2$, $R^4$ and $R^5$ in the formula (1) are respectively hydrogen atoms.

3. The fluorine-containing polymer according to claim 2, wherein Y in the formula (1) is a trifluoromethyl group.

4. A resist pattern forming composition comprising:
the fluorine-containing polymer according to claim 1;
an acid generator;
a basic compound; and
a solvent.

5. A resist pattern forming method comprising:
a film forming step of forming a film of the resist pattern forming composition according to claim 4 on a substrate;
an exposure step of subjecting the film to exposure to electromagnetic wave or high energy ray radiation of wavelength 300 nm or shorter through a photomask to thereby transfer a pattern of the photomask to the film; and a development step of developing the film with a developer to obtain the pattern.

6. An ink pattern forming composition comprising:
the fluorine-containing polymer according to claim 1;
an acid generator; and
a solvent.

7. An ink pattern forming method comprising:
a film forming step of forming a film of the ink pattern forming composition according to claim 6 on a substrate;
an exposure step of subjecting the film to exposure to light radiation of wavelength 150 to 500 nm through a photomask to transfer a pattern of the photomask to the film, thereby obtaining a pattern forming film with a liquid-repellent portion and a liquid-philic portion; and
an ink pattern forming step of applying an ink to the pattern forming film.

8. An ink pattern forming method comprising:
a film forming step of forming a film of the ink pattern forming composition according to claim 6 on a substrate and heating the film;
a drawing step of drawing a pattern on the film by subjecting the film to scanning exposure to light radiation of wavelength 150 to 500 nm by means of drawing equipment, thereby obtaining a pattern forming film with a liquid-repellent portion and a liquid-philic portion; and
an ink pattern forming step of applying an ink to the pattern forming film.

9. A fluorine-containing monomer of the following formula (4)

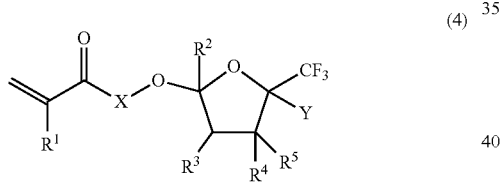
(4)

where $R^1$ is a hydrogen atom, a fluorine atom, or a $C_1$-$C_{10}$ linear or $C_3$-$C_{10}$ branched alkyl group in which seven or less of hydrogen atoms bonded to carbon atoms may be substituted with fluorine; $R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; X is a single bond, or a divalent group in which seven or less of hydrogen atoms may be substituted with fluorine; Y is a $C_1$-$C_3$ fluoroalkyl group or a carboxylate group represented by —COOR in which R is a $C_1$-$C_3$ fluoroalkyl group.

10. The fluorine-containing monomer according to claim 9, wherein $R^2$, $R^4$ and $R^5$ in the formula (4) are respectively hydrogen atoms.

11. The fluorine-containing monomer according to claim 10, wherein Y in the formula (4) is a trifluoromethyl group.

12. A method for producing the fluorine-containing monomer of the formula (4) according to claim 9, comprising:
forming a cyclic hemiacetal compound of the following formula (7) by cyclization of a hydroxycarbonyl compound of the following formula (10) or a hydroxyvinyl ether or hydroxyvinyl ester of the following formula (11); and reacting the cyclic hemiacetal compound with a compound represented by $CH_2$=$CR^1$—CO—X—A, thereby forming the fluorine-containing monomer of the formula (4)

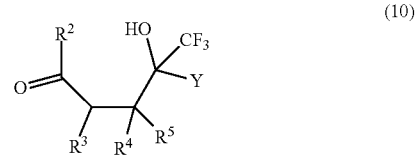
(10)

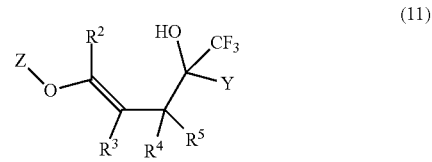
(11)

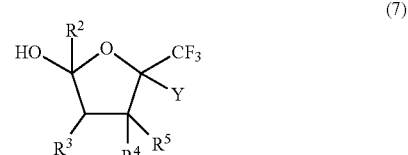
(7)

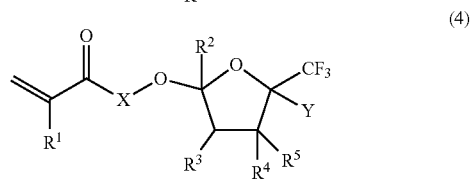
(4)

where $R^1$ is a hydrogen atom, a fluorine atom, or a $C_1$-$C_{10}$ linear or $C_3$-$C_{10}$ branched alkyl group in which seven or less of hydrogen atoms bonded to carbon atoms may be substituted with fluorine; $R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; X is a single bond, or a divalent group in which seven or less of hydrogen atoms may be substituted with fluorine; Y is a $C_1$-$C_3$ fluoroalkyl group or a carboxylate group represented by —COOR in which R is a $C_1$-$C_3$ fluoroalkyl group; Z is a hydrogen atom, or a $C_1$-$C_{20}$ linear or $C_3$-$C_{20}$ branched or cyclic alkyl group in which a part or all of hydrogen atoms may be substituted with fluorine and which may contain an ether bond, a siloxane bond, a thioether bond or a carbonyl bond; and A is a hydrogen atom, a halogen atom, an acryloyl group or a methacryloyl group.

13. A fluorine-containing cyclic hemiacetal compound of the following formula (7)

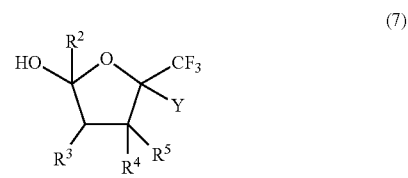
(7)

where $R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; Y is a $C_1$-$C_3$ fluoroalkyl group or a carboxylate group represented by —COOR in which R is a $C_1$-$C_3$ fluoroalkyl group.

14. The fluorine-containing cyclic hemiacetal compound according to claim 13, wherein $R^2$, $R^4$ and $R^5$ in the formula (7) are respectively hydrogen atoms.

15. The fluorine-containing cyclic hemiacetal compound according to claim 14, wherein Y in the formula (7) is a trifluoromethyl group.

16. A method for producing the fluorine-containing cyclic hemiacetal compound of the formula (7) according to claim 13, comprising:

performing cyclization of a hydroxycarbonyl compound of the following formula (10) or a hydroxyvinyl ether or hydroxyvinyl ester of the following formula (11)

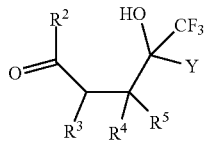 (10)

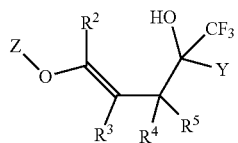 (11)

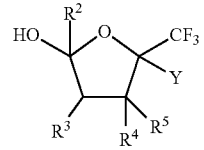 (7)

where $R^2$ to $R^5$ are each independently a hydrogen atom, or a $C_1$-$C_{10}$ linear or $C_3$-$C_{10}$ branched alkyl group in which seven or less of hydrogen atoms bonded to carbon atoms may be substituted with fluorine; Y is a $C_1$-$C_3$ fluoroalkyl group or a carboxylate group represented by —COOR in which R is a $C_1$-$C_3$ fluoroalkyl group; and Z is a hydrogen atom, or a $C_1$-$C_{20}$ linear or $C_3$-$C_{20}$ branched or cyclic alkyl group in which a part or all of hydrogen atoms may be substituted with fluorine and which may contain an ether bond, a siloxane bond, a thioether bond or a carbonyl bond.

* * * * *